United States Patent
Schüpbach et al.

[19]

[11] Patent Number: 5,807,669
[45] Date of Patent: Sep. 15, 1998

[54] PROCESS FOR THE DETECTION OF REVERSE TRANSCRIPTASE

[76] Inventors: Jörg Schüpbach, Bachtalsteig 4, CH-5400 Ennetbaden, Switzerland; Jürg Böni, Kollerstrasse 8, CH-5430 Wettingen, Switzerland

[21] Appl. No.: 178,256

[22] PCT Filed: May 10, 1993

[86] PCT No.: PCT/CH93/00116

§ 371 Date: Apr. 26, 1994

§ 102(e) Date: Apr. 26, 1994

[87] PCT Pub. No.: WO93/23560

PCT Pub. Date: Nov. 25, 1993

[30] Foreign Application Priority Data

May 11, 1992 [CH] Switzerland ............... 1502/92

[51] Int. Cl.$^6$ ............... C12Q 1/00; C12Q 1/70; C12Q 1/68; C07H 21/02
[52] U.S. Cl. ............ 435/4; 435/5; 435/6; 435/91.2; 536/23.1; 536/24.3
[58] Field of Search ............... 435/5, 6, 4, 91.2; 536/23.1, 24.3

[56] References Cited

U.S. PATENT DOCUMENTS

| | | | |
|---|---|---|---|
| 4,965,188 | 10/1990 | Mullis et al. | 435/6 |
| 5,021,335 | 6/1991 | Tecott et al. | 435/6 |
| 5,409,818 | 4/1995 | Davey et al. | 435/91.21 |
| 5,427,930 | 6/1995 | Birkenmyer et al. | 435/91.21 |

FOREIGN PATENT DOCUMENTS

WO92/04467 10/1990 WIPO .
92/04467 3/1992 WIPO .

OTHER PUBLICATIONS

Silver et al, "A Sensitive Assay for Reverse Transcriptase Based on RT–PCR" (Abstract only) (May 1993).
Silver et al, "An RT–PCR Assay for the Enzyme Activity of Reverse Transcriptase Capable of Detecting Single Virions", *Nucleic Acids Research*, 21(15):3593 (1993).
Centers for Disease Control and Prevention, *Federal Register*, 59(200):52550 (Oct. 18, 1994).

(List continued on next page.)

*Primary Examiner*—W. Gary Jones
*Assistant Examiner*—Ethan Whisenaut
*Attorney, Agent, or Firm*—Burns, Doane, Swecker & Mathis, L.L.P.

[57] ABSTRACT

An ultrasensitive procedure for the detection of reverse transcriptase (RT) is proposed, which is divided into three steps:

In the first step the sample is processed by placing a template-primer combination in a reaction mixture and using the RT activity present in the pretreated sample to provide a nucleic acid to be amplified in a given nucleic acid amplification procedure so as to ensure that this is only provided if there is RT activity in the sample.

In the second step the nucleic acid to be amplified is amplified, the result being an amplification product.

In the third step the amplification product is analyzed and identified.

Compared to conventional RT assays a several million fold increase of sensitivity is achieved, thus the ultrasensitive detection of RT activity is made possible, that is the detection of all retroviruses as well as other retroelements containing or expressing active RT.

The procedure is of importance for the diagnosis of infections and diseases caused by these in humans, animals and plants. Screening and typing kits are suggested for research and diagnostics.

26 Claims, 33 Drawing Sheets

OTHER PUBLICATIONS

Heneine et al, "Detection of Reverse Transcriptase by a Highly Sensitive Assay in Sera from Persons Infected with Human Immunodeficiency Virus Type 1", *The Journal of Infectious Diseases*, 171:1210 (1995).

Lee et al., J. Medical Virology 23:323–329 (1987).

Hoffman et al., Virology 147:326–335 (1985).

"Comparative Diagnosis of Viral Diseases, vol. II" Eds. Kurstak et al., Academic Press, 1977, pp. 122–126.

Lee, Y., Journal of Virological Methods 20 : 89–94 (1988).

Donehower et al., Journalk of Virological Methods 28 : 33–46 (1990).

Maudru et al., Journal of Virological Methods 66 : 247–261 (1997).

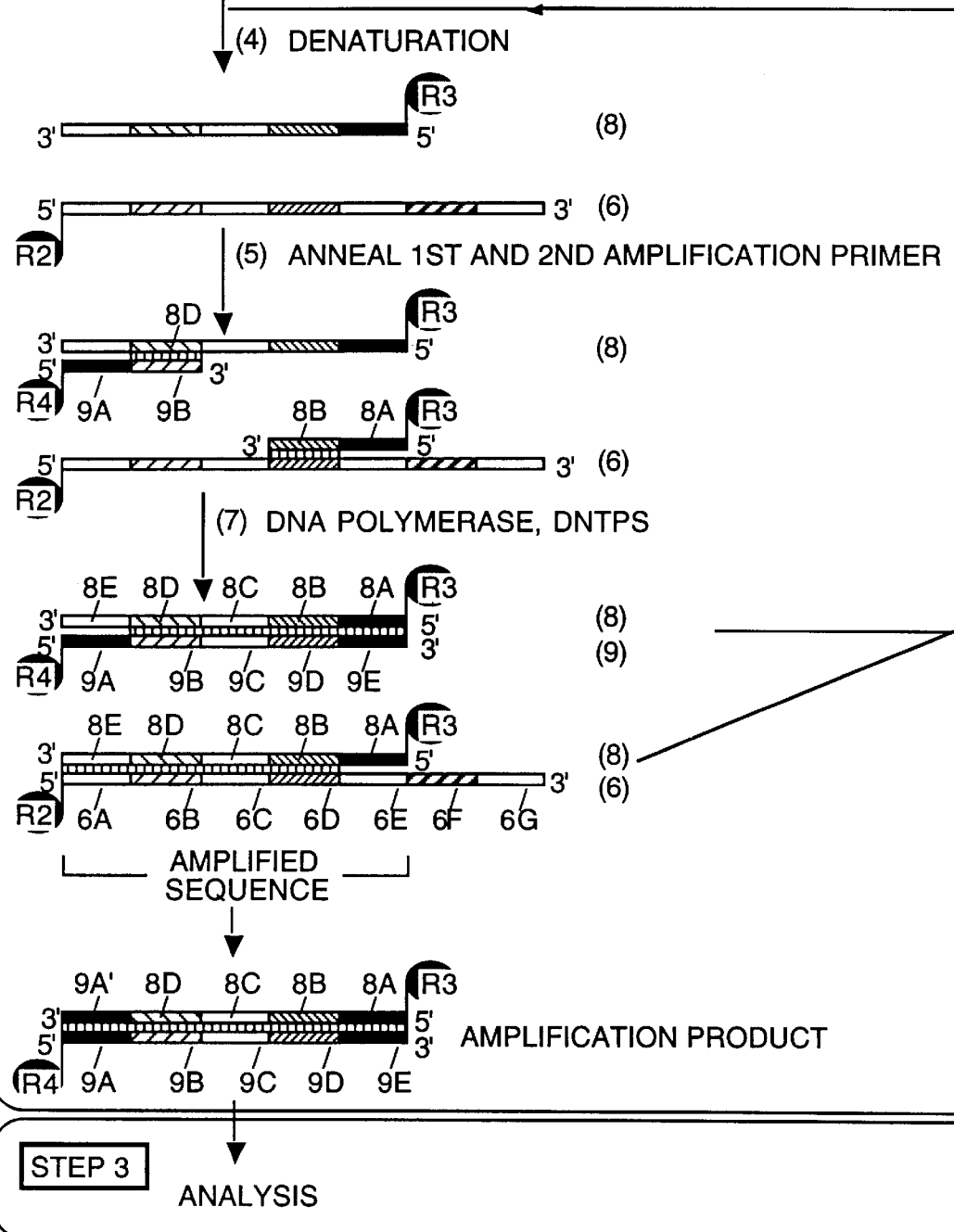

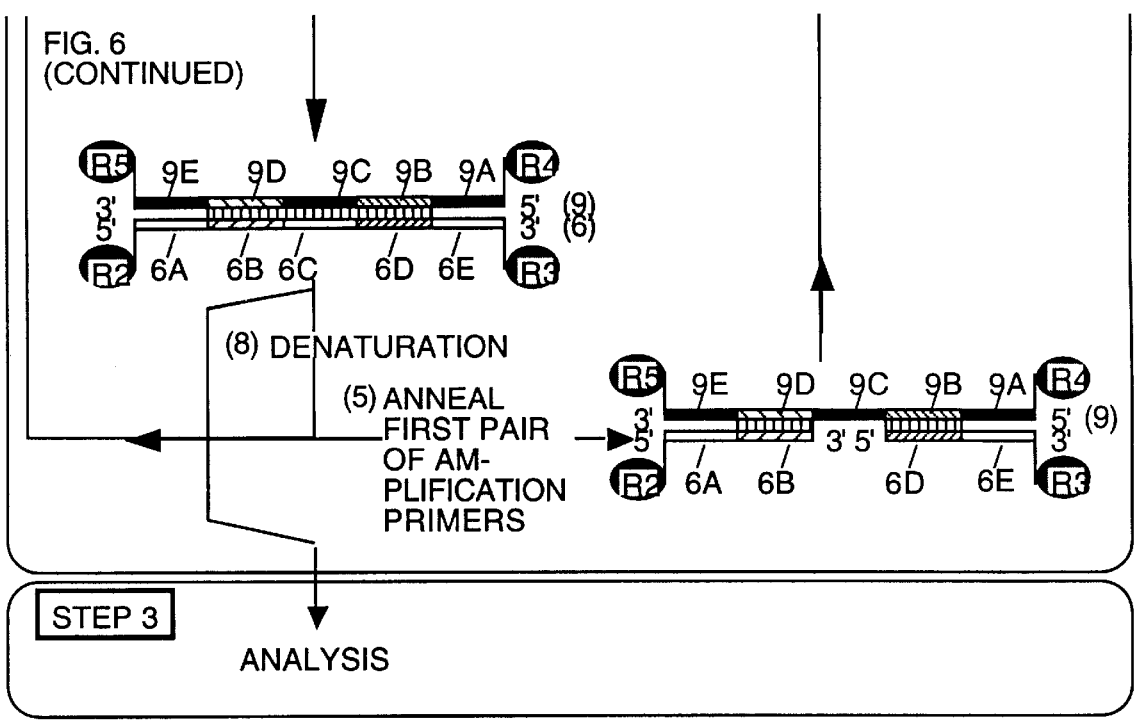

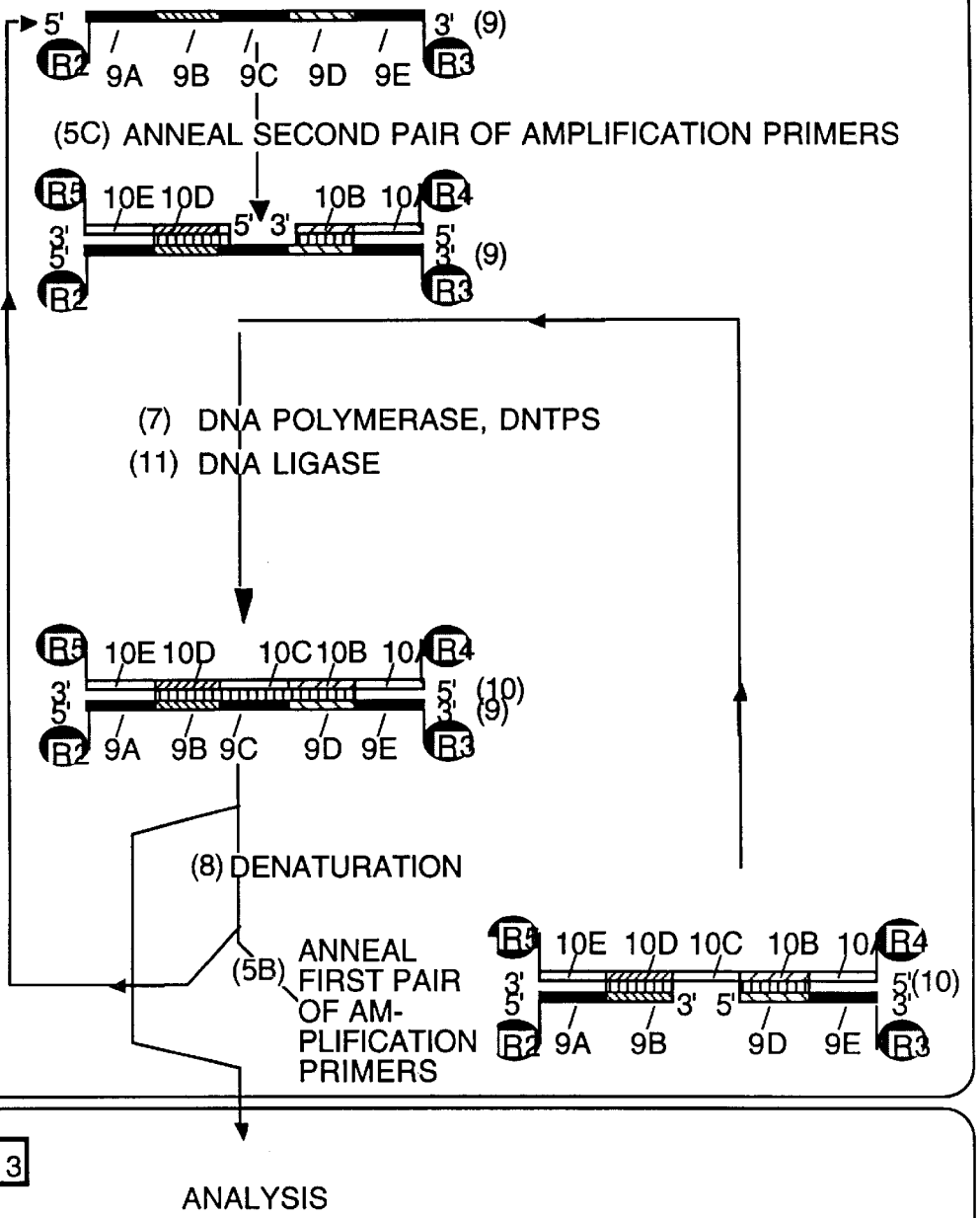

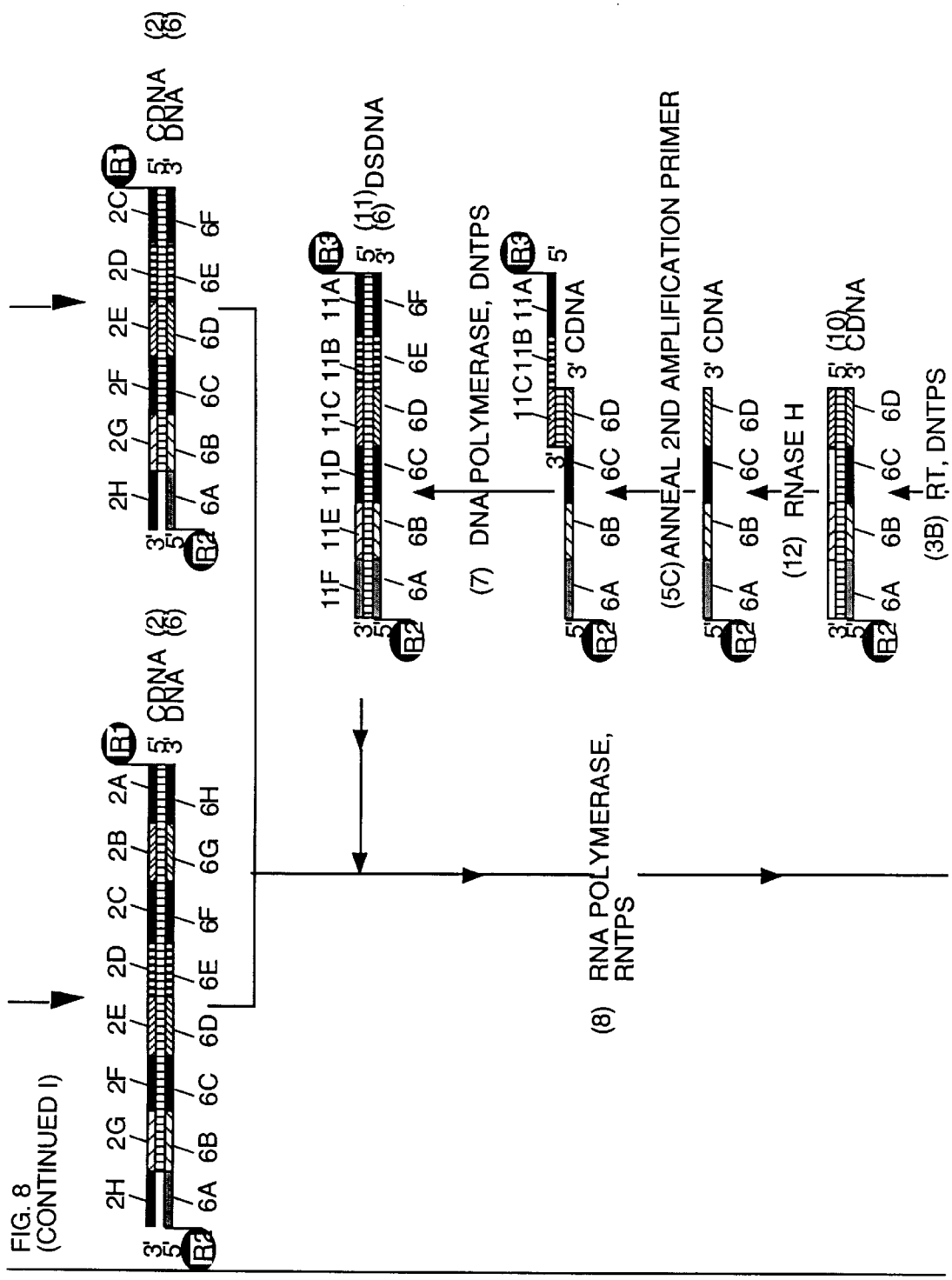

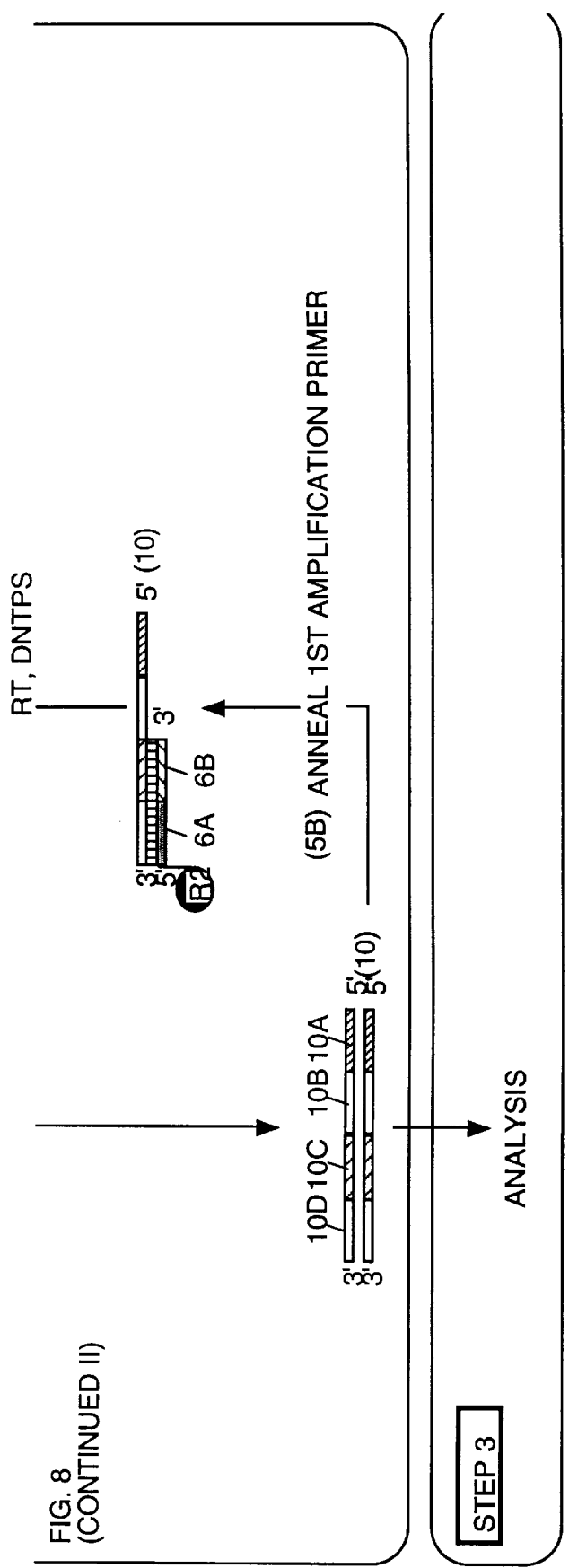

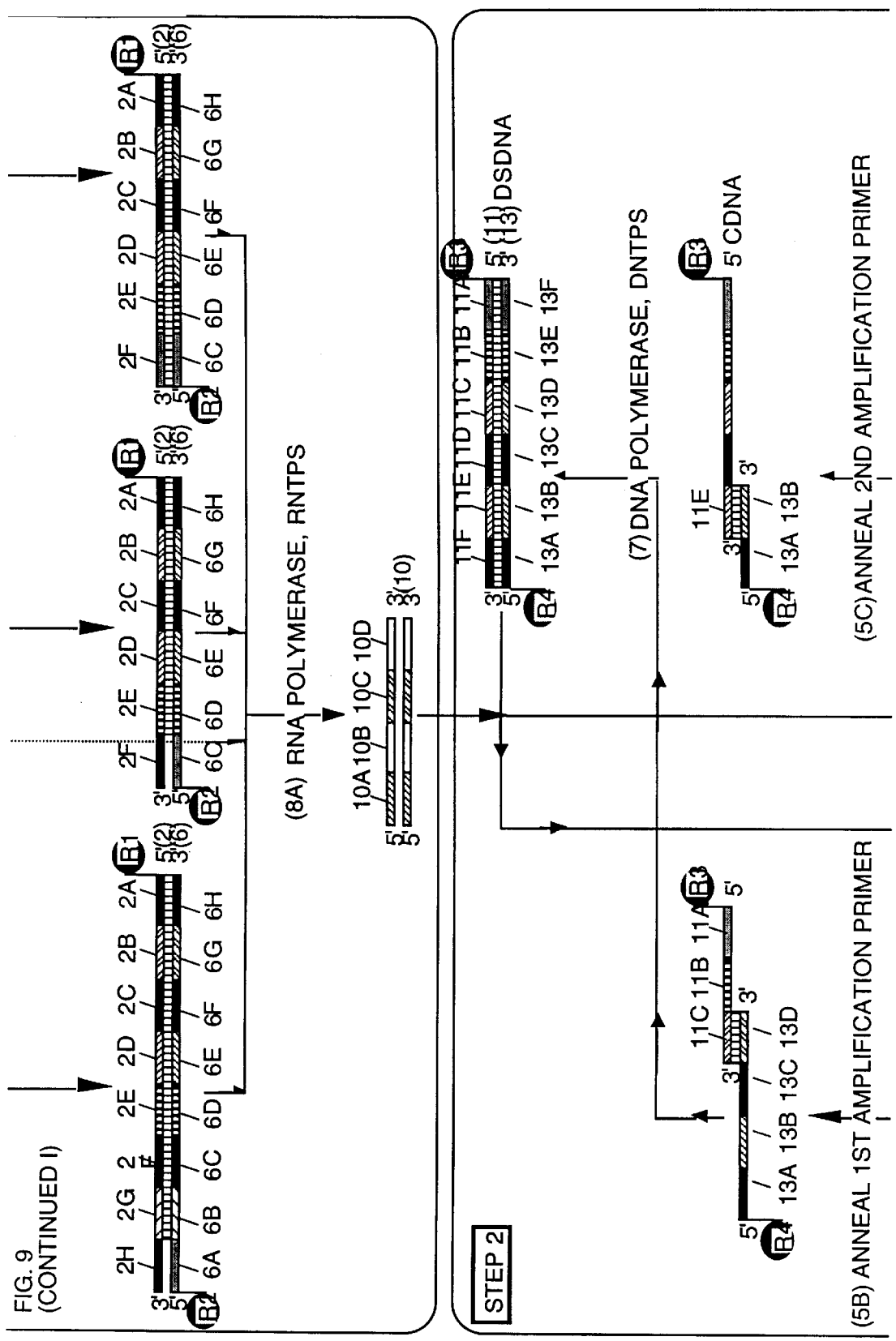

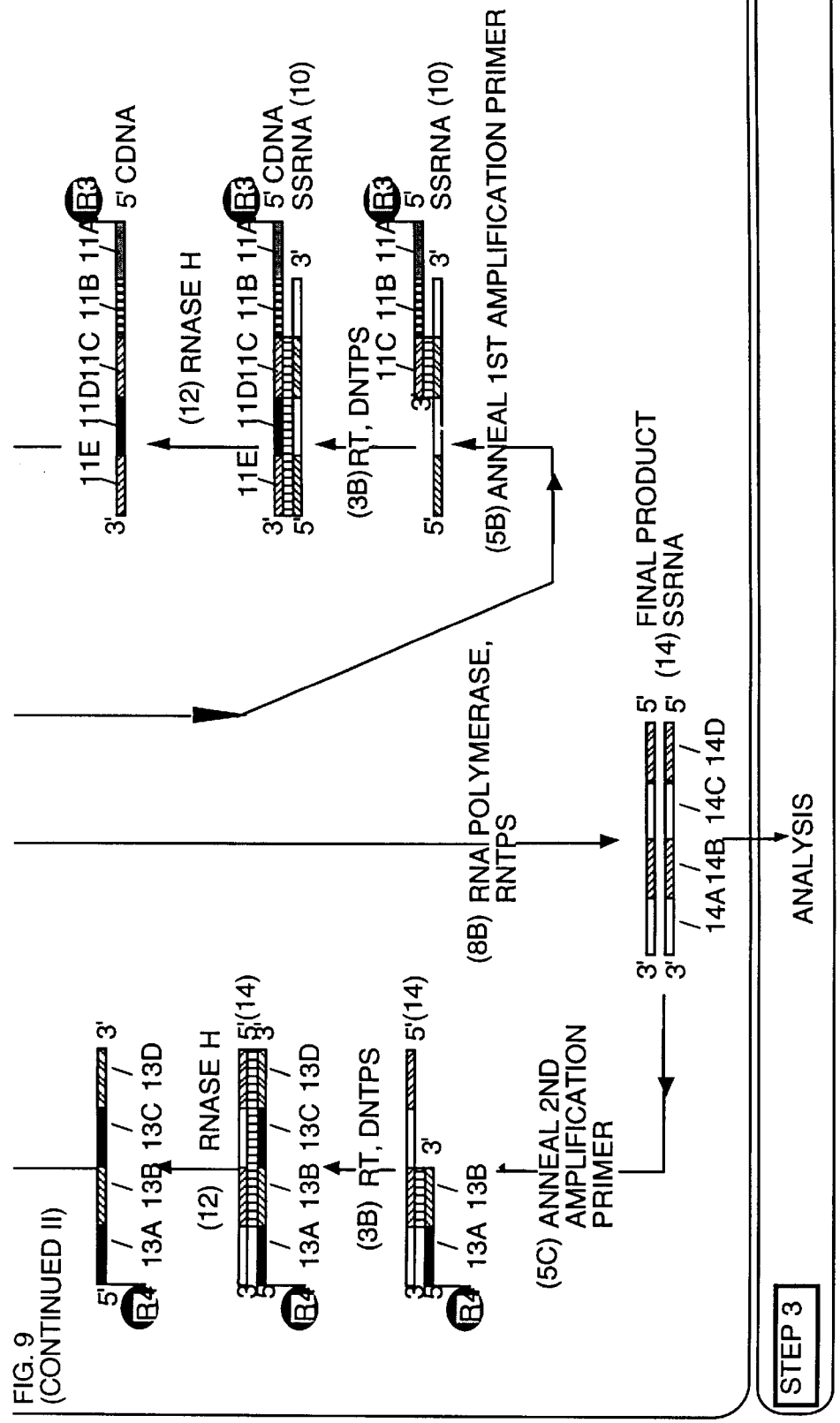

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic oligodeoxyribonucleotide"

( i i i ) HYPOTHETICAL: NO ( i x ) FEATURE:
        ( A ) NAME/KEY: misc_feature
        ( B ) LOCATION: 1..24
        ( D ) OTHER INFORMATION: /note= "Reverse transcriptase primer."

( x i ) SEQUENCE DESCRIPTION: SEQ ID NO:1:

CATAGGTCAA ACCTCCTAGG AATG 24

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligodeoxyribonucleotide"

( i i i ) HYPOTHETICAL: NO ( i x ) FEATURE:
        ( A ) NAME/KEY: misc_feature
        ( B ) LOCATION: 1..22
        ( D ) OTHER INFORMATION: /note= "PCR primer."

( x i ) SEQUENCE DESCRIPTION: SEQ ID NO:2:

TCCTGCTCAA CTTCCTGTCG AG 22

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligodeoxyribonucleotide"

( i i i ) HYPOTHETICAL: NO ( i x ) FEATURE:
        ( A ) NAME/KEY: misc_feature
        ( B ) LOCATION: 1..21
        ( D ) OTHER INFORMATION: /note= "Probe."

( x i ) SEQUENCE DESCRIPTION: SEQ ID NO:3:

TTAATGTCTT TAGCGAGACG C 21

PROCESS FOR THE DETECTION OF REVERSE TRANSCRIPTASE

FIELD OF THE INVENTION

The invention deals with methods that allow the ultrasensitive detection of reverse transcriptase (RNA-dependent DNA-polymerase or deoxynucleoside triphosphate:DNA deoxynucleotidyl transferase) in a sample.

The invention includes both screening kits for the detection of reverse transcriptase by means of these methods and typing kits which relate reverse transcriptase activity to a certain agent or a group of agents with certain common features.

BACKGROUND OF THE INVENTION

Reverse transcriptase (referred to as RT in this text) is an indispensable component of mature virions of replication-competent retroviruses (Baltimore D. Nature 1970; 226:1209–1211; Temin HM and Mizutani S. Nature 1970; 226:1211–3). However, enzymes showing activites at least in part similar can also occur in a number of other retroelements, which do not belong to the family of retroviruses. On the one hand these include the retrovirus-like elements, which are subdivided into retrotransposons, pararetroviruses (caulimoviruses and hepadnaviruses) and LINE-elements, on the other hand the non-retrovirus-like elements such as mitochondrial plasmids or msDNA (for a recent survey of retroelements see Ricchetti M. Bull Inst Pasteur 1991; 89:147–58). Therefore this invention also describes methods for the ultrasensitive detection of all retroviruses as well as other retroelements which contain or express active RT. RTs are enzymes (RNA-dependent DNA polymerases) that, based on a given template RNA (substrate), produce the complementary DNA (cDNA). The result of this reaction, which is referred to as reverse transcription reaction (RT reaction), is a RNA/cDNA heteroduplex. A further activity of retroviral RTs is a RNase H function. Finally they also have DNA-dependent polymerase activity. For a survey on the properties of retroviral reverse transcriptase see H. Varmus and R. Swanstrom: Replication of Retroviruses; in: *RNA Tumor Viruses*, 2nd ed. R. Weiss, N. Teich, H. Varmus, J. Coffin, edts. Cold Spring Harbor Laboratory 1984 and 1985, chpts. 5 and S5.

All functional tests currently used for the detection of RT are based on the RNA-dependent synthesis of DNA. The natural template for the enzyme consists of the 70S genomic RNA contained in the virions. However, by using synthetic RNA homopolymers efficiency is increased 10 to 1000 fold. Independent of whether the template is homo- or heteropolymeric, the RT reaction depends of the presence of a suitable RT primer. Under natural circumstances this is a tRNA characteristic of the respective virus, though in most diagnostic RT assays oligodeoxyribonucleotides are used as primers. The most commonly used template-primer combinations today are homopolymers of the poly(rA)-oligo(dT) type. Since these can also be used by a number of eucaryotic DNA polymerases, they are frequently replaced by poly(rC)-oligo(dG). However, this combination can still be used by certain procaryotic DNA polymerases. These enzymes can even efficiently use heteropolymeric RNA templates (Gerard GF and Grandgenett DP. Retrovirus Reverse Transcriptase. In: *Molecular Biology of RNA Tumor Viruses*, JR Stephenson ed., Academic Press, New York, 1980, chpt. 9).

A standard procedure commonly used today for the detection of RT can be described as follows: Poly(rA) [resp. poly(rC)] homopolymer is used as the substrate to which a synthetic deoxyribonucleotide oligomer dT (or dG, resp.) of approximately 12 to 24 bases length is hybridized as a primer. After suitable preparation the sample containing the RT is added to a reaction mixture containing the template-primer combination, $^3$H-marked nucleoside triphosphate dTTP (resp. dGTP), a suitable divalent cation (Mg++or Mn++), and possibly other substances supporting the reaction, in a suitable buffer system. After incubation for a certain time and at a suitable temperature the reaction is stopped, the heteroduplex is precipitated by adding trichloric acid and transferred to a filter. The dried filter is then added to scintillation fluid, and the incorporated radioactivity is measured by means of liquid scintillation techniques (see U.S. Pat. No. 3,755,086, similar techniques have also been described by Poiesz B et al., Proc.Natl Acad Sci USA 1980; 77:1415; Hoffmann AD et al., Virology 1985; 147:326 as well as various other authors). Modifications of this assay, which allow for a slightly increased sensitivity and/or easier application and/or certain other advantages, include the use of other isotopes [e.g. $^{35}$S, $^{32}$P or gamma radiation emitters; see e.g. PCT-application WO 90/06373)], of non-radioactive labelled nucleoside triphosphates, or of a substrate immobilized on a carrier (e.g. EP application 90106847.8 of Apr. 10, 1990), or of ELISA-formates (e.g. Eberle J et al., Reverse transcriptase activity measured by ELISA, Abstract M.A. 1084, VII International Conference on AIDS. Florence, Jun. 16–21, 1991).

Even in combination with synthetic homopolymeric templates current RT assays are relatively insensitive when compared to other methods for the detection of retroviruses. Thus RT activity in cell cultures infected with human immundeficiency virus (HIV) can only be detected at a concentration of HIV increased by about 100 times compared to virus detection by means of the virus-specific (p24) antigen detection (Lee YS. J Virol Meth 1988; 20:89–94). Other methods, e.g. the detection of viruses by cell cultures (HoDD et al. N Engl J Med 1989; 321:1621–5) or various molecular diagnostic procedures for the detection of specific nucleic acid sequences of the agent in question reach an analytical sensitivity that again exceeds that of antigen detection by several orders of magnitude. The high degree of sensitivity is reached by amplifying selected nucleic acid sequences by means of various procedures, thus producing large quantities of the respective nucleic acid. Amplification methods include:

1. Polymerase Chain Reation (PCR) U.S. Pat. No. 4,683, 202 Process for Amplifying Nucleid Acid Sequences; priority Oct. 25, 1985, patent Nov. 28, 1987 U.S. Pat. No. 4,683,195 Process for Amplifying, Detecting and/ or Cloning Nucleic Acid Sequences; priority Feb. 7,1986, patent Jul. 28, 1987

2. Ligase Detection Reaction (LDR)/Ligase Chain Reaction (LCR) WO 89/12696 Method and Reagents for Detecting Nucleic Acid Sequences; priority Jun. 24, 1988, international disclosure Dec. 28, 1989 WO 89/09835 Ligase-Based Amplification Method; priority Apr. 8, 1988; int. discl. Oct. 19, 1989

3. Amplification/detection based on transcription procedures EP 0 208 295 Nucleic Acid Sequence Amplification Methods, priority Jul. 11, 1989, int. discl. Jan. 16, 1991 WO 89/01050 Selective Amplification of Target Polynucleotide Sequence; priority Jul. 31, 1987, int. discl. Feb. 9, 1989 WO 88/10315 Transcription-Based Nucleic Acid Amplification Detection System; priority Jun. 19, 1987/Jun. 6, 1988, int. discl. Dec. 29, 1988

4. Assays based on replicative RNA WO 90/03445 Target Nucleic Acid Amplification/Detection System; priority Sep. 30, 1988; int. discl. Apr. 5, 1990 WO 90/02820 Replicative RNA-Based Amplification/Detection priority Sep. 8, 1988 (USA); int. discl. Mar. 22, 1990 U.S. Pat. No. 4,957,858 Replicative RNA Reporter Systems; priority Apr. 16, 1988; patent Sep. 18, 1990 U.S. Pat. No. 4,786,600 Autocatalytic Replication of Recombinbant RNA; priority May 25, 1984; patent Nov. 22, 1988

5. Assays based on replicative DNA DE 39 29 030 assay for the amplification of nucleic acids; registered Sep. 1, 1989; discl. Mar. 7, 1991 WO 90/10064 Improved Methods for in vitro DNA Amplification and Genomic Cloning and Mapping; priority Mar. 3, 1989; int. discl. Sep. 7, 1990

6. Varia U.S. Pat. No. 4,994,368 Amplification Method for Polynucleotide Assays; priority Jul. 23, 1987; patent Feb. 19, 1991 WO 90/01069 Process for Amplifying and Detecting Nucleic Acid Sequences; priority Jul. 20, 1988; int. discl. Feb. 8, 1990

All these procedures share the following principle: selected nucleic acid sequences are amplified to large quantities, before they are then analysed and identified by common molecular identification procedures. A variant method does not amplify the selected sequence itself but hybridizes another nucleic acid onto this sequence. In addition to the complementary sequence this nucleic acid contains a specific indicator or reporter sequence, which is then amplified (so-called probe-amplification).

A major disadvantage shared by all molecular diagnostic procedures for the detection of retroviruses, and this is especially important with regard to a screening for various retroviruses, is the fact that they are sequence- and therefore virus-specific. This implies that they can only identify agents with a genomic sequence that is, at least partly, known and that normally a test can only detect one single agent. Whenever sequences common to several retroviruses are chosen there is a danger that irrelevant sequences, as e.g. endogenous retroviruses or other obligatory components of the cellular genome of the host species are detected, thus making the test nonspecific. On the other hand, the sensitivity of the method may suffer. The costly cultural detection methods, too, are virus-specific on principle and can only be used when the host cell is known and can be propagated in vitro.

All replication-competent retroviruses have an active RT; therefore, all existing retroviruses can be detected by using a detection method for this enzyme. Furthermore, other retroelements associated with active RT can be detected. However, an efficient diagnostic use of the reverse transcriptase assay requires a considerable increase of analytical sensitivity.

OBJECT AND SUMMARY OF THE INVENTION

It is the object of the invention to propose an assay, called PERT (Product Enhanced Reverse Transcriptase) assay, which leads to an increase in sensitivity in the order of several millions and to describe kits for the assay.

In the sense of the invention, RT acitivity present in a sample is used for providing a nucleic acid to be amplified in a way in which the nucleic acid to be amplified is only provided if RT activity is present in the sample. Subsequently the nucleic acid to be amplified is amplified by means of a suitable amplification method and detected by means of a suitable analytical method. Thus even minute amounts of RT activity can be detected.

Procedures that allow for an increase of sensitivity of the RT assay in the order of several millions are described under claims 1–34.

The invention is described below, by means of figures and examples, as follows:

DETAILED DESCRIPTION OF THE INVENTION

Definitions of Terms

Figure 1:
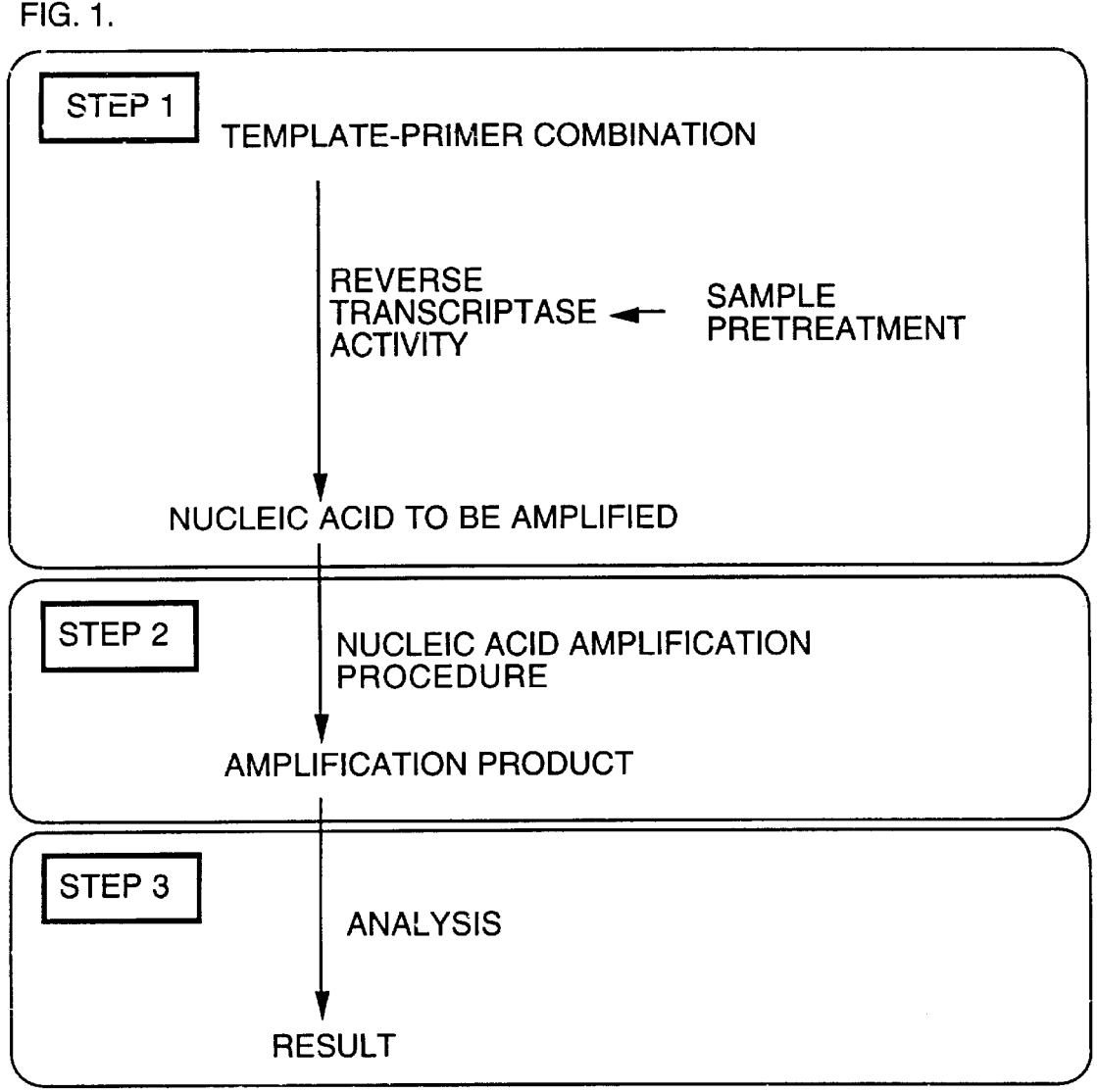
FIG. 1 shows the schematic structure of the PERT assay.

Nucleic Acids, Nucleic Acid Structures and Their Components

The term "nucleotide" refers to any ribonucleotide monophosphate and deoxyribonucleotide monophosphate with any natural or modified base in that structure that occurs [in polymerized form] as a component of a nucleic acid.

The terms "rNTP" and "dNTP" refer to a ribonucleotide triphosphate respectively a deoxyribonucleotide triphosphate with any natural or modified base. The terms "rNTPs" and "dNTPs" refer to a mixture of ribonucleotide triphosphates respectively deoxyribonucleotide triphosphates consisting of at least two different ribonucleotide triphosphates or deoxyribonucleotid triphosphates.

The term "nucleic acid" refers to a single or partly or completely double-stranded oligomer or polymer. If the nucleic acid consists entirely of ribonucleotide monophosphates it is a "RNA", if it consists entirely of deoxyribonucleotide monophosphates, it is a "DNA". However, a nucleic acid may contain both ribonucleotide monophosphates and deoxyribonucleotide monophosphates. The terms "ss" respectively "ds" characterize a nucleic acid as single-stranded respectively double-stranded.

The term "oligonucleotide" refers to a single-stranded nucleic acid consisting of at least two, but not more than one hundred, natural or modified nucleotides or a mixture of these. The oligonucleotide can be or be derived from a natural nucleic acid, or it may be produced by chemical or enzymatic synthesis.

The term "polynucleotide" refers to a single-stranded or double-stranded nucleic acid consisting of more than one hundred natural or modified nucleotides or a mixture of these.

The term "homopolymer" describes nucleic acids or segments of nucleic acids whose nucleotides consist of a single base. This includes bases that are only identical to a complementary base with regard to their binding function, while their chemical structures are different.

The term "heteropolymer" describes nucleic acids or segments of nucleic acids whose nucleotides consist of at least two bases that are different with regard to their binding function to a complementary base.

The terms "upstream" and "downstream" indicate the relative location resp. direction within a nucleid acid strand. Looked upon from a reference element, "upstream" refers to a location or direction towards the 5'-end, "downstream" towards the 3'-end.

The term "adaptor" refers to a partly double-stranded nucleic acid preferably composed of a oligonucleotide and a second, shorter oligonucleotide. The shorter of the two oligonucleotides is complementary to the longer and hybridized to its 5'or 3'-end, thus forming the double-stranded piece of nucleic acid. The rest of the longer oligonucleotide is single-stranded with a hybridization sequence at its other end [a sequence complementary to a particular nucleic acid] by which it can be hybridized to a defined nucleic acid (see under "hybridization sequence").

Enzymes and Enzymatic Activities

The term "reverse transcriptase" (abbreviation "RT") refers to an enzyme which in its natural function, in a primer-dependent reaction and by using dNTPs, synthesizes a DNA complementary to a template RNA.

The term "reverse transcriptase activity" (abbreviation "RT activity") refers to the activity of any enzyme by which in a primer-dependent reaction and by using dNTPs a DNA complementary to a template RNA is synthesized.

The term "RNA polymerase", or "DNA-dependent RNA polymerase" refers to an enzyme which in sequence-specific manner binds to a transcription promoter, initiates the transcription of a RNA starting from a defined position downstream of this transcription promoter, and which, from a single-stranded or double-stranded DNA and by using rNTPs, synthesizes a RNA complementary to the transcribed DNA strand.

The term "DNA polymerase" or "DNA-dependent DNA polymerase" refers to an enzyme which, in a primer-dependent reaction and by using dNTPs, synthesizes a DNA strand complementary to a DNA strand.

The term "RNA replicase" refers to an enzyme or complex of enzymes with RNA-dependent RNA polymerase activity capable of replicating, by using rNTPs, a replicative RNA matched to the RNA replicase, the result of the replication process being a new molecule of replicative RNA which is complementary to the replicated replicative RNA.

The term "DNA replicase" refers to an enzyme or complex of enzymes which, in a protein-primed process that starts from a DNA-ori, initiates the replication of a replicative DNA matched to the DNA replicase, whereby dNTPs are used, and which, due to its DNA-dependent DNA polymerase activity effects the replication of the replicative DNA. During the replication process the DNA replicase displaces the pre-existing DNA strand complementary to the replicated DNA strand.

Functional Sequences and Functions

The term "functional sequence" refers to a segment on the strand of a nucleic acid that exerts a certain function in the (PERT) assay. This function is exerted by the nucleic acid by which the functional sequence is introduced, and/or by a subsequent single-stranded nucleic acid derived thereof that has an identical or complementary base sequence, or by a double-stranded nucleic acid. The base sequence contained in a functional sequence is either precisely defined by its function or can be chosen freely.

The term "hybridization sequence" refers to a functional sequence that, for the purpose of hybridization to another nucleic acid, has a base sequence complementary to the hybridization sequence of the other nucleic acid.

The term "flanking sequence" refers to a functional sequence that forms the 5' or 3'-end of a nucleic acid either upstream or downstream of any other functional sequence.

The term "spacer sequence" refers to a functional sequence that serves the function of separating two other functional sequences on a nucleic acid from each other.

The term "transcription promoter sequence" refers to a functional sequence with a defined base sequence that is associated to the function of a transcription promoter. The "P(+) sequence" of a transcription promoter refers to the base sequence on the DNA strand complementary to the synthesized RNA. The "P(−) sequence" of a transcription promoter consists of the base sequence of the DNA strand that has the same polarity as the synthesized RNA.

The term "transcription promoter" refers to the double-stranded DNA segment consisting of the complementary P(−) and P(+) transcription promoter sequences that, by binding a sequence specific RNA polymerase, initiates the synthesis of a RNA in a direction defined by the orientation of the base sequence. In all cases in which the DNA to be transcribed is single-stranded the transcription promoter also includes at least the first three nucleotides of the DNA to be transcribed in the form of a double-stranded DNA.

The term "replicase binding domain" refers to a functional sequence that by means of secondary structures within a single-stranded RNA effects the binding of a RNA replicase that matches the replicase binding domain.

The term "RNA-ori sequence" refers to a functional sequence with a defined base sequence on a nucleic acid strand which, when located at the 3'-end of a single-stranded RNA, allows the initiation of RNA replication by means of a RNA replicase which matches the RNA-ori sequence and has been bound to the RNA.

The term "5'-RNA-ori sequence" refers to the RNA-ori sequence which is or will be located at the 5'-end of the replicative RNA.

The term "3'-RNA-ori- sequence" refers to a RNA-ori sequence which is or will be located at the 3'-end of a replicative RNA.

The term "RNA-ori(+) sequence" refers to the base sequence at the polarity which, when located at the 3'-end of an RNA, allows replication of the RNA.

The term "RNA-ori(−) sequence" refers to a base sequence complementary to the RNA-ori(+) sequence.

The term "DNA-ori sequence" refers to a functional sequence with a defined base sequence on a nucleic acid strand that is associated to the initiation of DNA replication in a DNA replication system. The term "DNA-ori(+) sequence" refers to that base sequence which, at the replication of the DNA, is complemented first. The "DNA-ori(−) sequence" refers to the base sequence complementary to the "DNA-ori(+) sequence".

The term "DNA-ori" refers to the double-stranded DNA segment consisting of the complementary DNA-ori(+) and DNA-ori (−) sequences. Located at the end of a double-stranded DNA, this segment, by binding certain cofactors [proteins], initiates replication by a DNA replicase in an in vitro replication system that corresponds to the DNA-ori. A "DNA-ori" may also be formed by DNA-ori(+) and DNA-ori(−) sequences of a single strand of replicative DNA hybridized to each other.

Nucleic Acids with Defined Function

The term "primer" refers to a nucleic acid of a sequence that is complementary to another nucleic acid. When hybridized to that nucleic acid the primer, by means of its free 3'-hydroxy group, serves as the point at which the synthesis of a nucleic acid strand by an RT activity or a DNA-dependent DNA polymerase is initiated.

The term "RT primer" refers to the primer that exerts the function of a primer for the RT activity.

The term "template nucleic acid" refers to the single-stranded nucleic acid to which, at least in part, a complementary DNA strand is synthesized by reverse transcriptase activity.

The term "template RNA" refers to those parts of a template nucleic acid that consist of RNA and to which, at least in part, a cDNA is synthesized.

The term "template DNA" refers to those parts of a template nucleic acid that consist of DNA.

The term "template-primer combination" refers to the combination of a template nucleic acid with all nucleic acids hybridized to it, including RT primers, that is used as substrate for the [RT or] RT activity.

The term "cDNA" refers to the nucleic acid that consists of the DNA complementary to the template nucleic acid that has been synthesized by the RT activity, as well as all components of the RT primer.

The term "cDNA/template duplex" refers to a at least in part double-stranded nucleic acid which consists of the template nucleic acid and the cDNA hybridized to it.

The term "cDNA/RNA heteroduplex" refers to those segments of a cDNA-template duplex that consist of the template RNA and the cDNA hybridized to it.

The term "replicative RNA" refers to a single-stranded RNA that contains all functional sequences required for replication by means of an in vitro RNA replication system matched to this RNA and is replicated in this system.

The term "primary replicative RNA" refers to the replicative RNA which in step 1 is generated as the nucleic acid to be amplified.

The term "replicative DNA" refers to a single-stranded or at least partially double-stranded DNA replicated in an in vitro DNA replication system matched to the replicative DNA. A DNA-ori sequence is located at both ends of the replicated DNA strand; either these form a DNA-ori within a single-stranded DNA, or an active DNA-ori is found at least at one end of the partially double-stranded DNA.

The term "primary replicative DNA" refers to the replicative DNA generated in step 1 as the nucleic acid to be amplified.

The term "reporter probe" refers to a nucleic acid different from, but directly or indirectly linked to, the cDNA, which is used to demonstrate that synthesis of a cDNA has taken place. The reporter probe either contains the nucleic acid to be amplified or is the educt of a reaction or reaction sequence leading to the nucleic acid to be amplified.

Varia

The term "retroelement" refers to genetic elements and their expression products which have been generated by reverse transcriptase activity and/or replicate themselves by means of reverse transcriptase.

The term "carrier" refers to a solid phase consisting, e.g., of beads, the surface of a well of a microtiter plate, or a filter membrane.

FIG. 1 shows the PERT assay which consists of three consecutive steps. In the first step, a nucleic acid to be amplified is provided by means of the RT activity present in the sample. In the second step, this [nucleic acid to be amplified] is amplified by means of a suitable nucleic acid amplification system, and in a third step, a suitable method is used to analyze and identify the amplified nucleic acid.

In the FIRST STEP the sample is brought into a condition suitable for the detection of RT activity. A template nucleic acid is chosen in combination with at least one suitable RT primer as substrate for the RT activity that may be present in the sample, and in combination with the other reagents needed for the synthesis of cDNA, such as the different deoxyribonucleoside triphosphates (dNTPs), divalent cations ($Mg^{++}$ or $Mn^{++}$), a suitable buffer system and other substances providing maximum support to the specific synthesis of cDNA. As a first result of the RT activity a cDNA complementary to the chosen template nucleic acid is synthesized. This cDNA is bound to the template nucleic acid, thus forming a cDNA-template duplex, which is at least in part a cDNA-RNA heteroduplex, and is present in a nucleic acid mixture consisting of unreacted template-primer combinations, unbound primer molecules and non-primed template molecules.

There are various possibilities for providing the nucleic acid to be amplified. In some variants of the PERT assay the nucleic acid to be amplified is identical with the cDNA or is a component of it. In other cases the cDNA, respectively its components, present in the nucleic acid mixture is the educt of a reaction or a chain of reactions which produce the nuclic acid to be amplified. It is also possible to effect, by means of components of the cDNA, the selection of a nucleic acid that either is a reporter probe or provides the link to a reporter probe. In this case the reporter probe represents or contains the nucleic acid to be amplified or it is the educt of a reaction or chain of reactions that result in the nucleic acid to be amplified, if need be by including other nucleic acids. Finally it is possible to use not only the cDNA but the cDNA-template duplex for providing the nucleic acid to be amplified. In this case the cDNA-template duplex either is resp. contains the nucleic acid to be amplified, or it, resp. a segment of it, is the educt of a reaction or chain of reactions that result in the nucleic acid to be amplified. The first step also includes appropriate measures for the elimination of nucleic acids that are amplifiable but not to be amplified.

In the SECOND STEP the product of the first step, i.e. the nucleic acid to be amplified, is amplified to high quantities by means of a suitable nucleic acid amplification procedure. Dependent on the amplification procedure employed the product consists of either a defined DNA and/or a defined RNA.

In the THIRD STEP of the PERT assay the amplified nucleic acid is identified and, if need be, quantified. Any technique suitable for the identification, possible quantification or detection of the synthesis of a certain nucleic acid sequence can be applied. Every trained, experienced molecular biologist is familiar with a number of such techniques. By combining the first two steps, it becomes possible in step 3 to identifiy even minimum quantities of RT activity, in borderline cases even the minimal dosis needed to synthesize a single molecule of cDNA.

In the following general aspects of the different steps of the PERT assay are described in detail.

Materials and Sample Pretreatment

The method chosen for sample pretreatment depends on its composition and on the types of retroelement-associated RT activity that are or are not to be included in the PERT assay. Therefore the method chosen determines, to a certain degree, the specificity and the sensitivity of the PERT assay. It does not usually determine, however, which variant of the PERT assay ought to be chosen.

In the wider sense the sample consists at least in parts of biological material. This may be of human, animal or vegetable origin and includes both pro- and eucaryotic cells. We quote the following examples for illustration:

Body tissues or organs of human or animal origin, inclusive of
  (a) fluid tissues such as blood or blood fractions, e.g. serum, plasma, certain blood cell populations or fractions, plasma or serum fractions, blood products as e.g. blood proteins, coagulation factors, hyperimmune serum, antibody concentrates, hormones etc.
  (b) firm tissues and organs such as transplantates, biopsy or autopsy material, smears taken from mucous membrane and other surfaces, single cells or preparations or extracts such as hormone preparations from glandular tissue, placenta etc., meat and meat products from domestic animals
  (c) body fluids or excretions, both physiological and pathological, e.g. cerebrospinal fluid, urine, saliva, bile, sweat, milk, other glandular secretions, blister contents, amniotic fluid, synovial fluid, chamber fluids ascites or other effusions into body cavities, lymph, stools, etc., or products containing such materials.
  (d) samples of in vitro propagated pro- and eurocaryotic cell cultures of any kind as well as biological products made of such, e.g. vaccines, antibodies, growth and differenciation factors, hormones, recombinant proteines etc.
  (e) various materials, e.g. samples of food, water and other beverages, environmental samples, hygiene samples, samples from useful plants (vegetable, fruit, wood, fiber plants)

In general the sample pretreatment serves to get the RT activity in the sample into a form that allows to catalyze the RT reaction. Wherever the RT activity in the sample is enclosed in cells, cell organells or virus particles, the enzyme must first be extracted by means of suitable procedures.

For maximum specificity in the detection of e.g. retroviral RT contamination by cellular DNA polymerases is to be avoided. Various measures may be used to pretreat the sample accordingly. On the one side there are physical measures such as centrifugation under conditions pelleting pro- and eucaryotic cells but not viruses or dissolved enzyme, or ultrafiltration that holds back cells but not virus particles or dissolved enzyme. Another example is the enrichment of virus particles in one of the phases of a suitable two phase system. On the other side there are immunological methods that lend themselves to direct the specificity or the sensitivity of the PERT (assay) as desired. For example intact virus particles of a specific type or components thereof or free enzyme may be enriched in the sample through immune adsorption or precipitation by means of suitable antibodies. Immune reagents may be used to this purpose, as may be lectines with an affinity for certain glycoproteines as well as other agents with an affinity to retroelements or their components or other agents. A further example is PolyU, which has an affinity for RT. Using such methods it is also possible to remove unwelcome activities from the sample.

Frequently the sample will consist of human or animal blood samples, especially their fluid components, plasma and serum. In this case the sample preparation may consist of one or more of the following steps:

(a) high speed centrifugation, e.g. 15'000x g, for the elimination of cells, cell detritus or other unwelcome particulate material (b) ultrafiltration with filters of suitable pore size for the further elimination of unwelcome particulate material (c) ultracentifugation for the pelleting of virus particles or for the adsorption of virus particles to a solid phase coated with antibodies or other suitable molecules or to another suitable carrier, or precipitation by means of immune reagents or chemical substances (e.g. polyethyleneglycol)

(d) extraction of the RT activity by means of a buffer containing a suitable detergent or other chemical or physical procedures protective of the enzyme Further sample materials to be used according to this procedure include all fluid materials or any that can be dissolved or suspended in a fluid, e.g. any kind of powder (e.g. lyophilized products).

Nucleic Acids Employed

FUNCTIONAL SEQUENCES: all nucleic acids used in the assay are composed of functional sequences. In FIGS. 2–23 these are shown by means of bars with different patterning. The area of hybridization between two nucleic acids is marked by vertical hatching. The length of these bars is usually identical, but this does not mean that the functional sequences they represent must have the same length. A shorter or longer bar does not indicate any difference of length in the sequences it symbolizes; such variations merely serve to improve the clarity of the figure. If not marked otherwise, each functional sequence has a specific base sequence different from the other functional sequences. If not marked otherwise, each functional sequence correlates to one function only. Where exceptions occur they are indicated either in the figure description or under "Modifications". Furthermore, a given function may or may not be necessary for the variants of the PERT assay described below to be functionable. All nucleic acids used consist of at least one hybridization sequence.

FUNCTIONAL GROUPS: The nucleic acids used in the assay often carry functional groups marked (R1), (R2), etc., in the figures. These are preferentially located at the 5'-end; to simplify matters only this position has been indicated in the figures. Within the bounds of technical possibility and as long as there is no interference with the function and reaction course of the PERT assay, these functional groups allow for a wide variety of additional characteristics. E.g. (R) is a ligand, for example a biotin molecule capable of binding the nucleic acid carrying (R) to a carrier coated with avidin. Other examples for ligands are molecules with antigenic properties that can bind appropriate carrier-immobilized specific antibodies. (R) may also be a carrier itself; in this case the nucleic acid carrying (R) is bound covalently to a carrier. It is preferable never to have more than one (R) carrier. Alternatively the nucleic acids may also be labeled with (R) by using dNTPs or rNTPs with functional groups for the synthesis.

TEMPLATE-PRIMER COMBINATION: This consists of template nucleic acid and all nucleic acids hybridized to this. All template-primer combinations used for the PERT assay contain a heteropolymeric template nucleic acid. A segment of this, preferably immediately next to the 5'-end of a hybridization sequence for a RT primer, consists of RNA and is referred to as "template RNA". The template RNA is the real substrate of an RT or an RT activity; the synthesis of a DNA strand complementary to a template RNA defines the presence of a RT or RT activity in the reaction mixture. In most variants of the PERT assay the template nucleic acid consist entirely of RNA of natural, recombinant or of synthetical provenience. In some variants, however, certain functional sequences of template nucleic acid located upstream of the template RNA are presented in the form of DNA. These DNA components of template nucleic acid make up the "template DNA". At least one RT primer is bound to the template nucleic acid, which RT primer is at least at its 3'-end hybridized to the template nucleic acid. In addition to the RT primer another single or partly double-stranded nucleic acid, preferably a DNA, may be hybridized to a hybridization sequence located towards the 5'-end of the template nucleic acid. This is used for the introduction of a functional sequence essential to the assay. After completion of the RT reaction this DNA is bound to the cDNA synthesized in the RT reaction by means of a DNA ligase (e.g. T4 DNA ligase). Components of the template nucleic acid downstream of the hybridization sequence located farthest downstream, i.e. of the minimally required hybridization sequence for the RT primer, may consist of RNA and/or DNA.

The template-primer combination is chosen so that the PERT assay guarantees the maximum specificity and sensitivity for the detection of the retroelements to be detected. It is absolutely necessary to make sure that a nucleic acid amplification process is initiated only if in step 1 a piece of template RNA of sufficient length has been reversely transcribed. Furthermore care must be taken to prevent, in step 2, the initiation of an amplification process, by a nucleic acid in the sample (RNA and/or DNA), which is independent of the cDNA synthesized in step 1. It is of utmost importance for the specificity and the sensitivity that the template nucleic acid is neither identical nor partially identical to any of the nucleic acids present in the sample, whether these may be part of the normal genome of a species or a nucleic acid of an infectious agent or another contaminating nucleic acid whose presence in the sample cannot be excluded. In order to reach a maximum of specificity for the retroviral RT test a heteropolymeric template RNA is preferred. In addition, the efficiency of cDNA synthesis by the various types of enzymes with RT activity may be influenced, above all by means of the length and secondary structure of the template RNA, thus allowing a regulation of the sensitivity and the specificity of the PERT assay.

In addition to the one hybridization sequence that is the minimum requirement, most template nucleic acids possess at least one more hybridization sequence. These serve to anneal the nucleic acids needed for the priming of the RT reaction and/or the introduction of essential functional sequences. When using reporter probes and whenever the hybridization sequence is exclusively used for the selection of the reporter probe, the template nucleic acid may contain several subsequent hybridization sequences, preferably separated from each other by a short spacer sequence. It thus becomes possible to hybridize several reporter probe molecules to one molecule of the cDNA, thus increasing the sensitivity. If more than one hybridization sequence is used for reporter probes these may also have different base sequences; thus it becomes possible to use different reporter probes. It is also possible to place more than one hybridization sequence on the template nucleic acid for the RT primer. According to the respective variant of the PERT assay the template nucleic acid may or must contain other functional sequences apart from the hybridization sequences.

As mentioned above it may be of advantage to use a template nucleic acid composed of both RNA and DNA sequences. This possibility is recommendable if the nucleic acid to be amplified needs a DNA that is at least partially double-stranded or if the synthesis of the nucleic acid to be amplified resp. the initiation of the amplification procedure needs a DNA that is at least partially double-stranded. This is the case if step 2 uses a nucleic acid amplification procedure based on the usage of replicative nucleic acids or on transcription and if a double-stranded DNA-ori resp. a transcription promoter is needed. When constructing the template nucleic acids for such procedures care must be taken that a sufficiently long and adequately shaped template RNA is placed between the template DNA and the hybridization sequence for the RT primer, so that the cDNA synthesis can only be initiated by the effect of RT activity. The reverse transcription of the template RNA is followed by the duplication of the template DNA. At this point it may be of advantage to supplement the weak DNA-dependent DNA polymerase activity of the RT present in the sample by adding a DNA-dependent polymerase that does not possess any RT activity.

When using replicative nucleic acids in step 2, a template nucleic acid consisting of DNA/RNA only needs a single hybridization sequence, namely that for the RT primer. Examples of template nucleic acids containing RNA and DNA are given in the descriptions of the figures.

RT PRIMER: All RT primers used in the assay are nucleic acids consisting of either RNA, DNA, or a combination of these that are either single-stranded or partially double-stranded. They consist of at least one hybridization sequence by which they hybridize to the template nucleic acid. In certain cases one or more sequences that are not complementary to the template nucleic acid may be located upstream of the 3'-end hybridization sequence. The natural tRNA used as RT primer in the replication cycle of retroviruses is an example for this kind of bipartite RT primer. If the RT primer is a DNA the non-complementary sequences may be used for the introduction of new functional sequences not yet existent in the template nucleic acid. A further nucleic acid may be hybridized to the non-complementary 5'-end of the RT primer. This part of the RT primer will then be double-stranded. The length and structure of the non-complementary primer sequences may be chosen freely as long as they do not interfere unduely with the optimal progress of the PERT assay. The RT primer may also carry a functional group (R1).

NUCLEIC ACIDS FOR THE PRODUCTION OF dsDNA: In many variants of the PERT assay it is necessary to produce, after the synthesis of cDNA, a second DNA strand at least partially complementary to the cDNA. Therefore at least one other nucleic acid, preferably a DNA oligonucleotide, must be hybridized to the cDNA. This type of DNA consists of at least one hybridization sequence. In certain cases at least one more functional sequence that is not complementary to the cDNA is added. On the second DNA strand this additional sequence will be located in terminal position with regard to the hybridization sequence and thus be equivalent to a flanking sequence. If these non-complementary sequences consist of DNA, they can be used for the introduction of either additional functional sequences needed but not yet present in the cDNA or other desired functions. The length and structure of these sequences may be chosen freely as long as they do not interfere unduely with the optimal course of the PERT assay. These nucleic acids may also carry a functional group (R).

REPORTER PROBES: These nucleic acids are used to demonstrate that a cDNA has been synthesized by binding them directly or indirectly to the cDNA by means of hybridization. This binding may either be effected by directly hybridizing a hybridization sequence of the reporter probe to the hybridization sequence of the cDNA. In this case the reporter probe is different from the template nucleic acid with the exception of that sequence that is used for the hybridization to the cDNA. However, it is also possible to bind the reporter probe to the cDNA indirectly by interposing at least one other nucleic acid between the reporter probe and the cDNA, which is hybridized to both. In this case the sequence of the reporter probe is preferably entirely different from the sequence of the template nucleic acid. The reporter probe either represents or contains the nucleic acid to be amplified, or it or a part of it is the educt of a further reaction or chain of reactions yielding the nucleic acid to be amplified.

General Aspects for the Procedure in Step 1

PROVIDING THE NUCLEIC ACID TO BE AMPLIFIED: In step 1 the RT activity converts a set of functional sequences adequately combined by means of the template-primer combination to a cDNA also containing these functional sequences; this cDNA is linked to the template nucleic acid to form the cDNA-template duplex. If this does not yet contain all the functional sequences needed for the nucleic acid to be amplified and its synthesis in the required constellation (RNA or DNA, single- or double-stranded), the missing functional sequences must be introduced by means of further nucleic acids resp. reactions and must then, together with the existent functional sequences, be put together to the nucleic acid to be amplified.

One method of INTRODUCING THE FUNCTIONAL SEQUENCES needed for the production and the amplification of the nucleic acid to be amplified is the choice of a template nucleic acid that already contains all functional sequences; in this case the RT primer and the reaction conditions are chosen so that the cDNA resp. the cDNA-template duplex also contain these functional sequences. cDNA resp. cDNA-template duplex may then represent or contain the nucleic acid to be amplified. On the other side it is possible to start from a template nucleic acid that does not contain all functional sequences needed for the production and the amplification of the nucleic acid to be amplified; in this case the missing functional sequences must be added by means of other nucleic acids. This may be achieved, e.g., by means of the RT primer, other DNA molecules hybridized to the template nucleic acid that, after the RT reaction has been effected, are ligated to the synthesized cDNA, a primer for the synthesis of a dsDNA hybridized to the cDNA, or other nucleic acids of which at least one is hybridized to the hybridization sequence placed farthest downstream in the cDNA. These latter nucleic acids include reporter probes or nucleic acids effecting the specific connection between the cDNA and a reporter probe.

REACTION CONDITIONS FOR THE RT REACTION: It is essential for the sensitivity of the PERT assay to ensure optimal reaction conditions for the RT activity that is to be detected with regard to pH, salt concentration, ionic strength, type and concentration of the divalent cation used (Mg, Mn), concentration of the dNTPs used as well as reaction temperature. Furthermore it is important to ensure the functional integrity of the template-primer combination throughout the RT reaction.

SYNTHESIS AND COMPOSITION OF THE CDNA: At its 5'-end the cDNA consists of the RT primer. The 3'-end is formed by the sequence synthesized in the RT reaction. If the template nucleic acid includes a template DNA in addition to the template RNA, the cDNA consists of the RT primer at its 5'-end, of the piece complementary to the template RNA in the middle, and of a part that is complementary to at least the 3'-end of the template DNA at its 3'-end. Those nucleic acids initially hybridized to the template nucleic acid are not part of the cDNA though; these are only ligated to the cDNA in a further reaction.

ELIMINATION OF THE TEMPLATE NUCLEIC ACID: In certain variants of the PERT assay it is advantageous or necessary to eliminate the template nucleic acid from the subsequent reactions after the RT reaction has been completed. Measures to be used include e.g. the total degradation of the RNA contained in the reaction mixture by means of enzymatic treatment, e.g. by means of RNase or by chemical treatment (e.g. basic hydrolysis), however without thereby eliminating the cDNA molecule. The degradation of the RNA also destroys the function of the template nucleic acid since it necessarily contains a template RNA. In all variants of the PERT assay it is also possible to bind the RT primer by its 5'-end to a carrier, e.g. by means of a functional group (R1). The cDNA synthesized by the RT activity is consequently also bound to the carrier. Thus it becomes generally possible to eliminate the template nucleic acid by denaturation and subsequently washing it away, thus preventing its interference in subsequent reactions. If washing is not sufficient, the RNA parts of the template nucleic acid may also be destroyed by means of basic hydrolysis and removed by aspiration; after washing with a suitable neutral buffer the reagents needed in the later reactions are added in a suitable buffer.

It will be plain to any experienced molecular biologist that there is, by applying the principles described here and subsequently and by using suitable combination, a wide variety of possibilities for the application of a PERT assay that corresponds to the guidelines of the invention. In all cases it is essential to match all nucleic acids used in the procedure as well as their functional sequences and functional groups and all further reagents and the chosen reaction conditions with each other and the sample in a way that guarantees the necessary specificity and sensitivity of the assay.

Procedure of the Pert Assay by Using PCR in Step 2

Figure 2:
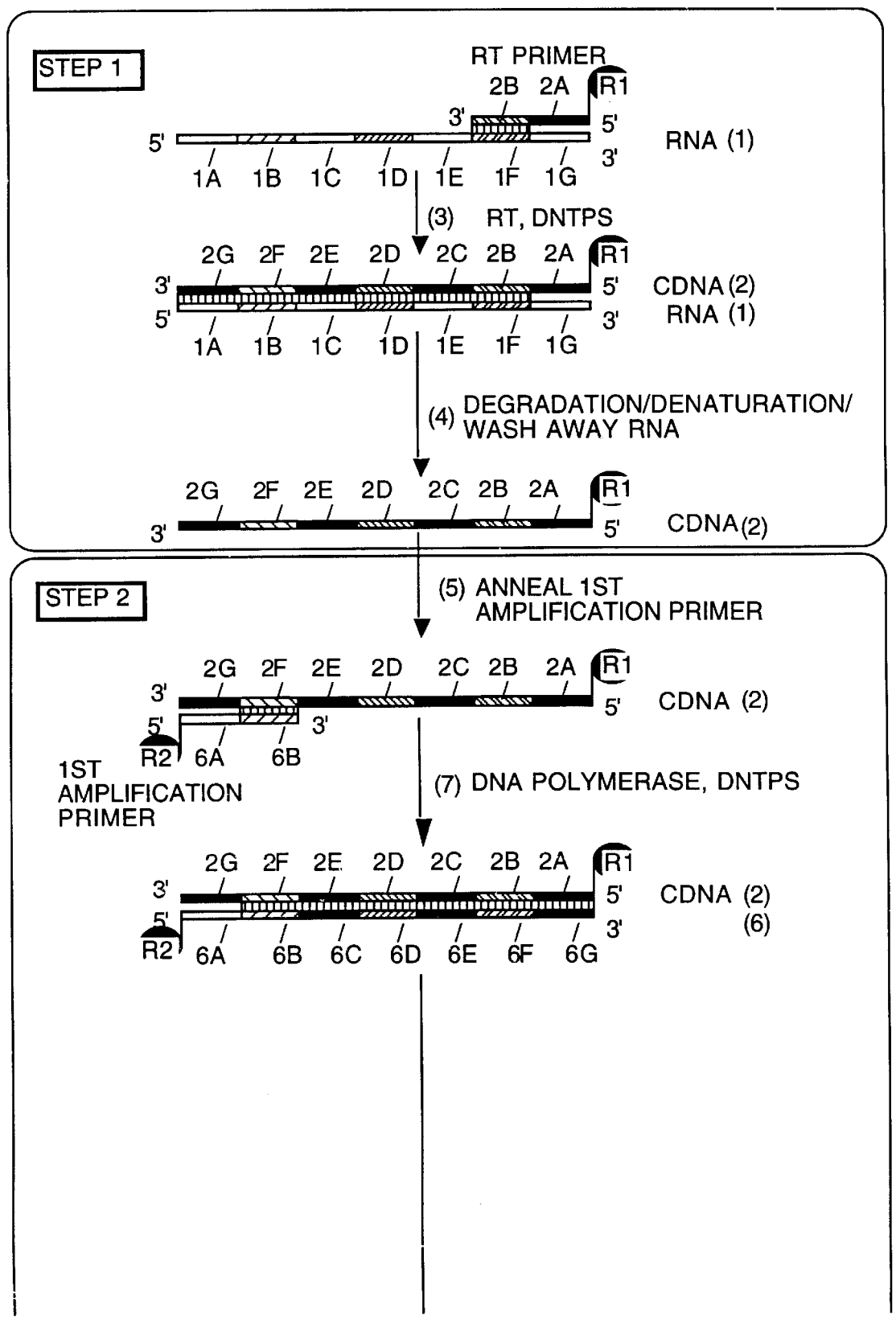
FIG. 2 shows the structure of the PERT assay for an illustrative variant, in which the nucleic acid to be amplified consists of a sequence of the cDNA, which sequence is amplified by means of the polymerase chain reaction.
Figure 2:
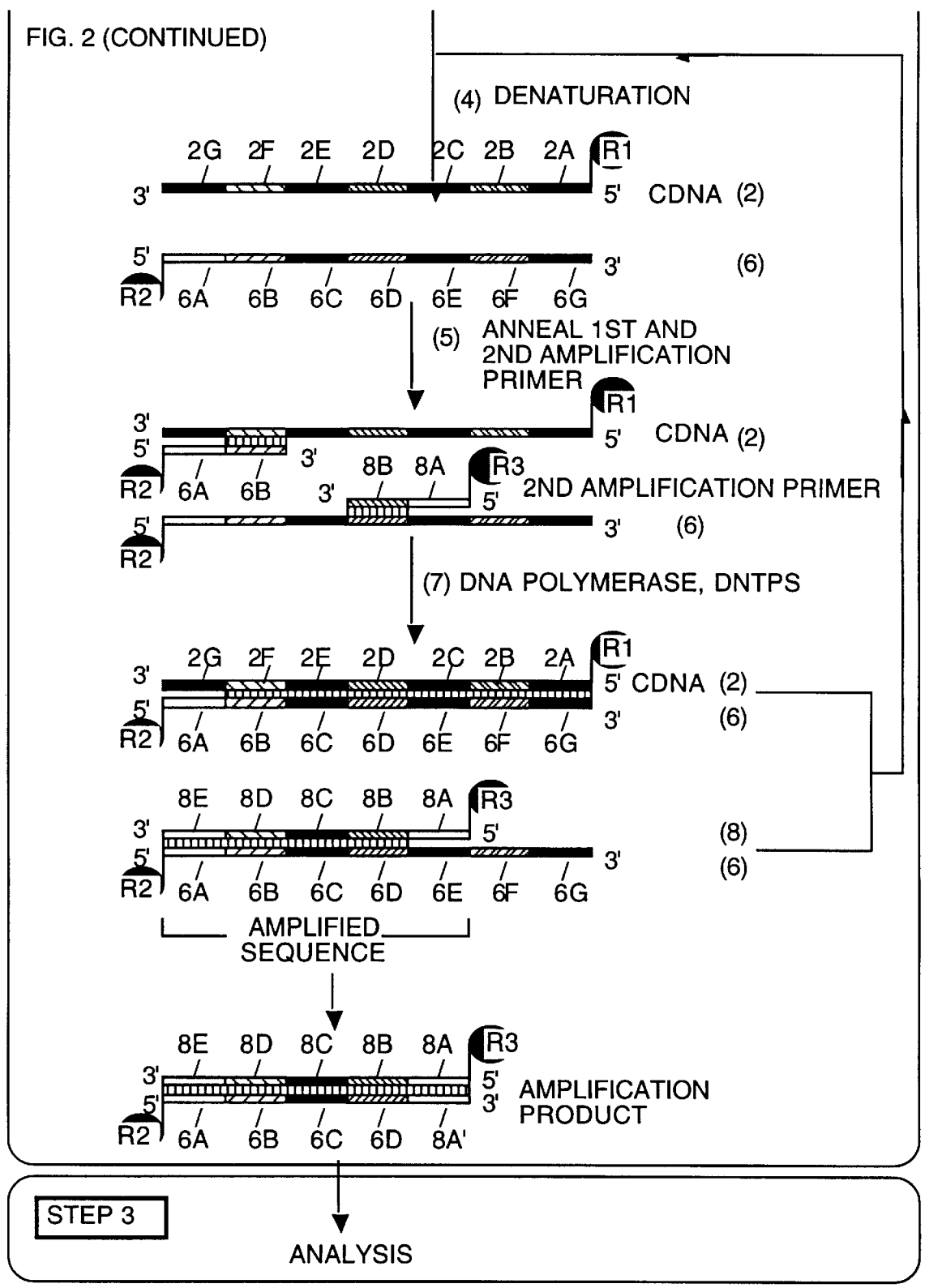
Figure 3:
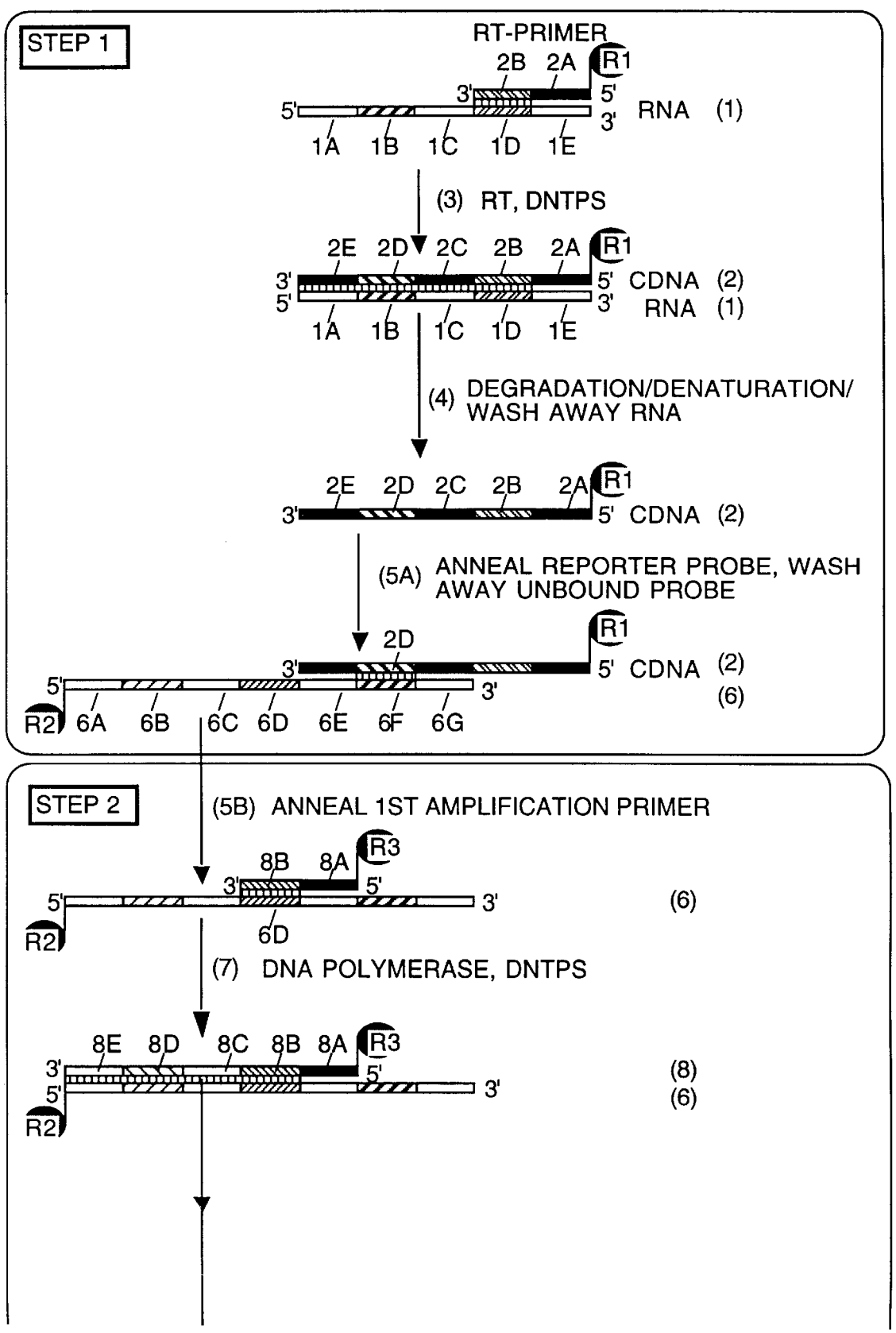
FIG. 3 shows the structure of the PERT assay for an illustrative variant, in which the nucleic acid to be amplified is a sequence of a reporter probe, which sequence is amplified by means of polymerase chain reaction.

FIGS. 2 and 3 show variants of the PERT assay based on the use of polymerase chain reaction in step 2. It is preferable to use a pure RNA as the template nucleic acid in this case. On principle there are two ways of detecting the cDNA synthesized by RT activity sensitively, that is by means of an amplification process: on the one hand the cDNA, resp. at least a piece thereof, can be amplified directly. This principle is illustrated in FIG. 2. On the other hand a piece of a DNA reporter probe bound specifically, that is by means of hybridization, to the cDNA may be amplified in place of the cDNA (FIG. 3). In both cases only three kinds of functional sequences are used: hybridization, spacer and flanking sequences.

FIG. 2 shows a variant in which a piece of the cDNA is the nucleic acid to be amplified. Step 1: A template nucleic acid containing the functional sequences (1a) (1b) (1c) (1d) (1e) (1f) (1g) is used. Of these (1b), (1d) and (1f) are hybridization sequences and necessary. (1c) and (1e) are spacer sequences and not necessary; however the presence of (1c) is to be preferred. The flanking sequences (1a) and (1g) are not necessary. Of the three hybidization sequences (1f) is used for the annealing of the RT primer. (1b) and (1d) are used in step 2 for the annealing of the primers needed for the amplification of the product of the RT reaction (amplification primers). The sequence of (1b) is used for the annealing of the first amplification primer, the sequence of (1d) for the annealing of the second amplification primer. The RT primer (R1) (2a) (2b) will preferably be an oligonucleotide. (2b), which is located at its 3'-end and necessary, serves to anneal to (1f) of the template nucleic acid. (2a), which is located at the 5'-end and non-complementary, is not necessary and serves the purpose of adding any further desired functions to the cDNA. If RT activity is present in the pretreated sample a cDNA (2) is synthesized in reaction (3) by use of the required dNTPs; maximally, this cDNA contains elements (R1) (2a) (2b) (2c) (2d) (2e) (2f) (2g). At least the functional sequences up to and including (2f) must be synthesized in the RT reaction for the PERT assay to operate. This cDNA contains the nucleic acid to be amplified by means of the PCR.

Suitable measures need to be taken now to ensure that the amplification in step 2 starts exclusively from the cDNA (2) that has been synthesized in the RT reaction, but not from the template nucleic acid (1) consisting of RNA. The latter can happen e.g. if the DNA-dependent DNA polymerase used in step 2 also exhibits a certain RNA-dependent DNA polymerase activity or if the enzyme preparation used is contaminated by an enzyme with such activity. If the DNA amplification procedure used in step 2 ensures that no RNA molecule at all is transcribed to cDNA, or if, should RNA molecules indeed be transcribed to cDNA, the sensitivity of the PERT assay is not sufficient to detect this nonspecific activity under the conditions chosen, such methods can be dispensed with. However, it is generally important to ensure that in the subsequent reactions the excessive quantities of the template nucleic acid (1) do not saturate the amplification primers and thereby prevent an efficient amplification of the DNA sequences, since this will lead to false-negative results. It is therefore preferable to eliminate the existing template nucleic acid (1) as a participant in subsequent reactions in reaction (4) by means of one of the measures already mentioned. The single-stranded cDNA (2) is the product of step 1.

Step 2: Subsequently, in reaction (5), the first amplification primer (R2) (6a) (6b), preferably a DNA oligonucleotide, is hybridized to the cDNA (2). Preferably (R2) is different from (R1). (6b), located at the 3'-end of the primer and necessary, effects the hybridization to (2f) of the cDNA. (6a), located at the 5'-end and not necessary, is non-complementary to the cDNA. After addition of a DNA-dependent DNA polymerase a dsDNA (2)//(6) is synthesized in reaction (7) by using dNTPs.

In reaction (4) this dsDNA is denatured. This is then followed in reaction (5) by a further annealing of the first amplification primer (R2) (6a) (6b) as well as a first annealing of the second amplification primer (R3) (8a) (8b) to the corresponding DNA strand. The second amplification primer again is preferably a DNA oligo nucleotide that is not complementary to the first amplification primer. (R3) too is preferably different from (R1). The obligatory (8b) located at the 3'-end of the primer is used for the hybridization to (6d) of the second DNA strand. The facultative (8a) located at the 5'-end is not homologous to the cDNA. By using dNTPs the dsDNA (2)//(6) resp. (6)//(8) are synthesized by the DNA-dependent DNA polymerase in reaction (7). These are introduced into the following amplification cycle. The main result of the amplification process is a dsDNA consisting of the elements (R2) (6a) (6b) (6c) (6d) (8a') on one strand, and of (R3) (8a) (8b) (8c) (8d) (8e) on the other strand.

Step 3: This dsDNA may be subjected to the analysis in accordance to the general remarks concerning step 3 in the following. Alternatively the functional groups (R) can be used as labels, thus providing simple systems for the detection of dsDNA molecules carrying two of these labels, preferably (R2) and (R3). Such detection systems may be based on ELISA, but also on particle agglutination, a cheap and simple system.

Modifications

All functional sequences and functional groups in the template nucleic acid and in the primers that have been identified as facultative may be dispensed with, whether individually or in the different combinations possible. If (6a) and (8a) are dropped in the amplification primers the amplification product is a double-stranded DNA consisting of sequences (6b) (6c) (6d)//(8b) (8c) (8d).

For the template nucleic acid (1) the flanking sequences (1a) and (1g) may have any function, the only restriction being that they do not interfere unduly with an optimal course of the PERT assay. Provided this is not the case it is possible to use naturally occurring RNA molecules as template nucleic acid (1).

Diverging from the norm, a functional sequence may in certain situations serve more than one function. For instance the hybridization functions of (1d) and (1f) may be joined. In this case the (1d) sequence will mediate the annealing of an RT primer (R3) (8a) (8b) to the template nucleic acid (1) in step 1, while in step 2 sequence (6d) derived from (1d) will mediate the annealing of the 2nd amplification primer (R3) (8a) (8b). In this case the functional sequences (1e) and (1f) of the template nucleic acid (1), the functional sequences derived from these, as well as the separate RT primer (R1) (2a) (2b) will be dropped. A further possible modification is to place these hybridization functions so that sequences (1d) and (1f) involved will partly overlap. In this case the spacer sequence (1e) and the sequences derived from this will be dropped.

Furthermore, by using different sequences for the annealing of the RT primer and the 2nd amplification primer it becomes possible to use RNA in the RT primer; thus the sensitivity and/or the specificity of the PERT assay may be influenced.

A further alternative diverging from the norm is to use identical base sequences for different functional sequences, these base sequences may also be homopolymeric. This applies to the flanking sequences (1a) and (1g) as well as the spacer sequences (1c) and (1e) of the template nucleic acid (1), which may be homopolymeric and/or identical to each other.

Finally it is possible to arrange several hybridization sequences for the RT primer on a template nucleic acid.

FIG. 3 illustrates the use of a reporter probe.

Step 1: If instead of the cDNA a reporter probe is used for amplification the template nucleic acid need not contain all functional sequences listed in FIG. 2. In this case a template nucleic acid containing the functional sequences (1a) (1b) (1c) (1d) (1e) is used. (1d) is used for binding the RT primer and is obligatory; (1c) takes the function of a spacer and is facultative. The hybridization sequence (1b) is necessary; the cDNA sequence (2d) derived from this serves to bind the reporter probe. (1a) and (1e) are facultative flanking sequences.

The template nucleic acid is bound to the RT primer (R1) (2a) (2b) by means of the hybridization sequence (1d). Specifications for this RT primer have been given in FIG. 2/step 1. In the presence of RT activity in the pretreated sample, the cDNA (2) is synthesized in reaction (3) by incorporating the necessary dNTPs (2); this cDNA as a maximum contains the elements (R1) (2a) (2b) (2c) (2d) (2e). The PERT assay works if at least the elements (R1) (2a) (2b) (2c) (2d) are present. This cDNA (2) is linked to the template nucleic acid (1) in the form of a heteroduplex and can be bound to a carrier by (R1); if (R1) is the carrier it is already carrier-bound.

Again it is important to make sure that the template nucleic acid (1) does not act as a specific competitor for the reporter probe (6) and thus yields false-negative results. This is why in reaction (4) the template nucleic acid, RNA (1), is eliminated as a relevant participant in the annealing reaction (5a), by means of one of the methods mentioned. Subsequently, in reaction (5a) a DNA reporter probe (6) is hybridized to the cDNA (2), this reporter probe represents resp. contains the nucleic acid to be amplified and consists of functional sequences (6a) (6b) (6c) (6d) (6e) (6f) (6g). Of these (6f) is obligatory, being the sequence that specifically hybridizes to (2d) of the cDNA (2) synthesized in the RT reaction (3). All other functional sequences of the reporter probe (6) do not hybridize with the cDNA (2) and do not show any sequence identity to any of its functional sequences. (6b) and (6d) are necessary hybridization sequences for the amplification primer. (6d) serves to anneal the first amplification primer; the sequence complementary to 6b) serves to anneal the second amplification primer. (6c) and (6e) are facultative spacer sequences; (6c), however, is desirable. (6a) and (6g) are facultative flanking sequences. The reporter probe (6) may also carry a functional group (R2), either at its 5'-end or elsewhere; this must be different from (R1).

No later than the hybridization (5a) of the reporter probe (6) to the cDNA (2) the cDNA is bound to a carrier by means of the functional group (R1) and unbound reporter probe is completely removed from the reaction mixture under non-denaturing conditions. For a vigorous washing a strong bond between the carrier-bound cDNA (2) and the reporter probe (6) is essential. Therefore, the hybridization sequences, (2d) resp. (6f), of these two nucleic acids must be of sufficient length and suitable structure, and the annealing of the reporter probe (6) must take place under optimal conditions. It is also important to ensure that the binding of the cDNA (2) to the carrier remains intact.

Step 2: Having completely washed away the unbound reporter probe (6), in a further reaction (5b) the first amplification primer (R3) (8a) (8b) is added in a suitable buffer. Preferably this is a DNA oligonucleotide; preferably (R3) is different from (R1). (8b), at the 3'-end, is used for the annealing to (6d) of the reporter probe. (8a), located at the 5'-end, is facultative, not complementary to the reporter probe and neither identical nor complementary to the cDNA (2). By adding a DNA-dependent DNA polymerase and by means of dNTPs the dsDNA (6)//(8) is synthesized in reaction (7). In reaction (4) this dsDNA is denatured, in a new reaction (5) the first as well as the second amplification primer are then annealed to the respective strand of DNA. The 2nd amplification primer (R4) (9a) (9b) is preferably a DNA oligonucleotide neither identical nor complementary to the cDNA; preferably (R4) is different from (R1). The non-complementary (9a) at the 5'-end is facultative. The obligatory (9b) at the 3'-end mediates the annealing to (8d). In reaction (7) the dsDNAs (6)//(8) resp. (8)//(9) are synthesized by means of the DNA-dependent polymerase and dNTPs. These dsDNAs are submitted to the next amplification cycle. The main product of amplification is a dsDNA (R3) (8a) (8b) (8c) (8d) (9a')//(R4) (9a) (9b) (9c) (9d) (9e).

Step 3: Is analogous to step 3 of FIG. 2.

Modifications

Several hybridization sequences (1b) for reporter probes may be placed in the template nucleic acid (1), preferably separated from each other by a short spacer sequence. The hybridization sequences need not be identical, thus different reporter probes may be used. It is also possible to equip the template nucleic acid with several hybridization sequences for RT primers.

The functional sequences and functional groups in the template nucleic acid, the primers and the reporter probe identified as facultative may be dispensed with, whether separately or in the different combinations possible. If sequences (8a) and (9a) of the amplification primers are omitted, the amplification product will be a double-stranded DNA with the functional sequences (8b) (8c) (8d)//(9b) (9c) (9d). (R1) need not be part of the RT primer if conditions for the RT reaction are chosen so that deoxyribonucleotide monosphosphates marked with ligands are incorporated into the newly synthesized cDNA; these functional groups can then, by assuming the function of (R1), bind the cDNA to a carrier.

With regard to the reporter probe (6), (6a) and (6g) may exert any function. This makes it possible to use naturally occurring linear or ring-shaped nucleic acids as reporter probes.

Furthermore it is possible to place the piece of the reporter probe (6) to be amplified not upstream but downstream of the cDNA-binding region (6f), so that it is placed in the (6g) region. The piece to be amplified may also include or overlap with (6f), though the latter is not a preferred constellation.

In divergence from the norm a functional sequence may in certain situations exert more than one function. For example the hybridization functions of (6d) and (6f) may be combined in one sequence. In this case (6d) will at first mediate the annealing of the reporter probe to the cDNA (obviously this requires a template nucleic acid that has been accordingly modified in (1b) !), then, after the unbound reporter probe (6) has been washed away and after a denaturation step necessary in this case, it will also bind the primer (R) (8a) (8b). Thus (6e) and (6f) of the reporter probe as well as the functional sequences derived from these are dropped. As a further modification the hybridization functions of (6d) and (6f) may be arranged so that the involved sequences partly overlap each other. In this case the spacer sequence (6e) and the sequences derived thereof are dropped.

A partial though only minor overlapping is also possible for (1b) and (1d) of the template nucleic acid (1), as long as this does not hybridize the reporter probe to (2b).

In deviation from the norm identical base sequences may be used for different functional sequences; these may also be homopolymeric. This applies to the flanking sequences (1a) and (1e) as well as the spacer sequence (1c) of the template nucleic acid, which may be homopolymeric and/or identical to each other. The flanking sequences (6a) and (6g) as well as the spacer sequences (6c) and (6e) of the reporter probe (6) also may be homopolymeric abd/or identical to each other.

Organization of the Pert Assay using an Amplification Procedure Based on Ligase Chain Reaction (LCR) in Step 2

Figure 4:
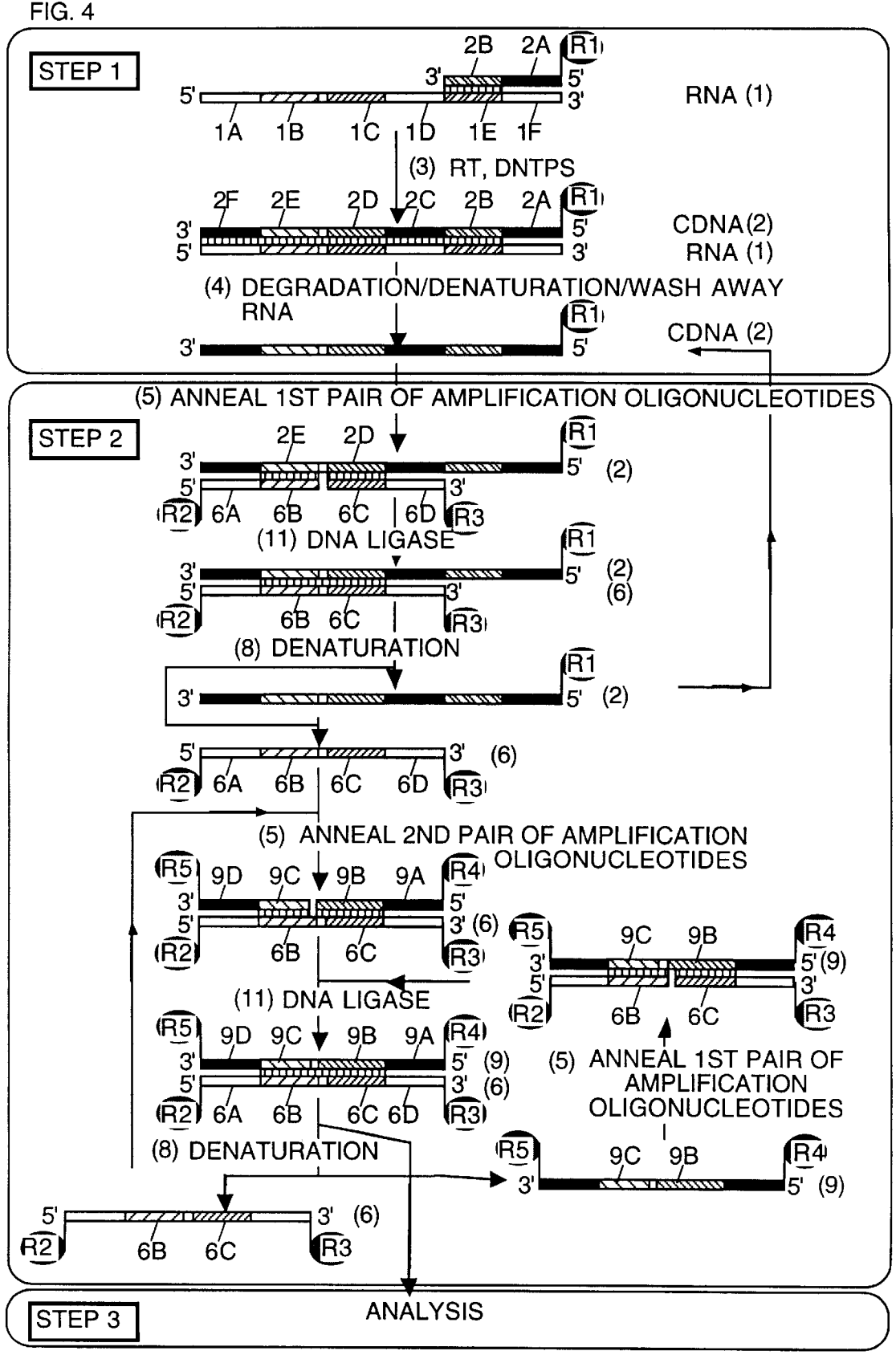
FIG. 4 shows the structure of the PERT assay for an illustrative variant, in which the nucleic acid to be amplified is a sequence of cDNA, which sequence is amplified by means of the ligase chain reaction.
Figure 5:
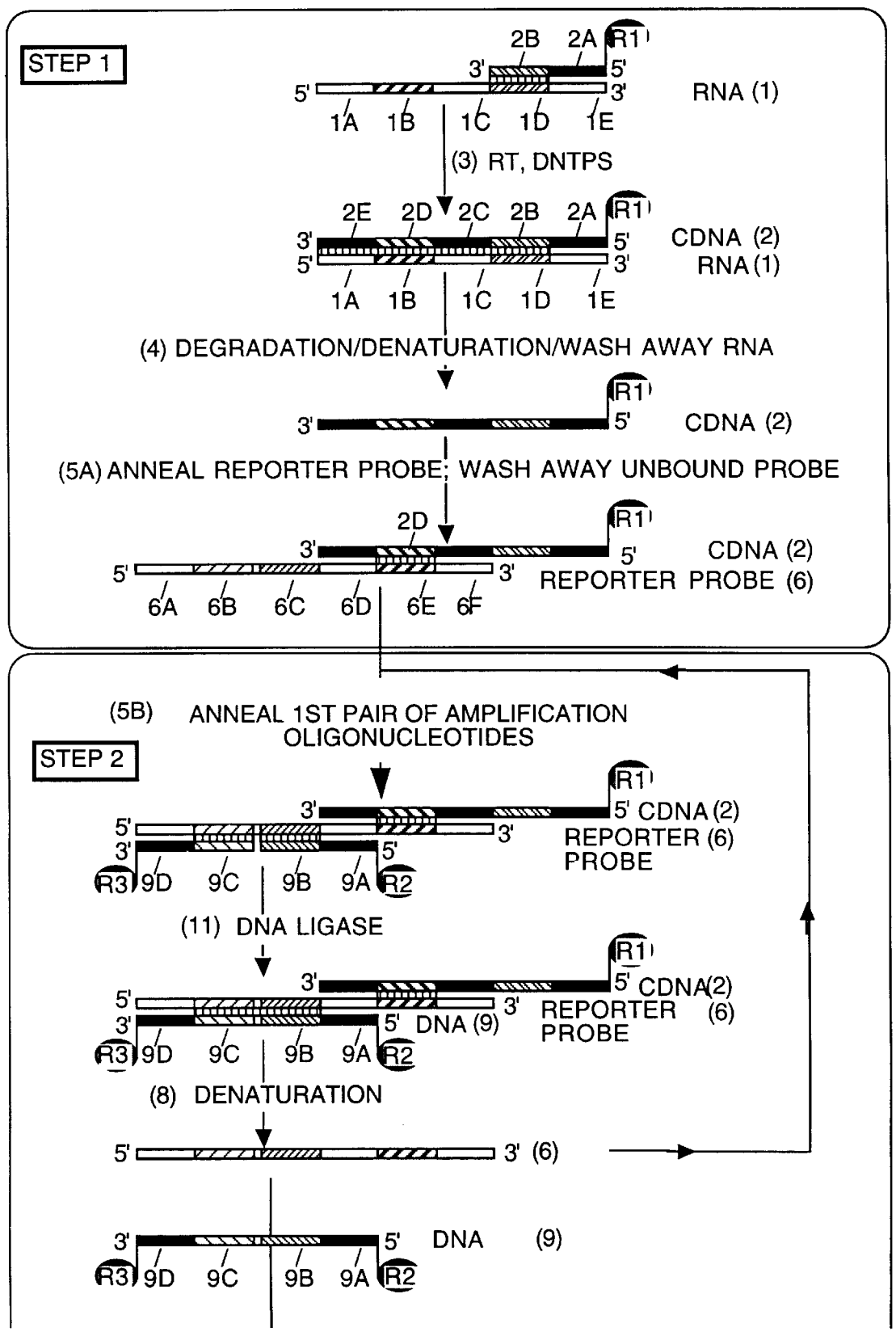
FIG. 5 shows the structure of the PERT assay for an illustrative variant, in which the nucleic acid to be amplified is a sequence of a reporter probe, which sequence is amplified by means of the ligase chain reaction.
Figure 5:
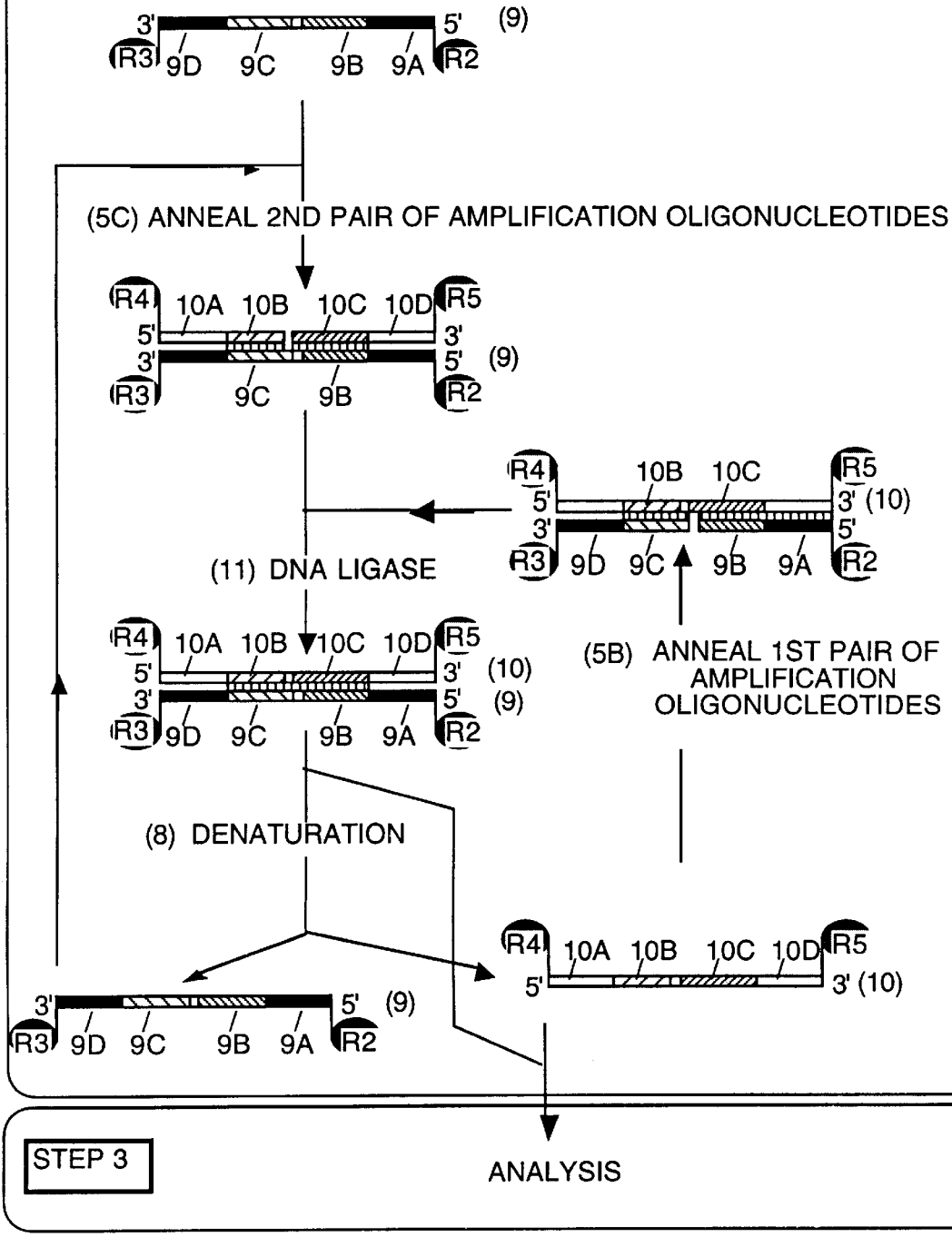

According to PS WO 89/12696 and WO 89/09835 the LCR is another method for the amplification of nucleic acid sequences. FIGS. 4 and 5 describe its possible use for the PERT assay. Preferably a pure RNA is used as template nucleic acid in this case; the sequence of the template nucleic acid to be amplified in step 2 must on no account consist of DNA. The functional sequences to be used include hybridization, spacer and flanking sequences.

FIG. 4 shows the principal procedure if a sequence that is part of the cDNA itself is amplified.

Step 1: A template nucleic acid (1) that contains the functional sequences (1a) to (1f) is used. Of these (1b), (1c) and (1e) are hybridization sequences and necessary for the functioning of the PERT assay. (1d) is a facultative spacer sequence, and (1a) and (1f) are facultative flanking sequences. Of the three hybridization sequences (1e) is used for the annealing of the RT primer. (1b) and (1c), which are directly connected to each other, as well as the sequences complementary to these, are used for the annealing of the two DNA oligonucleotide pairs needed for the LCR amplification of a partial sequence of the product of the RT reaction. The RT primer (R1) (2a) (2b) contains the necessary hybridization sequence (2b) at its 3'-end. (2a) at the 5'-end is facultative and is not complementary to the template nucleic acid. (R1) is also facultative. If the RT primer is a DNA, sequence (2a) allows to add additional desired functions to the cDNA. If RT activity is present in the pretreated sample, in reaction (3) a cDNA (2) containing as a maximum the elements (R1) (2a) (2b) (2c) (2d) (2e) (2f) is synthesized by means of dNTPs. The PERT assay works only if at least all functional sequences up to and including (2e) are synthesized. This cDNA contains the nucleic acid to be amplified by means of LCR.

For an optimal functioning of the PERT assay the template RNA of the template nucleic acid (1) is at first degraded in reaction (4) and then eliminated as a reaction partner in the following reactions. This is desirable in order to avoid the annealing of the second pair of oligonucleotides to the template nucleic acid. Such an annealing may, depending on the conditions of reaction and the reagents chosen, lead to false-positive or false-negative results of the PERT assay. False-positive results occur when the second pair of oligonucleotides bound to the template nucleic acid, which consists of (R4) (9a) (9b) and (9c) (9d) (R5) [see below], is ligated by a ligase such as that from bacteriophage T4 to form a coherent DNA strand. False-negative results occur when the second pair of oligonucleotides bound to the template nucleic acid (1), though not ligated to a coherent DNA strand by the ligase employed, is depleted from the reaction due to it being hybridized to the large amount of template nucleic acid.

Step 2: In reaction (5) two DNA oligonucleotides, (R2) (6a) (6b) and (6c) (6d) (R3), are hybridized to the cDNA. These two oligonucleotides are completely complementary in their hybridization sequences (6b) resp. (6c) to (2e) resp. (2d) of the cDNA and after the annealing to these are only separated by a nick. (6a) and (6d) are facultative, they are neither identical nor complementary to the cDNA and are used for the addition of supplementary DNA sequences to the amplification product. The oligonucleotide (6c) (6d) (R3) is phosphorylated at its 5'-end. The functional groups, which also are facultative, are preferably located as close to the 5'-end of (6a) (6b) in the case of (R2) and as close as possible to the 3'-end of (6c) (6d) in the case of (R3). In reaction (11) a DNA ligase (e.g. of the bacteriophage T4; preferably a heat-resistant enzyme is used) is used for the ligation of the two oligonucleotides, by means of which the DNA strand (6) is produced. In reaction (8) denaturation follows, so that strand (2) is again available for the annealing of the two oligonucleotides (R2) (6a) (6b) and (6c) (6d) (R3). Strand (6) is used for continuing the amplification.

Reaction (5) starts with the annealing of a further pair of DNA oligonucleotides, which is analogous to the first pair. This second pair contains the oligonucleotides (R4) (9a) (9b) and (9c) (9d) (R5). Their hybridization sequences (9b) resp. (9c) are entirely complementary to (6c) resp. (6b) and will lie next to each other after the annealing; preferably in such a way that the nick between the 3'-end of the one and the 5'-end of the other is shifted by one nucleotide with regard to the nick that was present in strand (6). In addition, the 5'-end of (9c) (9d) (R5) must carry a phosphate group. With regard to the localization of the facultative functional groups it is preferable for (R4) to be located as closely as possible towards the 5'-end of (9a) (9b), and for (R5) to be as close as possible towards the 3'-end of (9c) (9d). (9a) and (9d) are again facultative. (9a) is or is not complementary to (6d); (9d) is or is not complementary to (6a). The non-complementary sequences (9a) resp. (9d) are used for the addition of further functional sequences to the amplification product. The complementary sequences (9a) resp. (9d), on the other hand, extend the hybridization sequences. By means of renewed action of the DNA ligase (11) the two oligonucleotides (R4) (9a) (9b) and (9c) (9d) (R5) are ligated to strand (9), which forms a partial duplex with strand (6). A further denaturation (8) is again followed by the annealing (5) of the respective complementary pairs of oligonucleotides to the separated strands (6) and (9); this cyclical amplification results in large quantities of the double-stranded DNA oligonucleotide dimer (6)//(9).

Step 3: This product may be subjected to analysis according to the general remarks concerning step 3 below. As an alternative it is possible, if markers have been introduced by means of (R), to use simple systems for the detection of DNA molecules that carry certain newly formed combinations of functional groups (R). These combinations are: (R2) and (R3), (R2) and (R4), (R5) and (R4), (R5) and (R3). Such detection systems may be based on ELISA but also on particle agglutination. As the DNA is single-stranded in these regions, the non-complementary functional sequences (6a), (6d), (9a) and (9d), which were introduced by means of oligonucleotides may be used for detection by means of hybridization.

Modifications

All functional sequences and functional groups of the nucleic acids used that have been identified as facultative may be dispensed with, whether single or in one of the various possible combinations. If (6a), (6d), (9a) and (9d) are all eliminated, the amplification product (6)//(9) is a dsDNA molecule consisting of the sequences (6b) (6c)//(9b) (9c). The flanking sequences (9a) resp. (9d) can be shaped so that they are complementary to (6d) resp. (6a).

The flanking sequences (1a) and (1f) of the template nucleic acid (1) may exert any function, thus allowing to use natural RNA molecules as template nucleic acid (1).

The template nucleic acid (1) may contain more than one hybridization sequence for the RT primer.

In deviation from the norm a functional sequence may in certain situations exert more than one function. For example the hybridization functions of (1c) and (1e) may be combined. In this case (1c) mediates the annealing of (R4) (9a) (9b), which now also serves as RT primer, to the template nucleic acid (1). As mentioned (R4) (9a) (9b) is one of the amplification oligonucleotides used in step 2. Therefore the functional sequences (1d) and (1e) of the template nucleic acid as well as all functional sequences derived from these are dropped. A separate RT primer (R1) (2a) (2b) also is dispensable.

A further modification is to arrange these hybridization functions so that the sequences (1c) and (1e) partly overlap. In this case the spacer sequence (1d) and all sequences derived from this are dropped.

By using different sequences for the annealing of the RT primer and of the amplification oligonucleotide (R4) (9a) (9b) it becomes possible to use a RNA primer; thus the sensitivity and/or the specificity of the PERT assay can be influenced.

In deviation from the norm it is possible to use identical base sequences for different functional sequences, these may also be homopolymeric. This applies for the flanking sequences (1a) and (1f) as well as the spacer sequence (1d) of the template nucleic acid (1), which may be homopolymeric and/or identical to each other.

A further possible, though not preferable modification consists of using the same sequence for the hybridization sequences (1b) and (1c) of the template nucleic acid (1), a sequence that is not identical to the sequences of the spacer element (1d), the hybridization sequence for the RT primer (1e) and the flanking sequences (1a) and (1f). In this case the amplification oligonucleotides can only consist of a hybridization sequence and must be phosphorylated at the 5'-end.

FIG. 5 shows the procedure if instead of the cDNA at least a partial sequence of a reporter probe is amplified.

Step 1: The template-primer combination, RT reaction (3) as well as their product are in all aspects identical to those in FIG. 3. The mixture of nucleic acids produced in reaction (3) is modified in reaction (4) in a way that will prevent the template nucleic acid (1) from acting as a specific competitor for the reporter probe (6) in the following reactions, thus leading to false-negative results. Therefore one of the methods mentioned above is used in reaction (4) to eliminate the existing template nucleic acid (1) as a relevant participant in the annealing reaction (5a).

In reaction (5a) a DNA reporter probe (6) is hybridized to the cDNA (2); this DNA reporter probe (6) is or contains the nucleic acid to be amplified and consists of (6a) (6b) (6c) (6d) (6e) (6f). Of these (6e) is the specific hybridization sequence for (2d) of the cDNA synthesized in the RT reaction (3). All other functional sequences of the reporter probe do not hybridize to the cDNA. (6b) and (6c) are directly adjacent and are necessary hybridization sequences for the amplification oligonucleotides. Preferably they will be neither identical nor complementary to each other, neither may they be identical or complementary to the cDNA. (6d) is a non-obligatory spacer sequence. (6a) amd (6f) are non-obligatory flanking sequences. No later than after the hybridization (5a) of the reporter probe (6) to the cDNA (2), the cDNA is bound to a carrier by means of the functional group (R1) and unbound reporter probe is eliminated entirely from the reaction mixture under non-denaturing conditions, as explained for FIG. 3.

Step 2: Afterwards, in a further annealing reaction (5b) and by using a suitable buffer, the first pair of amplification oligonucleotides, (R2) (9a) (9b) and (9c) (9d) (R3), is added. (9b) resp. (9c) of these two oligonucleotides are totally complementary to (6c) resp. (6b) and, after annealing to these, are only separated from each other by a nick. Furthermore (9c) (9d) (R3) is phosphorolyzed at the 5'-end. (9a) resp. (9d) are facultative, are neither identical nor complementary to the reporter probe and are used for the addition of any desired supplementary DNA sequences to the amplification product. With regard to the localisation of the facultative functional groups, (R2) should preferably be located as close as possible to the 5'-end of (9a) (9b) and (R3) as close as possible to the 3'-end of (9c) (9d). Neither (R2) nor (R3) must be identical to (R1), and they must not be carriers. In reaction (11) the two oligonucleotides (R2) (9a) (9b) and (9c) (9d) (R3) are ligated to a coherent sequence by means of the DNA ligase. In reaction (8) denaturation follows, so that the reporter probe (6) is again avaiblable for the annealing of the two oligonucleotides (R2) (9a) (9b) and (9c) (9d) (R3). Strand (9) is used for further amplification.

This starts in reaction (5) by annealing another pair of DNA oligonucleotides that are analogous to the first pair.

This second pair consists of the oligonucleotides (R4) (10a) (10b) and (10c) (10d) (R5), whose functional sequences (10b) resp. (10c) are entirely complementary to (9c) resp. (9b) and which are directly adjacent after the annealing, preferably in such a way that the nick between the 3'-end of the one and the 5'-end of the other is shifted by one nucleotide with regard to the nick that was present in strand (9). In addition the 5'-end of the oligonucleotide (10c) (10d) (R5) must carry a phosphate group.

With regard to the localization of the facultative functional groups, (R4) should preferably be located as close as possible to the 5'-end of (10a) (10b) and (R5) should be as close as possible to the 3'-end of (10c) (10d). Furthermore it is preferable for (R4) and (R5) to be different from (R1) and not to be carriers. (10a) and (10d) are facultative non-complementary flanking sequences and can be used for the introduction of other functions into the amplification product.

By renewed action of the DNA ligase (11) the two oligonucleotides (R4) (10a) (10b) and (10c) (10d) (R5) are ligated to strand (10), which forms a partial duplex with strand (9). Following a further denaturation (8) the two respective complementary pairs of oligonucleotides are then again annnealed (5) to the separated strands (9) and (10); this cyclical amplification results in large quantities of the partly double-stranded DNA-oligonucleotide dimer (9)//(10).

Step 3: The partly double-stranded DNA-oligonucleotide dimer (9)//(10) is analyzed by using the methods mentioned in FIG. 4.

Modifications

Several hybridization sequences (1b) for reporter probes may be placed in the template nucleic acid (1), preferably separated from each other by a short spacer sequence. The hybridization sequences need not be identical, therefore different reporter probes may be used. There may also be several hybridization sequences for the RT primer.

Any elements in the template nucleic acid, the RT primer, the reporter probe and the amplification oligonucleotides that have been identified as facultative can be omitted, whether alone or in one of the different possible combinations. The flanking sequences (10a) and (10d) can be complementary to (9d) and (9a). (R1) can be omitted as a part of the RT primer if conditions for the RT reaction are chosen so that ligand-labeled deoxyribonucleotide monophosphates are integrated into the newly synthesized cDNA; these functional groups will be able to bind the cDNA to a carrier, thus exerting the function of (R1).

The flanking sequences (6a) and (6f) of the reporter probe may have any kind of base sequence. It is thus possible to use natural linear or ring-shaped DNA molecules as reporter probe.

It is also possible to place the region of the reporter probe (6) to be amplified not upstream but downstream of the cDNA-binding hybridization sequence (6e), thus overlapping with (6f). The area that is to be amplified may also overlap with (6e); however this is not a preferable constellation.

In deviation from the norm a given functional sequence may in certain situations exert more than one function. For example the hybridization functions of (6c) and (6e) may be joined. In this case (6c) will first be used for annealing the reporter probe to the cDNA (of course this will require a template nucleic acid accordingly modified!), and will then, after the unbound reporter probe has been washed away and after the denaturation necessary in this case, bind the amplification oligonucleotide (R2) (9a) (9b). As these two functions have been combined to (6c), the functional sequences (6d) and (6e) of the reporter probe as well as the functional sequences derived from these are dropped.

Another possible modification is to arrange these hybridization functions in such a way that the involved sequences overlap in part. In this case the spacer region (6d) and any sequences derived from this are dropped.

Finally partial overlapping of only a few nucleotides also is possible for the functional sequences (1b) and (1c) of the template nucleic acid (1), as long as this does not result in the hybridization of the reporter probe to (2b). In deviation from the norm it is also possible to use identical base sequences for different functional sequences, these may also be homopolymeric. This applies to the flanking sequences (1a) and (1e) as well as the spacer sequence (1c) of the template nucleic acid, which may be homopolymeric and/or identical to each other. The same holds for the flanking sequences (6a) and (6f) and the spacer element (6d) of the reporter probe (6), these too may be homopolymeric and/or identical to each other.

A possible though not preferred modification is to use only one base sequence for the two oligonucleotide hybridization regions (6b) and (6c) of the reporter probe (6); this base sequence must be different from the sequences of the spacer element (6d), the hybridization sequence (6e) and the flanking sequences (6a) and (6f). In this case the amplification oligonucleotides may only consist of a hybridization sequence and must be phosphorylated at the 5'-end.

Organization of the Pert Assay when using the "Process for Amplifying and Detecting Nucleic Acid Sequences" (WO 90/01069) in Step 2

Figure 6:
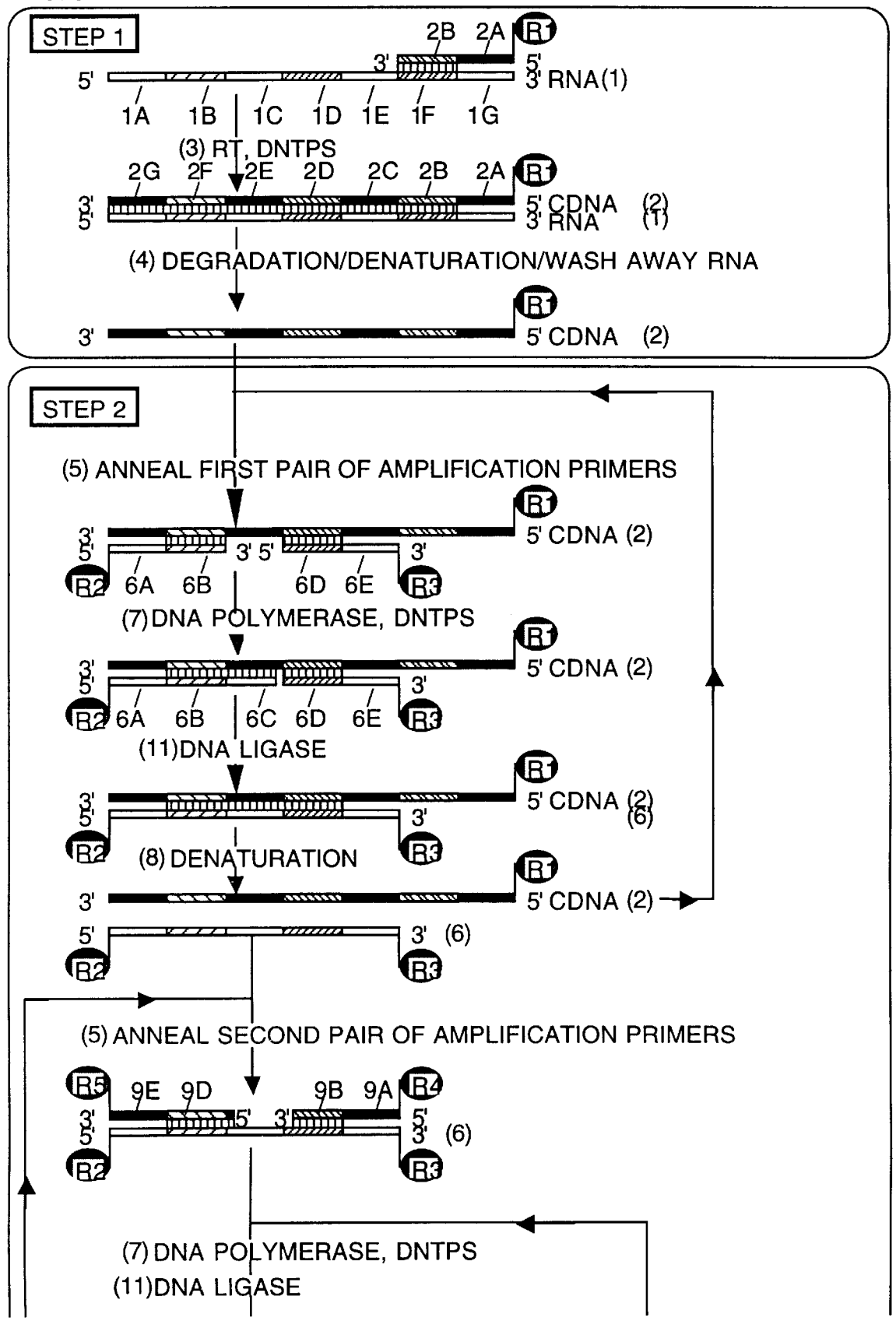
FIG. 6 shows the structure of the PERT assay for an illustrative variant, in which the nucleic acid to be amplified is a sequence of the cDNA, which sequence is amplified by means of a procedure that combines elements of both PCR and LCR.
Figure 7:
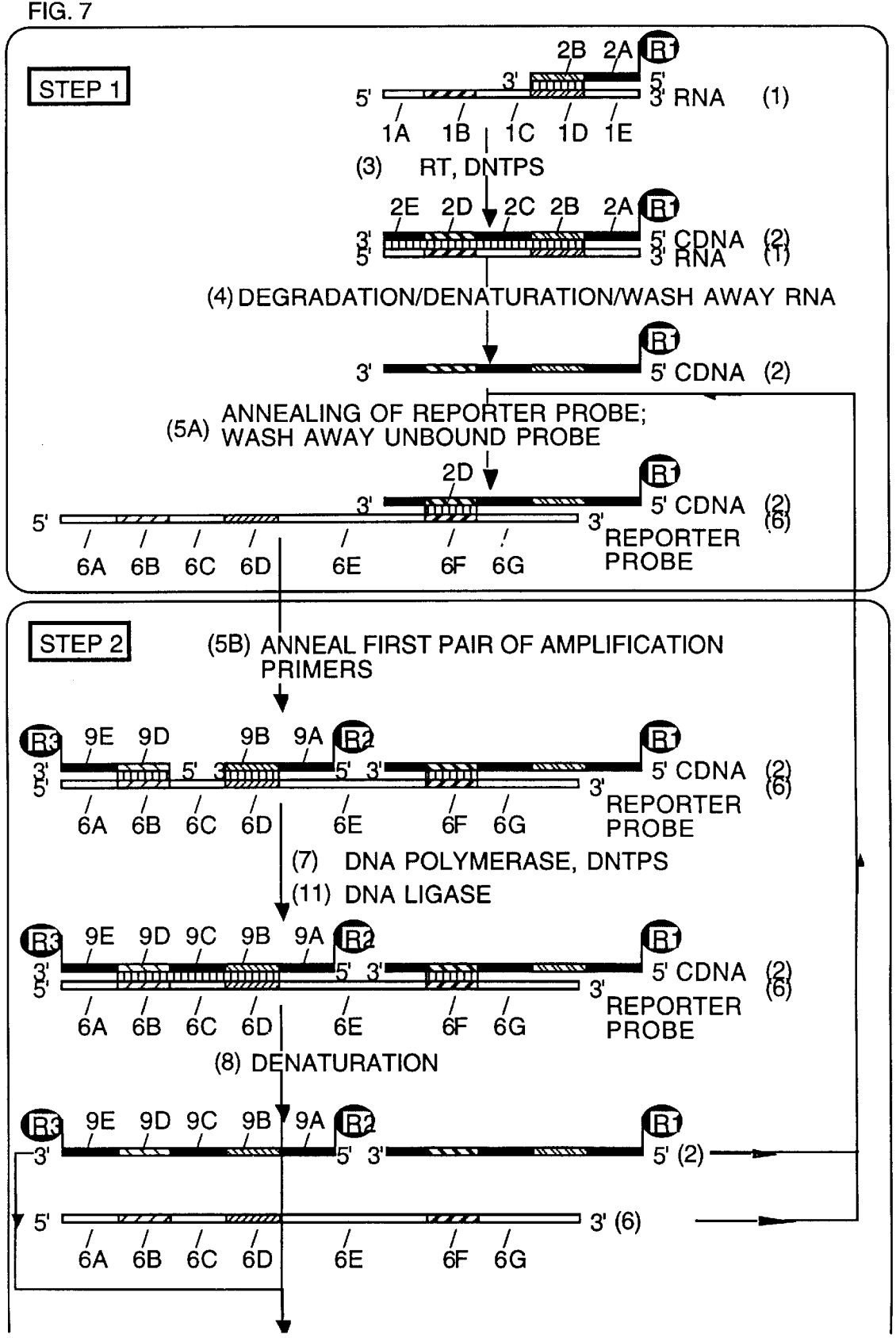
FIG. 7 shows the structure of the PERT assay for an illustrative variant, in which the nucleic acid to be amplified is a sequence of a reporter probe, which sequence is then amplified according to a procedure that combines elements of both PCR and LCR.

FIGS. 6 and 7 show the reaction process of the PERT assay in connection with this amplifying process, which uses elements of both the Ligase Chain Reaction and the Polymerase Chain Reaction. In this case it is preferable to use a pure RNA as template nucleic acid; on no account may the template nucleic acid sequence to be amplified in step 2 consist of DNA. Functional sequences to be used include hybridization-, spacer- and flanking sequences.

FIG. 6 shows a variant in which the nucleic acid to be amplified is a partial sequence of the cDNA.

Step 1: The template nucleic acid used contains the functional sequences (1a) to (1g). The template nucleic acid (1), the RT primer (R1) (2a) (2b) and the cDNA (2) are identical to those from FIG. 2 with regard to structure, functions and terminology. Unlike FIG. 2 the spacer sequence (1c) is here necessary. The reagents and the conditions of reaction for the RT reaction and their product are also identical. The PERT assay can only succeed if all functional sequences up to and including (2f) are synthesized in this reaction.

To ensure an optimal course of the PERT assay the template nucleic acid is in reaction (4) first degraded by one of the methods mentioned and then eliminated as a reaction partner participating in the following reactions. This is desirable since it prevents the annealing of the second pair of oligonucleotides to the template nucleic acid. Depending on the conditions of reaction and reagents chosen, such an annealing may lead to false-positive or false-negative results of the PERT assay: false-positive results occur if the DNA-dependent DNA polymerase used in the subsequent reactions also has a RNA-dependent DNA polymerase activity, and if the ligase used can simultaneously ligate the DNA fragments even if these are present as a RNA//DNA heteroduplex. The ligase from the bacteriophage T4 is an example for a ligase with such a function. False-negative results occur if the second pair of oligonucleotides hybridized to the template nucleic acid (1), though not ligated to a coherent strand of DNA as a result of the ligating process, is kept from annealing to the ligated first pair of oligonucleotides because of it being hybridized to the template nucleic acid, thus leading to a less than optimal PCR process.

Step 2: In reaction (5) now a first pair of DNA oligonucleotide primers is hybridized to the cDNA (2). The obligatory (6b), which is located at the 3'-end of the primer (R2) (6a) (6b), is used for the hybridization of (2f) to the cDNA. (6a), which is located at the 5'-end, is facultative, not complementary to the cDNA and is used for the introduction of a new sequence not yet part of the cDNA. (R2) is also facultative and preferably different from (R1). The second of the two primers, (6d) (6e) (R3), has the same polarity as the first and consists of an obligatory hybridization sequence located at the 5'-end (6d), which is complementary to (2d) of the cDNA and phosphorylated at the 5'-end, and of the facultative sequence (6e), which is located at the 3'-end of the primer and can be used for the introduction of any further desired sequences. The facultative (R3) is preferably not identical to (R1).

In contrast to the LCR, where the two amplification oligonucleotides of a pair are directly adjacent to each other, they are here separated by the spacer sequence (2e) of the cDNA. According to PS WO 09/01069 the preferred length for (2e) is only a couple of nucleotides, though the PERT assay also works with a longer (2e) sequence. In reaction (7) a DNA-dependent DNA polymerase — only DNA polymerases without any synthesis-dependent 5'->3'exonuclease activity may be used for this — (6c), which is complementary to (2e), is synthesized in a "gap filling" reaction by including the dNTPs; (6c) remains separated from the primer (6d) (6e) (R3) by a nick. In reaction (11) a DNA ligase (e.g. from the bacteriophage T4; preferably a heat-resistant enzyme is used) is used for the ligation of the two fragments, thus generating the coherent DNA strand (6). Denaturation follows in reaction (8), thus strand (2) is again available for the annealing of the first pair of primers. Strand (6) is used for further amplification.

Reaction (5) starts with the annealing of the second pair of DNA oligonucleotide primers. The hybridization sequences (9b) and (9d) used for this are complementary to (6d) resp. (6b) of the first pair of primers. The first primer of the second pair of primers consists of the elements (R4) (9a) (9b), as mentioned the obligatory (9b) located at the 3'-end of this primer is used for the hybridization of (6d) to the second DNA strand. (9a) at the 5'-end is facultative, not complementary to (6e) and can be used to introduce any further desired functions into the amplification product. (R4) is facultative and preferably not identical to (R1). The second primer of this pair has the same polarity and consists of the functional sequences (9d) (9e) (R5). At its 5'-end it is phosphorylated. The obligatory (9b) at the 5'-end is complementary to (6b). (9e) at the 3'-end is facultative, not complementary to (6a) and can be used to introduce any further desired functions into the amplification product. (R5) is facultative and preferably not identical to (R1). This pair of primers is also hybridized to the DNA strand (6). By means of renewed action of the polymerase and by using dNTPs in another "gap filling reaction" the gap between the two primers is closed, and by means of DNA ligase the two fragments are connected to strand (9) in reaction (11). The functional sequences (9b) (9c) (9d) connect strand (9) and (6) into a partial duplex. (9a) and (9e), on the other hand, are not complementary to (6e) resp. (6a) of strand (6). Further denaturation (8) is again followed by the annealing (5) of the two respective complementary pairs of primers to the separated strands (6) and (9); large amounts of the partial duplex (6)//(9) are yielded as the product of this cyclical amplification.

Step 3: This product may be used for analysis according to the general directives for step 3 below. If (R) has been used for markings a possible alternative is to use simple systems for the detection of DNA molecules that carry certain newly formed combinations of functional groups (R). These combinations are: (R2) and (R3), (R2) and (R4), (R5) and (R4), (R5) and (R3). Again such detection systems may be based on an ELISA or the simple and cheap particle agglutination. As the DNA is single-stranded in these regions the non-complementary functional sequences (6a), (6e), (9a) and (9e), which have been introduced by means of the oligonucleotides, can be used for detection by means of hybridization.

Modifications

All functional sequences and functional groups of the nucleic acids used that have been identified as facultative may be dropped, whether individually or in any of the various possible combinations. If all four (6a), (6e), (9a) and (9e) are missing the amplification product is a double-stranded DNA consisting of the sequences (6b) (6c) (6d)// (8b) (8c) (8d). The flanking sequences (9a) and (9e) can also be made complementary to (6e) resp. (6a).

(1a) and (1g) of the template nucleic acid (1) may have any sequence, the only restriction being that they must not interfere unduely with an optimal course of the PERT assay. The same restriction applies for the option to use natural RNA molecuiles as template nucleic acid (1). The template nucleic acid may contain several hybridization sequences for RT primers.

In deviation from the norm the hybridization sequences (1d) and (1f) may be combined. In this case (1d) first mediates the annealing of (R4) (9a) (9b), which now also serves as RT primer, to the template nucleic acid (1). As mentioned (R4) (9a) (9b) is one of the amplification primers in step 2. Thus (1e) and (1f) of the template nucleic acid (1) are dropped. A separate RT primer (R1) (2a) (2b) also becomes unnecessary.

As a further modification it is possible to arrange the hybridization sequences (1d) and (1f) in such a way that they overlap partially. In this case the spacer sequence (1e) and the sequences derived from this are dropped.

Using different sequences for the annealing of the RT primer and the second amplification primer also allows using a RNA primer; thus the sensitivity and/or the specificity of the PERT assay can be influenced. In deviation from the norm it is possible to use identical base sequences for different functional sequences; these may also be homopolymeric. This applies to both the flanking sequences (1a) and (1g) and the spacer sequences (1c) and (1e) of the template nucleic acid (1); these may be homopolymeric and/or identical to each other.

Furthermore it is possible to use only one single base sequence, which must be different from the spacer and flanking sequences, for at least two of the hybridization sequences (1b), (1d) and (1f) of the template nucleic acid (1). This is illustrated in the following example for all three hybridization sequences being identical: In this case the one primer still necessary, resp. also its complementary primer, must consist of one hybridization sequence only and must be phosphorylated at its 5'-end. Under these conditions no more than three of these primer molecules will bind to the template nucleic acid (1); the cDNA synthesis is complementary to (1e), (1c) and (1a), and the RT reaction produces three fragments, each separated from the other by a nick and bound to the template nucleic acid, (2b) (2c), (2d) (2e) and (2f) (2g). Using the DNA ligase mentioned these fragments are then ligated to (2b) (2c) (2d)2e) (2f) (2g). This version may be made even simpler by eliminating the functional sequences (1e) and (1f) from the template nucleic acid as described above. In this case only the cDNA fragments (2d) (2e) and (2f) (2g) are produced and ligated by means of DNA ligase. Strands (2b) (2c) (2d) (2e) (2f) (2g) as well as (2d) (2e) (2f) (2g) would then be amplified with the help of a second primer following the same principle in an amplification process according to PS WO 90/01069.

FIG. 7 shows a variant in which the cDNA synthesized in the RT reaction is used for the specific hybridization of a partially complementary reporter probe which is the nucleic acid to be amplified.

Step 1: The template-primer combination, the RT reaction (3) and their product are in all aspects identical to those in FIG. 3. The mixture of nucleic acids produced in the RT reaction (3) is modified in reaction (4) in such a way that makes sure that the template nucleic acid (1) cannot act as a specific competitor for the reporter probe (6) and thus lead to false negative results. In reaction (4) one of the methods mentioned is therefore used to eliminate any existant template nucleic acid (1) as a relevant participant in the annealing reaction (5). Following this, in reaction (5a) a DNA reporter probe (6), which is or contains the nucleic acid to be amplified and which consists of (6a) (6b) (6c) (6d) (6e) (6f) (6g). Of these (6f) is the necessary hybridization sequence which hybridizes to the (2d) of the cDNA that has been synthesized in reaction (3). All other functional sequences of the reporter probe (6) do not hybridize to the cDNA (2) and none of their sequences are identical. (6b) and (6d) also are necessary hybridization sequences for the amplification primer. (6d) is used for annealing the second amplification primer. (6c) and (6e) have spacer function; of these only (6c) is necessary. (6a) and (6g) are facultative flanking sequences.

No later than after the hybridization (5a) of the reporter probe (6) to the cDNA (2) the cDNA is bound to a carrier by means of the functional group (R1), and unbound reporter probe is completely eliminated from the reaction mixture under non-denaturing conditions, as described in FIG. 3.

Step 2: In a further annealing reaction (5b) a suitable buffer is used to to add the first pair of amplification oligonucleotide primers, (R2) (9a) (9b) and (9d) (9e) (R3). (9b) and (9d) of these two primers are entirely complementary to (6d) resp. (6b). In addition, (9d) (9e) (R3) is phosphorylated at its 5'-end. (R2) resp. (R3) are facultative and preferably different from (R1). In reaction (7) the gap between the two primers is then closed by means of the DNA-dependent DNA polymerase by using dNTPs, and in reaction (11) the two fragments (R2) (9a) (9b) (9c) and (9d) (9e) (R3) are connected to a single strand (9) by means of the DNA ligase. In reaction (8) denaturation follows, thus the reporter probe (6) is again available for the annealing of the two oligonucleotides (R2) (9a) (9b) and (9d)9e) (R3). Strand (9) is used for further amplification.

Reaction (5c) then effects the annealing of the second pair of DNA oligonucleotide primers. The first primer of the second pair of primers consists of (R4) (10a) (10b), the obligatory (10b) which is located at the 3'-end mediates the hybridization to (9d). (10a), at the 5'-end, is facultative and may be used to introduce any other desirable functions to the amplification product. The same restrictions apply here as for (2a) or (9a). (R4) is facultative and preferably different from (R1) and not a carrier. The second primer (10d) (10e) (R5) of this pair has the same polarity and is phosphorylated at its 5'-end. (10d), located at the 5'-end, is complementary to (9b). (10e), located at the 3'-end, is facultative and again may be used for the introduction of another functional sequence. (R5) is another facultative functional group, preferably different from (R1) and not a carrier.

This pair of primers is hybridized to the DNA strand (9). By renewed action of the DNA polymerase and by using dNTPs the gap between the two primers is closed in a further "gap filling" reaction, and, in reaction (11) the two fragments are connected to strand (10) by means of DNA ligase. Strand (10) and strand (9) are connected to a partial duplex by the functional sequences (10b) (10c) (10d). (10a) and (10e), however, are not complementary to (9e) resp. (9a) of strand (9). Another denaturation process (8) is again followed by the annealing (5) of the respective complementary primer pairs to separated strands (9) and (10); this cyclical amplification yields large amounts of the partial duplex (9)//(10).

Step 3: This product may be used for the analysis according to the general remarks on step 3 beneath. If (R) has been used for markers, it is alternatively possible to use simple detection systems for the detection of DNA molecules carrying certain combinations of (R). These combinations are: (R2) and (R3), (R2) and (R4), (R5) and (R4), (R5) and (R3). Such detection systems may also be based on ELISA or the simple and cost saving particle agglutination. Since the DNA is single-stranded in these regions, the non-complementary sequences (9a), (9e), (10a) and (10e) introduced by means of the oligonecleotides may be used for the detection by means of hybridization.

Modifications

Several hybridization sequences (1b) for reporter probes may be placed in the template nucleic acid (1), preferably separated from each other by short spacer sequences. The hybridization sequences need not be identical, therefore various reporter probes may be used. It is also possible to use several hybridization sequences for RT primers.

All functional sequences and functional groups of the used nucleic acids that have been identified as facultative may be dropped individually or in the various possible combinations. In the template nucleic acid (1) these are the flanking sequences (1a) and (1e) as well as the spacer sequence (1c). In the reporter probe (6) the flanking sequences (6a) and (6g) as well as the spacer sequence (6e) may be omitted. With regard to the various primers the non-complementary sequences (2a), (9a), (9e), (10a) and (10e) may be dispensed with. If all four of (9a), (9e), (10a) and (10e) are missing the amplification product is a double-stranded DNA consisting of (9b) (9c) (9d)//(10b) (10c) (10d). The flanking sequences (10a) resp. (10e) of the second pair of amplification primers may be designed so that they are complementary to (9e) resp. to (9a). It is also possible to dispense with several or all of the functional groups (R2) (R3) (R4) (R5). (R1) is dispensable as a part of the RT primer if conditions for the RT reactions are chosen in such a way that deoxyribonucleotide monophosphates marked with ligands are built into the newly synthesized cDNA; these functional groups can then bind the cDNA to a carrier in the sense of (R1).

(6a) and (6g) of the reporter probe (6) may be of any desired sequence. Thus it is possible to use naturally linear or ring-shaped DNA molecules as a reporter probe.

Furthermore it is possible to place the region of the reporter probe (6) to be amplified not upstream but downstream of the hybridization sequence (6f), which binds the cDNA, thus positioning it in the region of (6g). The region to be amplified may also include or overlap with (6f); the latter, however, is not a preferred constellation.

In deviation from the norm a functional sequence may have more than one function in certain situations. For example the hybridization functions of (6d) and (6f) may be combined. In this case sequence (6d) will first be used in reaction (5a) for the annealing of the reporter probe to the cDNA (of course this will need a template nucleic acid that has been modified accordingly!), and will then bind the primer (R2) (9a) (9b), after the unbound reporter probe has been washed away and after a denaturation process which becomes necessary in this case. If (1a) of the template nucleic acid is omitted, denaturation is not necessary. Due to the combination of these two functions to (6d) the functional sequences (6e) and (6f) of the reporter probe are no longer necessary. Another possible modification is to arrange the hybridization functions in such a way that the sequences (6d) and (6f) mediating these functions overlap in part. In this case the spacer sequence (6e) and any sequences derived from this becomes unnecessary.

Finally, the possibility of the partial overlapping of only a couple of nucleotides also works for the functional sequences (1b) and (1d) of the template nucleic acid (1), as long as the reporter probe is not thus hybridized to (2b).

In deviation from the norm identical base sequences may be used for various functional sequences, these may also be homopolymeric. This is the case for the flanking sequences (1a) and (1e) as well as the spacer sequence (1c) of the template nucleic acid, which may be homopolymeric and/or identical to each other. The flanking sequences (6a) and (6g) as well as the spacer sequences (6c) and (6e) of the reporter probe (6) may also be homopolymeric and/or identical to each other.

Furthermore it is possible to to use one single base sequence, provided it is different from the sequences of the spacer and the flanking sequences, for at least two of the hybridization sequences (6b), (6d) and (6f) of the reporter probe (6). This is illustrated in the following example, where all three hybridization sequences are identical: In this case the one primer still necessary, resp. the primer complementary to this one, must consist of only one hybridization sequence and must be phosphorylated at its 5'-end. Under these circumstances either (6b), (6d) or (6f) is hybridzed in reaction (5a) to the hybridization sequence (2d) of the cDNA. After washing and denaturation, as many as three of the primer molecules mentioned are bound to the reporter probe (6) in reaction (5b); DNA synthesis (7) follows complementarily to (6e), (6c), and (6a). The product of this reaction consists of three fragments bound to the reporter probe, each of which is separated from the other by a nick, (6b) (6c), (6d) (6e) and (6f) (6g); these are ligated by adding the ligase (11). This version would be simplified further by deleting the functional sequences (6e) and (6f) from the reporter probe, as described above. In this case only two, not three, fragments would be produced, ligated and then amplified further.

Organization of the Pert Assay when using an Amplification Procedure Based on Transcription These variants of the PERT assay again are based on the synthesis of a cDNA from a primed template nucleic acid by means of the RT activity in the sample. Wherever nothing else is mentioned, it is preferable to use a pure RNA as template nucleic acid. The sequence of the template nucleic acid to be amplified in step 2 must under no circumstances consist of DNA. It is important for the assay to eliminate the template RNA after the RT reaction. The nucleic acid to be amplified is contained in the cDNA or is synthesized in further reactions, starting from the cDNA. To this purpose an at least partially double-stranded DNA with a functional promoter for a DNA-dependent RNA polymerase (e.g. of the bacteriophage T7, T3 or SP6) is created, from this a RNA is then synthesized.

There are various possibilities for the construction of this DNA which contains a promoter and is at least partially double-stranded. The transcription promoter may be placed either close to the 5'-end of the cDNA or close to the 5'-end of the second DNA strand. In either of these cases the sequence information for the promoter may already be contained in the template nucleic acid, or it may be introduced by way of a primer. If the RT primer is used to this purpose the promoter is located close to the 5'-end of the cDNA. If however the primer for the second DNA strand is used the promoter is located close to the 5'-end of the second DNA strand.

Figure 8:
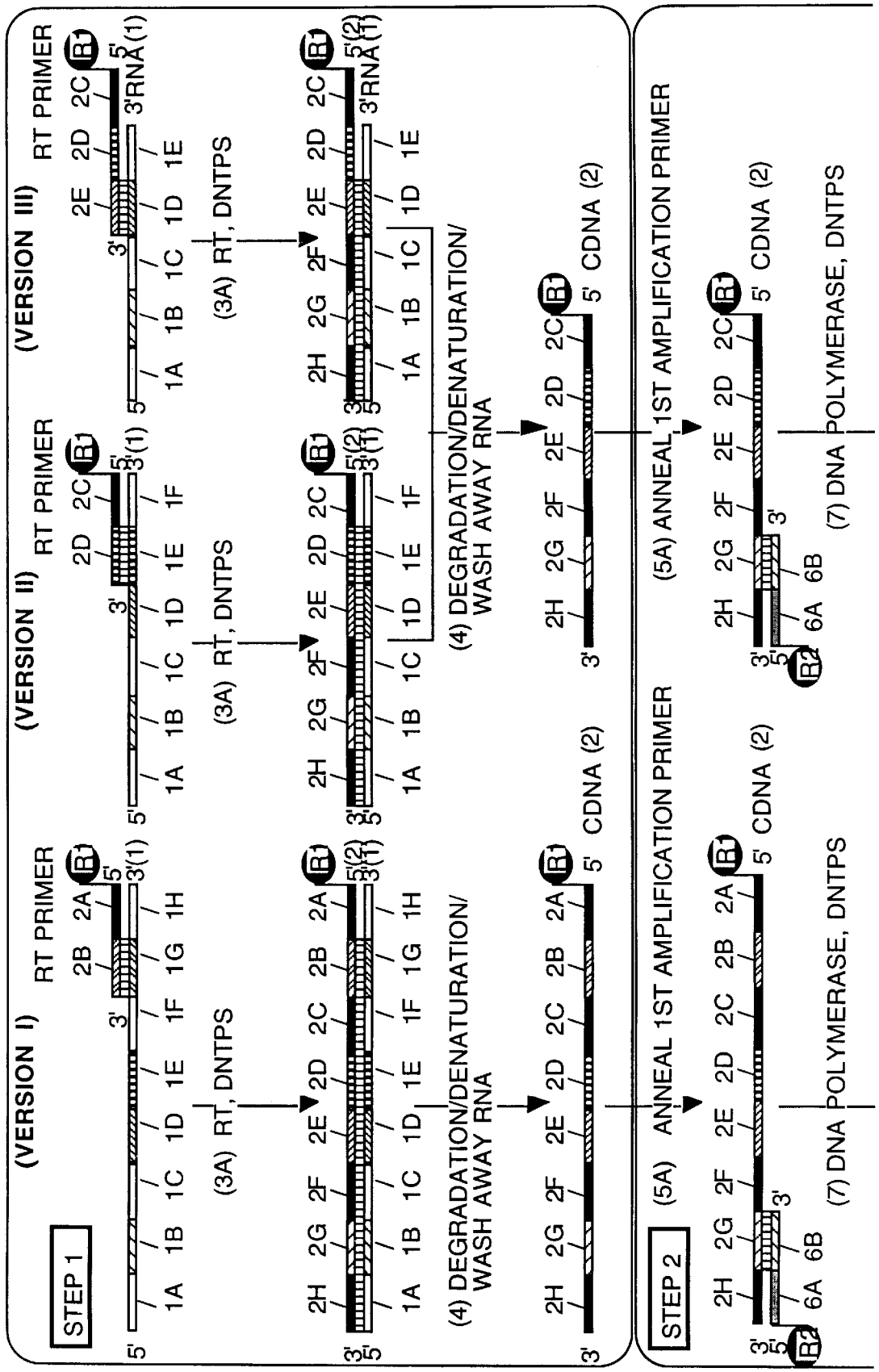
FIG. 8 shows the structure of the PERT assay in 3 illustrative versions, in which the cDNA contains the nucleic acid to be amplified, which is amplified by means of an isothermic multienzymatic amplification method.
Figure 9:
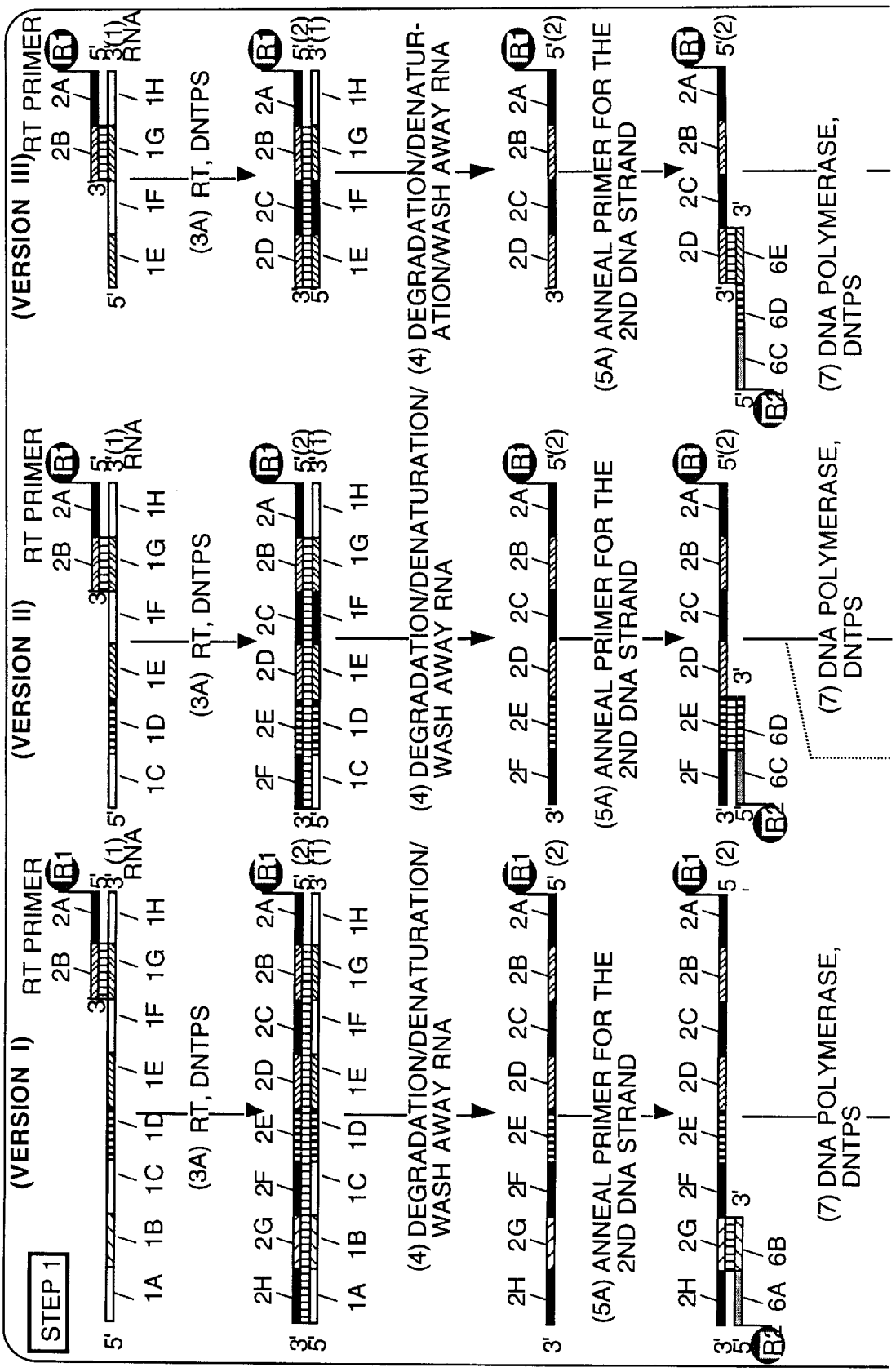
FIG. 9 shows the structure of the PERT assay in 3 illustrative versions, in which the nucleic acid to be amplified is a RNA derived from the cDNA, which RNA is amplified by means of an isothermic multienzymatic amplification method.

Prototypes of these two types of PERT assays are described in FIGS. 8 and 9.

Figure 10:
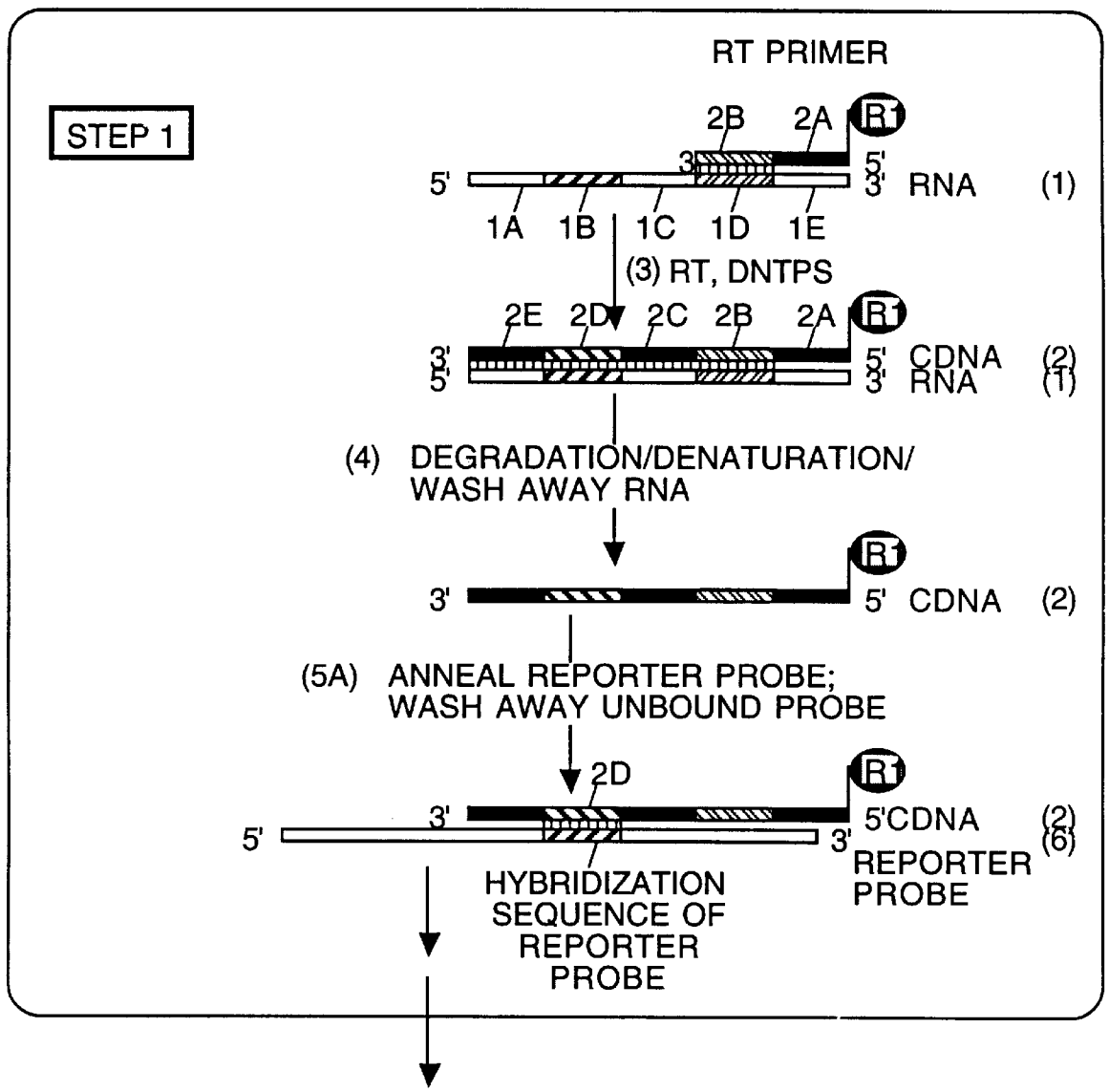
FIG. 10 shows the. structure of the PERT assay in an illustrative variant in which the nucleic acid to be amplified is a sequence of a reporter probe which sequence is amplified by means of an isothermic multienzymatic amplification method.

As with the variants of the PERT assay described above it is again possible to use a part of a reporter probe that is partially complementary to the cDNA, rather than the cDNA itself, for amplification. The reporter probe may consist of either DNA or RNA (FIG. 10). An RNA derived from a DNA reporter probe may also contain the nucleic acid to be amplified.

In all cases the amplification of the nucleic acid to be amplified is realized by means of a multi-enzymatic procedure in accordance to PS EP 0 408 295, WO 89/01050 and WO 88/10315. In PS EP 0 408 295, but not in the other two, this procedure will be isothermic.

FIG. 8 shows various versions of the PERT assay in which the cDNA synthesized in the RT reaction contains the nucleic acid to be amplified. In all these versions the cDNA synthesized in reaction (3a) contains the P(−) sequence of a transcription promoter close to its 5'-end. The transcription promoter sequence may be either already part of the template nucleic acid (versions I and II) or/and may be added by means of a RT primer (versions II and III). If integrated in the template nucleic acid it corresponds to the (P+) sequence of the promoter. If it is part of the RT primer it corresponds to the (P−) sequence.

Step 1: Version I: A template nucleic acid is used which contains the functional sequences (1a) (1b) (1c) (1d) (1e) (1f) (1g) (1h). Of these (1b), (1d) and (1g) are necessary hybridization sequences. (1e) is also necessary, it codes for the promoter for the chosen DNA-dependent RNA polymerase. The spacer sequences (1c) and (1f) and the flanking sequences (1a) and (1h) are facultative. Of the three hybridization sequences (1g) is used for the annealing of the RT primer. The hybridization sequence (1b), in its complementary form (2g), is used in step 2 for the annealing of the first amplification primer needed for the synthesis of the second DNA strand, as [hybridization sequence] (10c) it is used for amplification by annealing the first amplification primer. (1d) resp. the corresponding (6d) are used for the annealing of the second amplification primer in step 2.

The RT primer (R1) (2a) (2b) binds to (1g) of the template nucleic acid by means of the necessary hybridization sequence (2b). (2a), which is located at the 5'-end, is facultative and can be used, provided the RT primer is a DNA oligonucleotide, for introducing a new sequence not yet part of the template nucleic acid. R1 is facultative.

If RT activity is present in the pretreated sample, a cDNA (2) containing, as a maximum, the functional sequences (2a) to (2h), is synthesized in reaction (3a) by using dNTPs. The PERT assay can only succeed if at least all sequences up to and including (2g) are synthesized in the RT reaction.

Version II: A template nucleic acid is used that consists of (1a) (1b) (1c) (1d) (1e) (1f); in contrast to version I (1g) and (1h) have been deleted. (1b), (1d) and (1e) are necessary hybridization sequences. (1e) also contains the sequence of the transcription promoter endoded in RNA; the sequence for the annealing of the primer may reach beyond one or both sides of the sequence encoding the promoter. The spacer sequence (1c) as well as the flanking sequences (1a) and (1f) are facultative. Of the three hybridization sequences (1e) is used for the annealing of the RT primer. (1b) and (1d) serve the same function as in version I. As the template nucleic acid has been shortened compared to version I, the RT primer, a DNA oligonucleotide (R1) (2c) (2d), is not identical to the one used in version I. (2d), which is located at the 3'-end, mediates the annealing to (1e) of the nucleic template acid (1) and also contains the (P−) sequence of the transcription promoter. (2d), the sequence that is used for the annealing, may again, as in the case of (1e), reach beyond the promoter sequence on one or on two sides. (2c), at the 5'-end, is facultative and serves the function of (2a) in version I. (R1) is facultative. The product resulting from the RT reaction (3a) is a cDNA (2) which consists of, at a maximum, the functional sequences (2c) to (2h). If the PERT is to succeed, at least the sequences up to and including (2g) must be synthesized in the RT reaction.

Version III: A template nucleic acid is used that contains the functional sequences (1a) (1b) (1c) (1d) (1e); in contrast to version II the sequence used for the coding of the transcription promoter has also been deleted. (1b) and (1d) are necessary hybridization sequences. The spacer sequence (1c) and the two flanking sequences (1a) and (1e) are facultative. Of the two hybridization sequences (1d) is used for the annealing of both the RT primer and the second amplification primer. (1b) serves the same function as in version I. The transcription promoter sequence which is missing in the template nucleic acid is added by means of the RT primer. This RT primer, a DNA oligonucleotide (R1) (2c) (2d) (2e), has an obligatory hybridization sequence (2e) located at the 3'-end, which mediates the annealing of (1d) to the template nucleic acid (1). Upstream and adjacent to this is (2d) which contains the (P−) sequence of the transcription promoter. (2c), which is located at the 5'-end, is as in version II. (R1) is facultative. The product of the RT reaction (3a) is a cDNA consisting, as a maximum, of the functional sequences (2c) to (2h). For the PERT assay to succeed, at least the sequences up to and including (2g) are to be synthesized in the RT reaction.

All versions: In all three versions the template nucleic acid (1), which consists of RNA, is at first degraded in reaction (4) using one of the methods described above and thus eliminated as a participant in any of the later reactions. The single-stranded cDNA (2), which is not affected by these measure, contains the nucleic acid to be amplified in its sequences (2e) to (2g).

Step 2: The cDNA (2) is then introduced into a reaction mixture, according to the instructions contained in the patents listed initially and containing several enzymes, these are the DNA-dependent RNA polymerase matching the chosen promoter, a DNA-dependent DNA polymerase and a RNA-dependent DNA polymerase (RT). If the latter should not have sufficient RNase H activity, additional RNase H may be added. Before or during the introduction to the reaction mixture the stability of RNA must be ensured by one of the methods mentioned.

In all versions the first amplification primer, a DNA oligonucleotide (R2) (6a) (6b), is hybridized to the cDNA in reaction (5a). (R2) is preferably different from (R1) and not a carrier. The obligatory hybridization sequence (6b), which is located at the 3'-end of the primer, is in all versions complementary to (2g) of the cDNA (2). The facultative and non-complementary (6a), located at the 5'-end, can be used for the introduction of a new sequence not yet contained in the cDNA. By means of the DNA-dependent DNA polymerase contained in the reaction mixture and by using dNTPs the second DNA strand is synthesized in reaction (7); the result is a partially double-stranded DNA (2)//(6). In version I this consists of (R1) (2a) to (2h)//(R2) (6a) to (6h), in versions II and III of (R1) (2c) to (2h)//(R2) (6c) to (6h).

The dsDNA (2)//(6) added to the reaction mixture, which in (2d)//(6e) presents a functional promoter for the selected RNA polymerase in all three versions, is then used in reaction (8) by means of the DNA-dependent RNA polymerase and by using rNTPs for the synthesis of a ssRNA species (10) which contains (10a) (10b) (10c) (10d). This ssRNA (10) has the polarity of the cDNA in all three versions; (10a), (10b) and (10c) are complementary to (1d), (1c) and (1b) of the various template RNAs (1). (10d), on the other hand, is derived from (6a).

Based on the ssRNA(10), the following reactions rebuild, through a RT reaction, a dsDNA (11)//(6) that can be transcribed. First, in reaction (5b), the first amplification primer (R2) (6a) (6b) is annealed to the ssRNA (10); the entire DNA sequence of the oligonucleotide (R2) (6a) (6b) is used for the annealing.

By means of the RT in the reaction mixture, and by using dNTPs, the cDNA (R2) (6a) (6b) (6c) (6d) is then synthesized in reaction (3b). Due to the RNase H activity of the RT or, if necessary, due to the activity of added RNase H, the RNA (10) of the cDNA-RNA heteroduplex is then degraded in reaction (12) to such a degree that it becomes possible to carry out the annealing of the second amplification primer (R3) (11a) (11b) (11c) to (6d) of the cDNA in reaction (5c). This amplification primer consists at its 3'-end of an obligatory hybridization sequence (11c) that is complementary to (6d). Upstream of this follows the obligatory functional sequence (11b) for the (P−) sequence of the RNA polymerase promoter; (11a) is a facultative flanking sequence at the 5'-end. (R3) is also facultative.

Due to the renewed action of the DNA-dependent polymerase and by using dNTPs reaction (7) produces the dsDNA (11)//(6). Strand (11) contains elements (R3) (11a) to (11f), strand (6) contains elements (R2) (6a) to (6f). This dsDNA again has in (11b)//(6e) a functional promoter for the RNA polymerase, thus the ssRNA (10a) (10b) (10c) (10d) is again synthesized in reaction (8). The ssRNA (10) is again introduced into the amplification cycle and is the principal product of step 2.

Step 3: The ssRNA (10a) (10b) (10c) (10d) resulting from the amplification process is used for the analysis according to the general remarks concerning step 3 below.

Modifications

All functional sequences and functional groups (R) of the various nucleic acids used that have been identified as facultative may be omitted, whether individually or in the various combinations possible. Omitting the functional sequence that is located at the 5'-end of the RT primer [(2a) in version I; (2c) in versions II and III] does not affect the composition of the ssRNA produced in step 2. Omitting sequence (6a) of the first amplification primer means that sequence (10d) at the 3'-end of the ssRNA (10) is missing. On the other hand, omitting (1a) of the template nucleic acid and/or (11a) of the second amplification primer, does not influence the composition of the ssRNA (10). In reaction (4) the presence of (R1) may be of advantage.

An additional spacer sequence can be inserted in the template nucleic acid between elements (1d) and (1e), in the RT primer between (2d) and (2e), and/or in the second amplification primer between (11b) and (11c).

In version III any base sequences are possible for the two flanking sequences of the template nucleic acid (1); it is therefore possible to use natural RNA molecules as template nucleic acid (1).

In deviation from the norm a functional sequence, or a combination of functional sequences, may serve more than one function. Thus in all versions the second amplification primer (R3) (11a) (11b) (11c) may also exert the function of the RT primer. In this case the annealing of the RT primer by means of the hybridization sequence (11c) is to the hybridization sequence (1d) of the template nucleic acid (1). In this case, a template nucleic acid (1) consisting at its 3'-end of the sequences up to and including (1d) is sufficient for successful operation of the PERT assay.

On the other hand, a RNA primer may be used for the RT reaction by using different molecules for the RT primer and the second amplification primer, thus the sensitivity and/or the specificity of the PERT assay can be influenced.

In deviation from the norm it is possible to use identical base sequences for various functional sequences, these may also be homopolymeric. In all versions this is the case for the flanking or the spacer sequences of the template nucleic acid (1), which can be homopolymeric and/or identical to each other.

Furthermore it is possible to modify these versions in such a way that the transcription promoter is located towards the 5'-end of the 2nd DNA strand. In this case the ssRNA (10) synthesized in step 2 has the same polarity as the template nucleic acid (1). The transcription promoter sequence may, as a P(−) sequence, be introduced by the template nucleic acid, in this case it must be located upstream of the hybridization sequence (1b). In all cases, however, the amplification primer used for the synthesis of the 2nd DNA strand must, upstream of the hybridization sequence located at the 3'-end, contain the P(−) sequence of a transcription promoter. If the transcription promoter sequence for the synthesis of the 2nd DNA strand is exclusively introduced through the primer, a natural RNA may be used as template nucleic acid. In order to construct the partially double-stranded DNA containing a functional promoter, denaturation of the DNA after the synthesis of the 2nd DNA strand is unavoidable in this case; thus a functional promoter can be constructed through the annealing of the first amplification primer and renewed DNA synthesis. In this case the cDNA (2) synthesized through the RT activity only presents the educt for the synthesis of the nucleic acid to be amplified. The ssRNA (10) synthesized in step 2 will then show the same polarity as the template nucleic acid (1).

FIG. 9 describes various versions of the PERT assay where the nucleic acid to be amplified is a RNA. The transcription promoter necessary for the synthesis of this RNA is located near the 5'-end of the second DNA strand in all versions shown. The transcription promoter sequence may already be part of the template nucleic acid as (P−) sequence (versions I and II), or it may be added by means of the primer for the second DNA strand, again corresponding to a (P−) sequence.

Step 1: Version I: A template nucleic acid containing the functional sequences (1a) to (1h) is used. Of these (1b), (1e) and (1g) are necessary hybridization sequences. (1d), which codes for the transcription promoter, is also necessary. The spacer sequences (1c) and (1f) as well as the flanking sequences (1a) and (1h) are facultative. Of the three hybridization sequences (1g) is used for the annealing of the RT primer, and in step 2 (13d), which is derived from (1g), serves the annealing of the first amplification primer. (1b), in its complementary form (2g), is used for the annealing of the primer for the second DNA strand in step 1. (1e), in its complementary form (14b), is used for the annealing of the second amplification primer in step 2. The RT primer (R1) (2a) (2b) is a RNA or a DNA oligonucleotide. At its 3'-end, the obligatory (2b) mediates the annealing of (1g) to the template nucleic acid. The functional group (R1) is facultative. If RT activity is present in the pretreated sample, the necessary dNTPs are used in reaction (3a) in order to synthesize a cDNA (2) containing, as a maximum, the functional sequences (2a) to (2h). For a successful application of the PERT assay at least all sequences up to and including (2g) must be synthesized in the RT reaction (3a).

Version II: A template nucleic acid containing (1c) (1d) (1e) (1f) (1g) (1h) is presented; in contrast to version I (1a) and (1b) have been deleted. The remaining sequences are used as has been described for version I, the only exception being that (1c) now is a flanking sequence. The RT primer (R1) (2a) (2b) also is identical to version I. If RT activity is present in the pretreated sample the necessary dNTPs are used in reaction (3a) to synthesize a cDNA (2) containing, as a maximum, the functional sequences (2a) to (2f). For a successful application of the PERT assay at least all sequences up to and including (2e) must be synthesized.

Version III: A template nucleic acid containing (1e) (1f) (1g) (1h) is presented; in contrast to version II (1c) and (1d) have been deleted. The remaining functional sequences are used as has been described for version I. The RT primer (R1) (2a) (2b) also is the same as in version I. If RT activity is present in the pretreated sample the necessary dNTPs are used in reaction (3a) for the synthesis of a cDNA (2) containing, as a maximum, the functional sequences (2a) to (2d). For a successful application of the PERT assay sequences (2c) and (2d) must be synthesized in the RT reaction.

All versions: In reaction (4) the RNA is eliminated as a participant in the reactions that follow by using one of the methods mentioned in FIG. 2.

In version I the primer for the second DNA strand, a DNA oligonucleotide (R2) (6a) (6b), is then hybridized to the cDNA (2) in reaction (5a). Its obligatory hybridization sequence (6b), which is located at the 3'-end, is complementary to (2g) of the cDNA. (6a), which is located at the 5'-end, is facultative, it is not complementary to the cDNA and is used for introducing a new sequence not yet contained in the cDNA. By adding a DNA-dependent DNA polymerase and by using dNTPs the second DNA strand (6) is synthesized in reaction (7); the result is a dsDNA (2)//(6) that consists of (R1) (2a) to (2h)//(R2) (6a) to (6h).

In version II the primer used in version I is replaced by a DNA oligonucleotide primer (R2) (6c) (6d) that corresponds to the shortened 3'-end of the cDNA, this is hybridized to the cDNA (2) resulting from step 1. Its obligatory hybridization sequence (6d), located at the 3'-end, is complementary to (2e) of the cDNA and also contains the (P−) sequence of the chosen transcription promoter. The hybridization sequence may overlap with the transcription promoter sequence on both sides. (6c) at the 5'-end is facultative, not complementary to the cDNA and is used for introducing a new sequence not yet contained in the cDNA. By adding a DNA-dependent DNA polymerase and by using dNTPs the second DNA strand (6) is synthesized in reaction (7); the result is a dsDNA (2)//(6) consisting of (R1) (2a) to (2f)//(R2) (6c) to (6h). If the 3'-end of (6d) reaches beyond the 3'-end of the polymerase promoter sequence by at least 3 nucleotides, a functional promoter for the RNA polymerase already results from the annealing of the primer (R2) (6c) (6d) to the cDNA; in this case reaction (7) is no longer necessary for the RNA synthesis (8a).

In version III a DNA oligonucleotide primer (R2) (6d) (6d) (6e) corresponding to the even shorter 3'-end of the cDNA is hybridized to the cDNA (2) in reaction (5a). The obligatory hybridization sequence (6e) located at the 3'-end of the primer (R2) (6c) (6d) (6e) is complementary to (2d) of the cDNA. (6c) and (6d) are identical to version II. By adding a DNA-dependent DNA polymerase and by using dNTPs the two 3'-ends of the two DNA strands are extended in reaction (7); the result is a dsDNA (2)//(6) consisting of (R1) (2a) to (2f)//(R2) (6c) to (6h).

In all versions this is the latest possible time to re-establish conditions that guarantee the stability of the RNA in the reactions that follow. The methods used to this purpose are the same as in FIG. 8.

The dsDNA (2)//(6) added to the reaction mixture, which in all three versions contains, in (2e)//(6d), a functional promoter for the chosen RNA polymerase, is used in reaction (8a), by means of the DNA-dependent RNA polymerase and by using rNTPs, for the synthesis of a ssRNA species (10) containing (10a) (10b) (10c) (10d). In all three versions, this ssRNA (10) has the polarity of the second DNA strand (6) resp. of the template nucleic acid (1); (10a), (10b) and (10c) are identical to (1e), (1f) and (1g) of the various template RNAs (1). (10d), however, is derived from (2a) and complementary to it.

Step 2: The ssRNA (10) is added to the amplification procedure. In a first annealing reaction (5b), the first amplification primer (R3) (11a) (11b) (11c) is hybridized to (10c) of the ssRNA through the hybridization sequence (11c) located at the 3'-end. (11b) is a P(−) sequence of a transcription promoter, and (11a) is a flanking sequence. (11b) and (11c) are necessary, (11a) and the functional group (R4) are facultative. By means of the RT in the reaction mixture the cDNA (R3) (11a) (11b) (1c) (11d) (11e) is synthesized in reaction (3b) by using dNTPs. Due to the RNase H effect of the RT or, if necessary, due to the effect of any additional RNase H, the RNA (10) is degraded in reaction (12) from the cDNA-RNA heteroduplex to such a degree that it becomes possible to proceed with the annealing of the second amplification primer (R4) (13a) (13b), to (11e) of the cDNA in reaction (5c). At its 3'-end this amplification primer consists of an obligatory hybridization sequence (13b) that is complementary to (11e). Upstream of this is the facultative flanking sequence (13a). (R4) also is facultative. Through renewed action of the DNA-dependent DNA polymerase and by using dNTPs reaction (7) results in a dsDNA (11)// (13); by means of a RNA polymerase and by using rNTPs this is then used in reaction (8b) for the synthesis of a ssRNA (14), which is complementary to (10d), (10c) and (10b) in its sequences (14a), (14b) and (14c).

Starting with the RNA (14) a dsDNA is rebuilt. The second amplification primer (R4) (13a) (13b) is hybridized to the RNA in an annealing reaction (5c). By means of the RT in the reaction mixture and by using dNTPs, the cDNA (R4) (13a) (13b) (13c) (13d) is synthesized in reaction (3b). Due to the RNase H activity of the RT or, if necessary, due to the activity of additional RNase H, the RNA (14) is then degraded from the cDNA-RNA heteroduplex in reaction (12) to such a degree that the annealing of the first amplification primer (R3) (11a) (11b) (11c) to (13d) of the cDNA can then follow in reaction (5b). Following renewed action of the DNA-dependent DNA polymerase and by using dNTPs reaction (7) again yields a dsDNA (11)//(13), which is used in reaction (8b), by means of a RNA polymerase and by using rNTPS, for the synthesis of the ssRNA (14).

Step 3: The ssRNA (14a) (14b) (14c) (14d) resulting from the amplification process is used for the analysis according to the general remarks on step 3 below.

Modifications

All functional sequences and functional groups (R) of all nucleic acids used that have been identified as facultative can be omitted, either individually or in any of the various possible combinations. If the functional sequence (2a) located at the 5'-end of the RT primer is omitted, the result in all versions is that (10d) of the ssRNA (10) is missing. However, omitting the functional sequence located at the 5'-end of the primer for the 2nd DNA strand [(6a) for version I, (6c) in versions II and III] does not affect the composition of the ssRNA (10) synthesized in step 2. Omitting (11a) of the first amplification primer does not affect the composition of the ssRNA (14); on the other hand, if (13a) is missing, the sequence (14d) is no longer present in the ssRNA (14) transcribed from the dsDNA (11)//(13). In reaction (4) the presence of (R1) may be of advantage.

It is possible to insert an additional spacer element in the template nucleic acid between the elements (1d) and (1e), in the primer for the second DNA strand between (6d) and (6e), and/or in the second amplification primer between (11b) and (11c).

In version III the flanking sequence (1h) at the 3'-end of the template nucleic acid (1) may show any base sequence. It is therefore possible to use natural RNA molecules as the template nucleic acid (1).

In deviation from the norm a functional sequence, or a combination of functional sequences, may serve more than one function. Thus in all versions the first amplification primer (R3) (11a) (11b) (11c) may also take the function of the RT primer. In this case the annealing of the RT primer, by means of (11c), is to (1g) of the template nucleic acid (1).

On the other hand, if different molecules are used for the RT primer and for the first amplification primer, this also allows using an RNA primer for the RT reaction, thus the sensitivity and/or the specificity of the PERT assay may be influenced.

In deviation from the norm it is possible to use identical base sequences for various functional sequences, these may also be homopolymeric. In all versions this is the case for the flanking and the spacer sequences of the template nucleic acid (1), which may be homopolymeric and/or identical to each other.

A further possible modification is to construct in step 1 a dsDNA (2)//(6) that carries one functional transcription promoter each on both ends. Thus two different species of ssRNAs are produced, these overlap in part and have opposite polarity.

Based on version II it is possible, when using a template nucleic acid that, in addition to the template RNA, also contains a template DNA, to achieve a procedure that is considerably simpler: A template nucleic acid (1c) (1d) (1e) (1f) (1g) (1h) is presented, of which (1d) and at least the three first nucleotides of (1e) consist of DNA, the rest of (1e) and (1f), however, of RNA. Whether they consist of DNA or RNA does not matter for the other functional sequences. By using the RT primer (R1) (2a) (2b) a double-stranded nucleic acid is synthesized in the RT reaction, this double-stranded nucleic acid has a functional transcription promoter in the dsDNA (1d)//(2e), which can then, after having been added to the reaction mixture used in step 2, be used for the direct synthesis of the RNA (10a) (10b) (10c) (10d). However, in this version too it is again necessary to eliminate the template nucleic acid before introducing the reaction mixture used into step 2.

FIG. 10. Amplification by means of a reporter probe Step 1. The template-primer combination, the RT reaction (3) and its product are in all aspects identical to those in FIG. 3. In reaction (4) the template nucleic acid, the RNA (1), is eliminated as a relevant participant in the annealing reaction (5a) by using one of the methods mentioned. In reaction (5a) a reporter probe (6) is hybridized to the cDNA. Requirements and possibilities for this correspond to those in PS FP 0 408 295; DNA or RNA reporter probes may be used. It is necessary that one hybridization sequence of the reporter probe (6) is complementary to the hybridization sequence (2d) of the cDNA (2), thus making the annealing possible. No later than after the reporter probe (6) has been hybridized to the cDNA (2) the cDNA is bound to a carrier by means of the functional group (R1); unbound reporter probe must be entirely eliminated from the reaction mixture under non-denaturing conditions, as describe in FIG. 3. As explained in FIG. 8, no later than after the unbound reporter probe has been washed out reaction conditions have to be established that allow the amplification of at least a partial sequence of a reporter probe (6) in accordance with PS EP 0 408 295. The main product yielded by the amplification is a ssRNA, which is to be analyzed as described in FIGS. 8 and 9.

Modifications

All possibilities mentioned in FIG. 3 for the choice of the template nucleic acid and of the RT primer are available. However, it is important to ensure that neither the template nucleic acid nor the RT primer show any sequence homology or complementarity to the reporter probe, the only exception being the sequence used for the hybridization of the reporter probe.

The efficiency of the initial synthesis of a RNA can be increased by a modification in which the hybridization sequence (1b) of the template nucleic acid (1) also contains the P(+) sequence of a transcription promoter. The reporter probe used in this case is a nucleic acid whose hybridization sequence is designed in a way so that it hybridizes with both (2d), which presents the P(−) sequence of the transcription promoter, and also (2e). Upstream of this double hybridization sequence the reporter probe contains a spacer sequence, then another hybridization sequence. All three functional sequences consist of DNA, thus the hybridization of the reporter probe to the cDNA results in a transcription promoter that is used, after the addition of RNA polymerase, for the synthesis of the ssRNA to be amplified.

Procedure of the Pert Assay when using an Amplification Procedure Based on Replicative RNA These PERT variants use an in vitro replication system for the amplification of a primary replicative RNA. The functional sequences of a RNA necessary for the replication are here illustrated by using the example of the replication system of the bacteriophage Qb (beta), this being the best documented of such systems. If it is to serve as the template nucleic acid for the Qb replicase, the 3'-end of the primary RNA must have a region rich in cytidine (by definition a 3'-RNA-ori(+) sequence), which is needed for initiating the RNA replication. The 5'-end of the primary replicative RNA must contain a sequence rich in guanyl (by definition a 5'-ori(−) sequence), which in its complementary sequence represents a cytidine-rich region and which initiates the RNA synthesis of the complementary strand. The RNA segments located between the two terminal replication initiation sequences also must have a replicase binding domain, that is a discontinuous sequence element necessary for the binding of the RNA replicase. The presence of this type of RNA in combination with Qb replicase and the necessary rNTPs in a reaction mixture results in an autocatalytic amplification of the RNA molecule with a doubling time of less than a minute. Besides the Qb replication system it is also possible to use replication systems of other RNA phages in an analogous manner. To quote but a couple of examples, those of the phages MS2, f2, and R17 can be used.

On the one hand, the PERT assay may be adapted to this replication system by using template nucleic acids that have been derived from replicative RNAs and/or whose base sequence is at least in part integrated into the primary replicative RNA, which is then in step 2 amplified by means of RNA replicase. On the other hand, the cDNA synthesized in the RT reaction may be used, with the help of a reporter probe, to prepare a primary replicative RNA as the nucleic acid to be amplified. If nothing else is mentioned, pure RNAs are preferred as template nucleic acids in the illustrated variants that follow.

If template nucleic acids are used that have been derived from replicative RNAs, a first step is to first synthesize a DNA at least partially double-stranded, which in direct conjunction to a transcription promoter contains all necessary functional sequences of a replicative RNA. This at least partially double-stranded DNA is then used, with the help of a DNA-dependent RNA polymerase, for the synthesis of a replicative RNA, which in step 2 is amplified by means of the corresponding replication system. It is important to choose the template nucleic acid sequence and the primer sequence in such a way that the succession of enzymatic reactions only results in the synthesis of an amplifiable RNA if a RT activity present in the sample has synthesized a cDNA in step 1. Measures must be taken that prevent the replication of the template nucleic acid in step 2, thus precluding any false-positive or false-negative results (depending on the type of analysis of the amplification product both are possible). The following variants (FIG. 11–17) describe the large variety of possibilities for a PERT assay based on this reaction principle.

Figure 11:
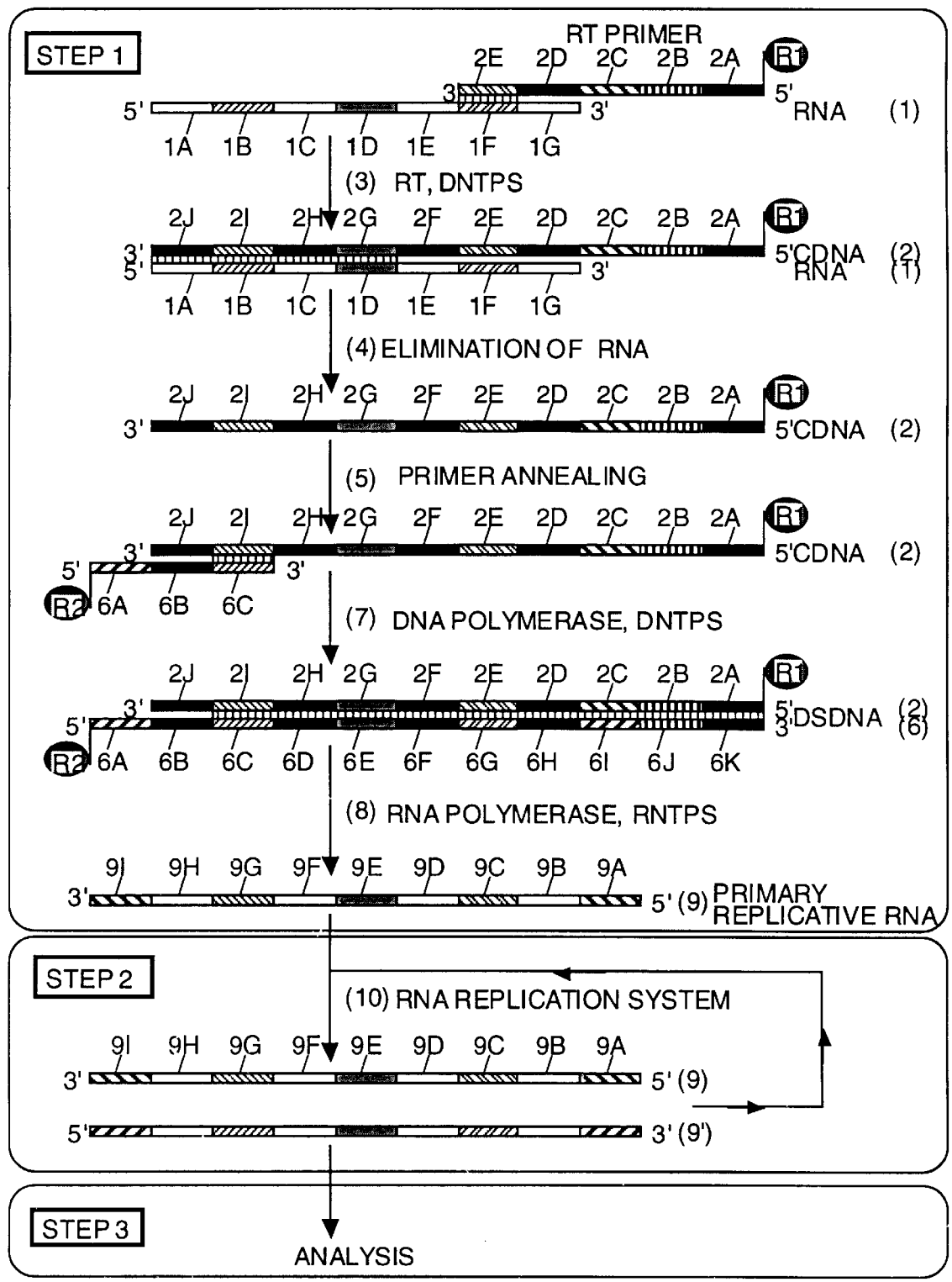
FIGS. 11–14 show the structure of the PERT assay in 4 illustrative variants, in which the nucleic acid to be amplified is a primary replicative RNA at least in part derived from the sequence of the cDNA, which replicative RNA is amplified by means of a suitable RNA replication system.

FIG. 11 shows a first possible reaction sequence of such a PERT assay. The necessary functional sequences for the later RNA synthesis and its amplification, with the exception of the replicase binding domain, are introduced into the DNA by ssDNAs. The transcription promoter sequence is introduced close to the 5'-end of the cDNA by means of the RT primer. The primary replicative RNA synthesized at the end of step 1 has a polarity opposite to the template nucleic acid.

Step 1: The template nucleic acid (1) consists of the following functional sequences: a flanking sequence (1a) at its 5'-end, the hybridization sequence (1b), two spacer sequences (1c) resp. (1e), the replicase binding domain (1d), a second hybridization sequence (1f) for the annealing of the RT primer, and the flanking sequence (1g) at the 3'-end. The flanking sequences (1a) and (1g) and the spacer sequences (1c) and (1e) are facultative; all other sequences are necessary.

A ssDNA (R1) (2a) (2b) (2c) (2d) (2e), preferably an oligonucleotide, functions as the RT primer. This ssDNA contains the P(−) sequence of a transcription promoter in (2b), adjacent to this is the 5-ori(−) sequence (2c), and at its 3'-end there is the hybridization sequence (2e) for the hybridization to (1f) of the template nucleic acid (1). (2a) and (2d) are a flanking, respectively a spacer sequence. (2b), (2c) and (2e) are necessary, (2a) and (2d) are facultative. (R1) is also facultative.

In reaction (3) the RT activity contained in the pretreated sample synthesizes a cDNA (2) containing (R1) (2a) (2b) (2c) (2d) (2e) (2f) (2g) (2h) (2i) (2j). The PERT assay can only succeed if all sequences up to (2g) are synthesized.

The mixture of nucleic acids resulting from reaction (3) is modified in reaction (4) in such a way that none of the components may interfere in an undesirable manner with an optimal devlopment of the reactions that follow. Above all it is essential to prevent the template nucleic acid (1) and/or the template-primer combinations (1)//(R1) (2a) (2b) (2c) (2d) (2e) from competing with the hybridization (5) of the second primer (R2) (6a) (6b) (6c) to the cDNA (2), and to prevent, in step 2, the RNA replicase from binding to the template nucleic acid, which is available in abundance, rather than to the replicative RNA (9). Either of these would result in a diminished sensitivity of the assay or might even lead to false-negative results. This is the reason why the template nucleic acid (1), which consists of RNA, is eliminated in reaction (4) by using one of the methods mentioned above.

In reaction (5) follows the annealing of a second ssDNA (R2) (6a) (6b) (6c), preferably an oligonucleotide. The necessary sequences contained in this DNA are a 3'-ori(-) sequence (6a) at the 5'-end, and at the 3'-end a hybridization sequence (6c) for the hybridization to (2i) of the cDNA (2). Facultative elements are a spacer sequence (6b) and a functional group (R2). Through a DNA polymerase and by using dNTPs a dsDNA consisting of strands (2) and (6) is then synthesized in reaction (7), its segment (2b)//(6j) being the active transcription promoter for the RNA polymerase. As described in FIG. 8, this is the latest moment for re-establishing reaction conditions that ensure the stability of the RNA in the following reactions. After adding the RNA polymerase that corresponds to the transcription promoter, reaction (8), by using the necessary rNTPs, leads to the synthesis of the nucleic acid to be amplified, the primary replicative RNA (9), which has all functions necessary for the amplification in the chosen replication system. Its sequences (9c), (9d), (9e), (9f) and (9g), are complementary to sequences (1f), (1e), (1d), (1c), and (1b) of the template nucleic acid.

Step 2: This RNA (9) is now introduced into the RNA replication system (10). In a suitable buffer this contains all enzymes and other reagents such as rNTPs etc. that are needed for the RNA replication. The RNA is amplified within this replication system; thus single-stranded RNA molecules of both polarities are produced that are analyzed in step 3 with suitable methods.

Figure 12:
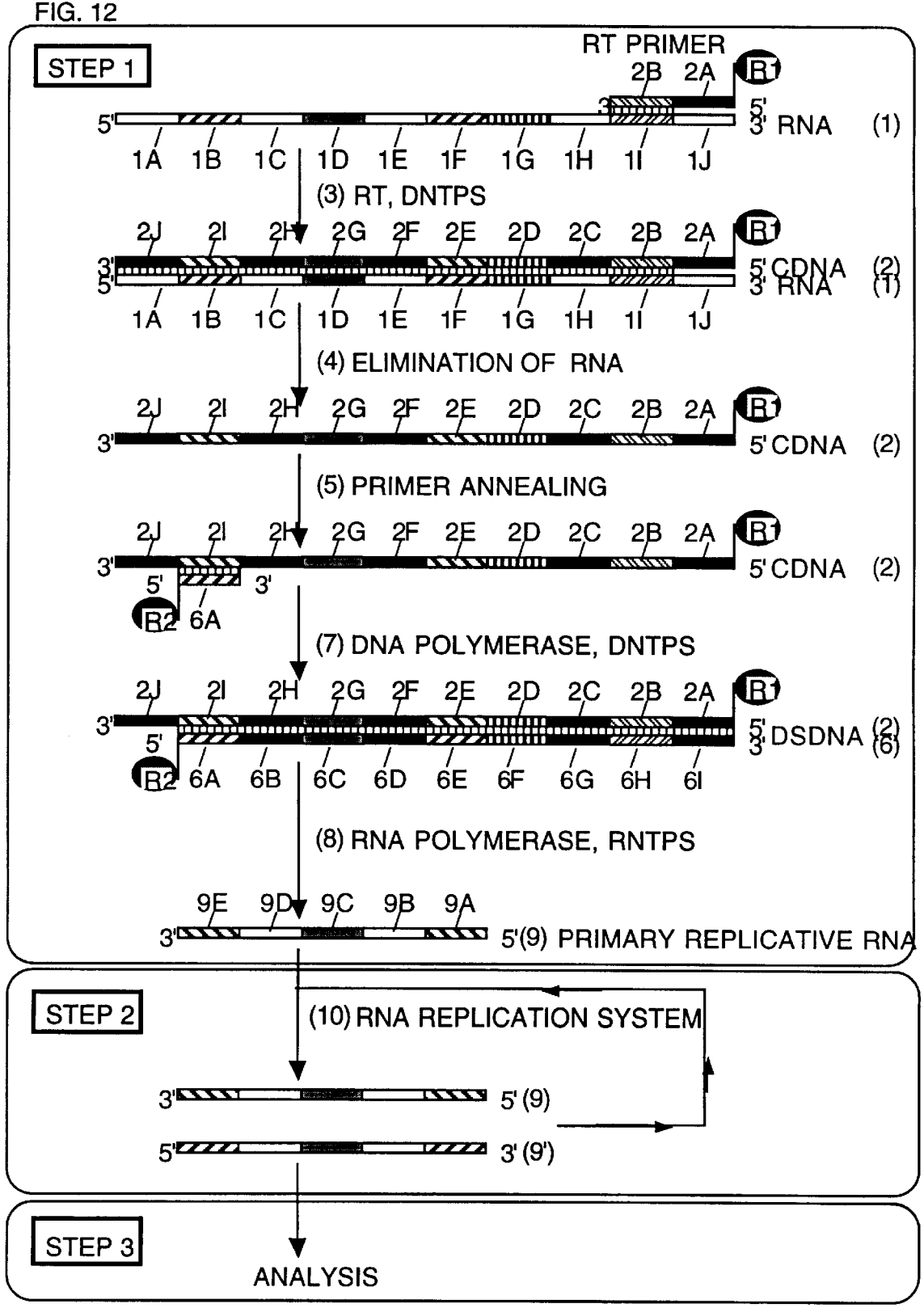

FIG. 12 shows a reaction procedure with a template nucleic acid that already contains all sequences needed for the later RNA synthesis and its amplification. The transcription promoter sequence is again located close to the 5'-end of the cDNA. The primary replicative RNA synthesized at the end of step 1 has a polarity opposite to the template nucleic acid.

Step 1: The template nucleic acid (1) contains the functional sequences (1a) . . . (1j). In deviation from the general principles in this variant the functional sequences (1b), resp. (6a), are given two functions.

In contrast to FIG. 11 the template nucleic acid (1) used codes for all functions needed for the transcription and replication of the RNA. (1b) contains a 3'-RNA-ori(-) sequence and is simultaneously a hybridization sequence; the sequence used for the hybridization may be longer than the RNA-ori sequence needed as a minimum for the replication, the condition being that the RNA-ori sequence forms the 5'-end of (1b). (1c), (1e) and (1h) are spacer sequences, (1d) the replicase binding domain, and (1f) is a 5'-RNA-ori(+) sequence. (1g) is the P(+) sequence of a transcription promoter, and (1i) is the hybridization sequence for the RT primer. (1a) and (2j) are flanking sequences. Both the flanking and the spacer sequences are facultative. All other functional sequences are necessary in this variant.

The RT primer (R1) (2a) (2b) is a nucleic acid, preferably a DNA or RNA oligonucleotide. It consists of the facultative functional group (R1), the facultative, non-hybridizing flanking sequence (2a), and the necessary hybridization sequence (2b) needed for the hybridization to (1g).

In reaction (3), the RT activity in the sample serves to synthesize a cDNA with, as a maximum, sequences (2a) (2b) (2c) (2d) (2e) (2f) (2g) (2h) (2i) (2j). The PERT assay can only be successful if at least all sequences up to (2i) are synthesized in the RT reaction.

As in FIG. 11 the template nucleic acid (1) is degraded in reaction (4). In reaction (5) follows the annealing of the second primer (R2) (6a), a DNA oligonucleotide. It consists of (6a), the hybridization sequence complementary to (2g), and contains a 3'-RNA-ori(-) sequence at the 5'-end. The functional group (R2) is facultative.

In reaction (7) a dsDNA, consisting of strands (2) and (6), is synthesized by means of a DNA polymerase. As described in FIG. 8 this is the latest moment for re-establishing conditions that ensure the stability of the RNA for the reactions that follow. This is followed by reaction (8), in which, by means of a RNA polymerase that corresponds to the transcription promoter, the primary replicative RNA (9) is synthesized. Its functional sequences (9a), (9b), (9c), (9d) and (9e) are complementary to (1f), (1e), (1d), (1c) and (1b) of the template nucleic acid.

Step 2: This RNA (9) is introduced into the RNA replication system (10) and amplified; single-stranded RNA molecules of both polarities result which, with the help of suitable methods, are analyzed in step 3.

Figure 13:
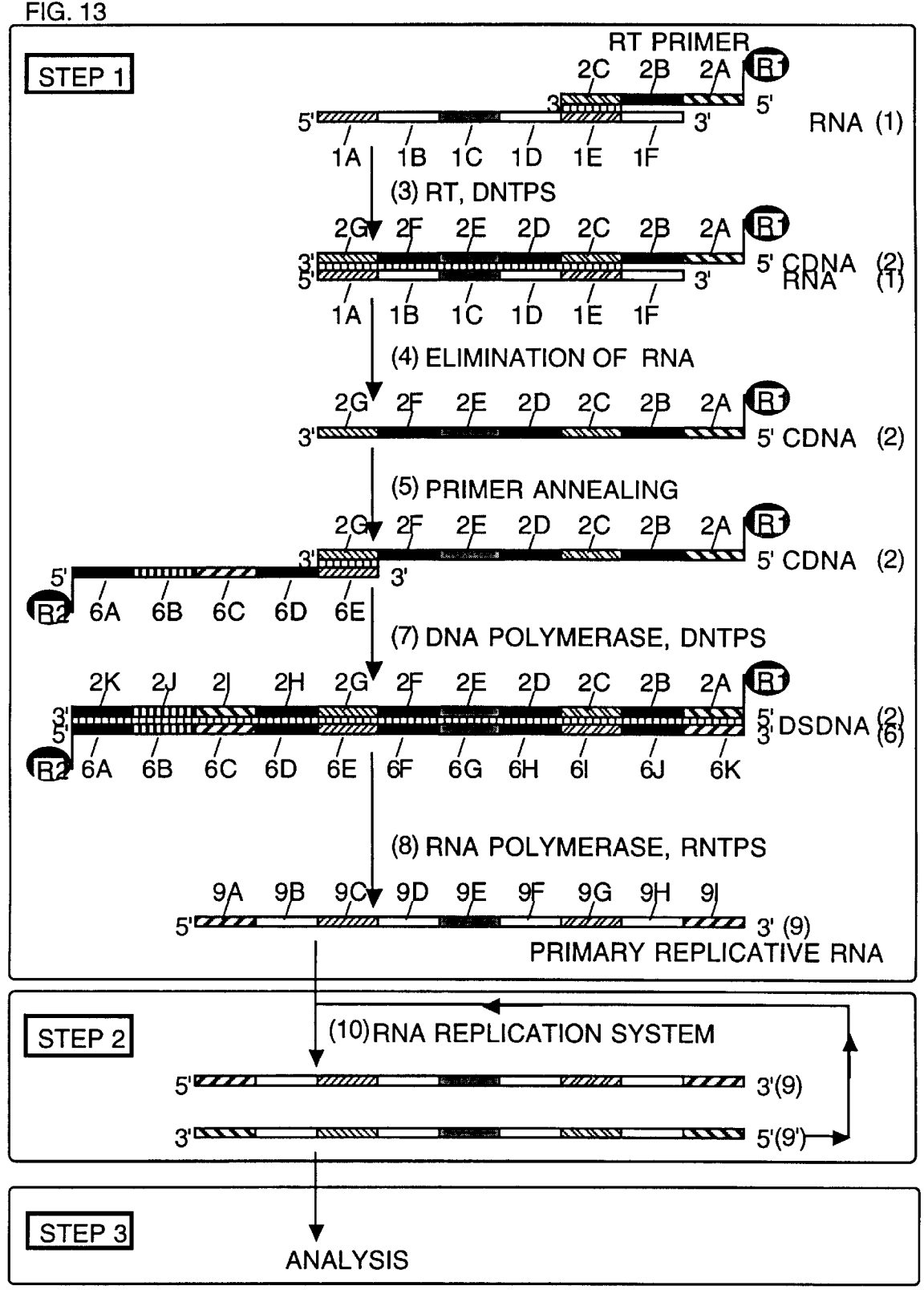

FIG. 13 shows another variant of the template primer configuration. The functional sequences necessary for the RNA synthesis and the amplification, with the exception of the replicase binding domain, are again exclusively introduced into the DNA by oligonucleotides. However, the transcription promoter sequence is introduced into the DNA by way of the second primer. The primary replicative RNA synthesized at the end of step 1 has the same polarity as the template nucleic acid.

Step 1: the template nucleic acid (1) presented consists of the following functional sequences, all of which are necessary for this variant to function: (1a), located at the 5'-end of the template nucleic acid (1), is a hybridization sequence, (1c) is the replicase binding domain, and (1e) is the hybridization sequence responsible for the annealing of the RT primer. Facultative are the spacer sequences (1b) and (1d) and the flanking sequence (1f).

The primer for the RT reaction (3) is a ssDNA (R1) (2a) (2b) (2c), preferably an oligonucleotide. It consists of (R1), the 3'-RNA-ori(-) sequence (2a), the spacer sequence (2b) and a hybridization sequence (2c) at its 3'-end that is complementary to (1c). Sequences (2a) and (2c) are necessary for the assay, the other two may be omitted.

In reaction 3, the RT activity in the sample synthesizes a cDNA consisting of (R1) (2a) (2b) (2c) (2d) (2e) (2f) (2g). All segments up to (2g) must be synthesized in the RT reaction for the PERT assay to function.

As in FIG. 11 the template nucleic acid, the RNA (1), is degraded in reaction (4). In reaction (5) the annealing of the second primer (R2)(6a) . . . (6e), a ssDNA, preferably an oligonuclotide, follows. It contains the P(-) sequence of the transcription promoter (6b) near its 5'-end, downstream of and adjacent to this follows a 5'-RNA-ori(-) sequence (6c). At the 3'-end of the primer is the hybridization sequence (6e), which is complementary to (2g) of the cDNA. (6b), (6c) and (6e) are necessary for this variant. In addition to these a flanking (6a) and a spacer sequence (6d) may be present as facultative elements. The primer may also contain a functional group (R2).

By means of a DNA polymerase and by using dNTPs a dsDNA consisting of strands (2) and (6) is synthesized in reaction (7). The segment (6b)//(2j) now represents an active transcription promoter. As described in FIG. 8, this is the latest possible moment for re-establishing conditions needed to ensure the stability of the RNA in the reactions that follow.

After adding the RNA polymerase and by using the necessary rNTPs the nucleic acid to be amplified, the primary replicative RNA (9), is now synthesized in reaction (8). This contains all functional sequences needed for the amplification within the chosen replication system. Its functional sequences (9c), (9d), (9e), (9f) and (9g) correspond to (1a), (1b), (1c), (1d), and (1e) of the template nucleic acid (1).

Step 2: The primary replicative RNA (9), which shows the same functional sequences as the primary replicative RNA in FIG. 11, is amplified in analogy to step 2/FIG. 11 and then analyzed in step 3.

Figure 14:
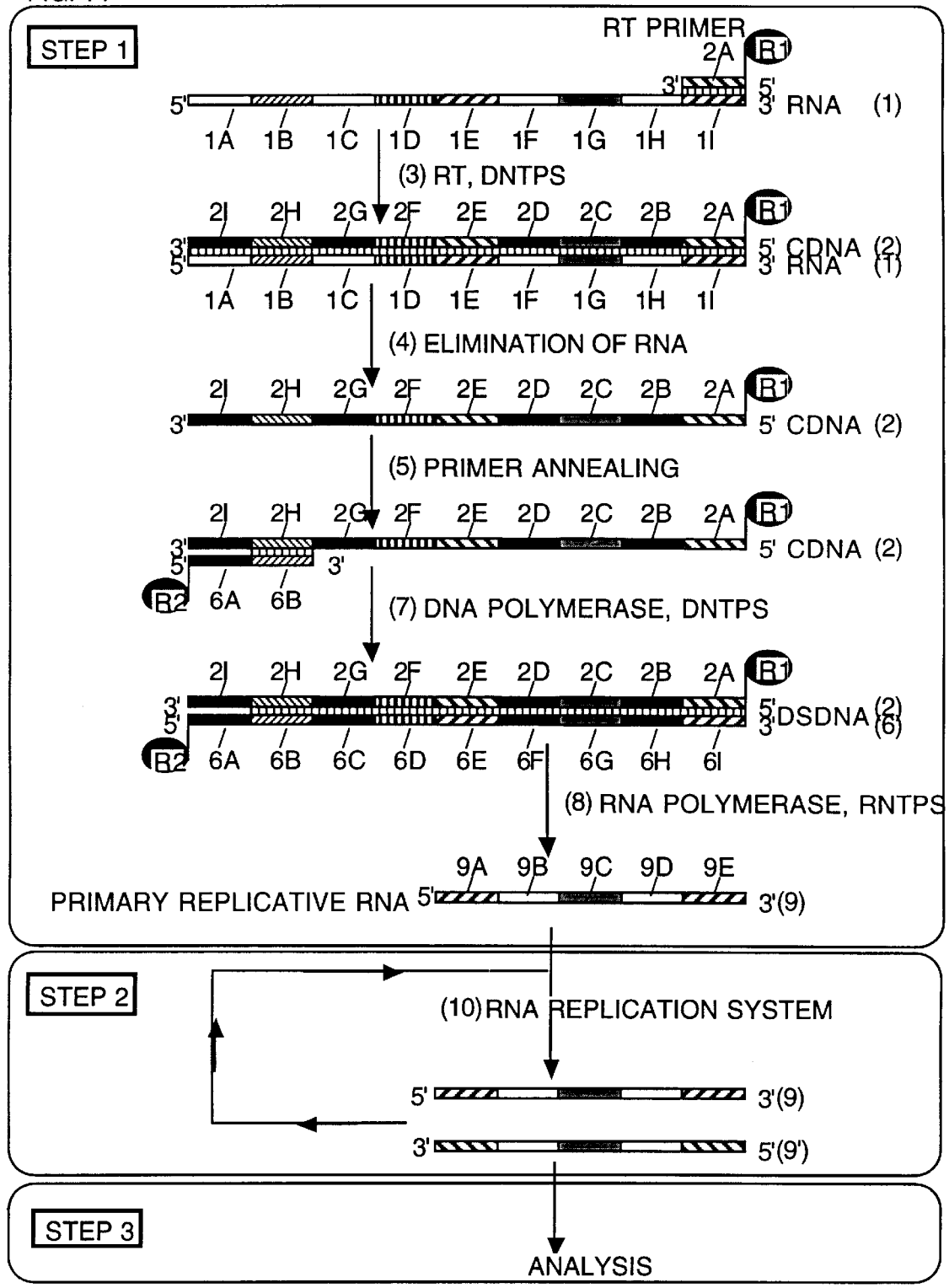

FIG. 14 shows a variant where the template nucleic acid already contains all functional sequences needed for the later RNA synthesis and amplification. The transcription promoter sequence is located at the 3'-end of the cDNA. The RNA synthesized at the end of step 1 shows the same polarity as the template nucleic acid.

Step 1: The template nucleic acid (1) contains a flanking sequence (1a) at its 5'-end, which is followed by a hybridization sequence (1b). Adjacent to this is a spacer sequence (1c). This is succeeded by a P(−) sequence of a transcription promoter (1d), and then, directly adjacent, by a 5'-RNA-ori (−) sequence (1e). (1f) refers to a spacer sequence, (1g) is the replicase binding domain and (1h) another sapcer sequence. In this variant (1i) serves a double function and contains both the 3'-RNA-ori(+) sequence and a hybridization sequence for the RT primer (2a); in this case the RNA-ori sequence must be located at the 3'-end but need only represent a part of the sequence used for hybridization. (1b), (1d), (1e), (1g) and (1i) are necessary for this variant, while (1a), (1c), (1f) and (1h) are facultative.

The RT primer (R1)(2a) is a DNA oligonucleotide. The necessary (2a) is a hybridization sequence that hybridizes with (1i) of the template nucleic acid (1), in addition it contains a 3'-ori(−) sequence at its 5'-end. The functional group (R1) is facultative.

In reaction (3) the RT activity in the sample synthesizes a cDNA consisting, as a maximum, of (2a) (2b) (2c) (2d) (2e) (2f) (2g) (2h) (2i). At least all sequences up to (2f) must be synthesized in the RT reaction for the PERT assay to be functionable.

As in FIG. 11 reaction (4) first effects the degradation of the template nucleic acid, the RNA (1). In this variant another reason for the degradation of the RNA is a possible interference due to the fact that the template nucleic acid (1) in its free form [that is, not paired with a primer (2a)] represents a substrate for the RNA replicase, owing to the presence of the replicase binding domain (1g) and the 3'-RNA-ori(+) sequence (1i). In reaction (5) follows the annealing of the second primer (R2) (6a) (6b), preferably a DNA oligonucleotide. It consists of (6b), the necessary hybridization sequence complementary to (2f), and contains a facultative flanking sequence (6a) at its 5'-end. The functional group (R2) is also facultative.

In reaction (7) a dsDNA consisting of strands (2) and (6) is synthesized by means of a DNA polymerase. As has been described in FIG. 8 this is the latest possible moment for re-establishing conditions needed to ensure the stability of the RNA in the reactions that follow. In the transcription reaction (8) follows the synthesis of the primary replicative RNA, which is the nucleic acid to be amplified. Its functional sequences (9a), (9b), (9c), (9d) and (9e) are identical to (1e), (1f), (1g), (1h) and (1i) of the template nucleic acid.

Step 2: The primary replicative RNA (9), which contains the same functional sequences as the primary replicative RNA in FIG. 12, is amplified in analogy to FIG. 12 and then analyzed in step 3.

Modifications

All functional sequences and functional groups that have been identified as facultative may be omitted, whether individually or in any of the various possible combinations.

Any of the variants described in FIG. 11, 12, 13, and 14 represents two possible extremes with regard to the method used for introducing the functional sequences necessary for the RNA synthesis and the RNA replication, with the exception of the replicase binding domain, into the dsDNA. Both the transcription promoter sequence and the RNA-ori sequences are either exclusively and completely encoded on the chosen oligonucleotides or they are completely encoded on the template nucleic acid. This separation is presented as an example and is not obligatory. Combinations are possible. It is also possible to design the template nucleic acid in such a way that it only contains parts of a certain necessary functional sequence and then to introduce the missing parts by means of one of the primers. All these possibilities also apply for the replicase binding domain.

Furthermore, the distinct separation of the hybridization sequences from the functional sequences necessary for the RNA synthesis and the RNA replication, which is illustrated in FIG. 11–14 is not compelling. A hybridization sequence may partially overlap with a RNA-ori sequence, with the replicase binding domain, with the transcription promoter sequence or also with two sequences adjacent to these functional sequences; it may also entirely contain any of these, or be identical to one of these, as has been described for the 3'-RNA-ori sequence in FIG. 12 and 14.

For example the variant described in FIG. 14 may be modified so that the primer for the second DNA strand contains the P(−) sequence of a transcription promoter as a hybridization sequence (6b), as well as at last three more nucleotides complementary to the cDNA. The primer then hybridizes to (2f) of the cDNA, the result being a partially dsDNA with a functional transcription promoter (6b)//(2f) for the RNA polymerase. Therefore the replicative RNA (9) may be synthesized (8) directly from this partially double-stranded DNA (2)//(6). The synthesis of the double-stranded DNA with DNA polymerase (7) can thus be omitted. The sequences (1a) . . . (1c) of the template nucleic acid also are now facultative and can be omitted.

As mentioned above, it may be preferable in certain constellations to use a template nucleic acid that contains a template DNA besides the template RNA, since this results in a considerably simpler synthesis of the primary replicative RNA. For example if the flanking sequence (1a) is left out in the template nucleic acid (1) shown in FIG. 12, if (1b) (1c) (1d) (1e) (1f) (1g) are presented in DNA, and of the other functional sequences at least (1h), which in this case is necessary, is presented in RNA, the RT reaction (3) produces in (1g)//(2d) a functional transcription promoter; this may then be used, by adding a corresponding DNA-dependent RNA polymerase as well as the necessary rNTPs, for the synthesis of a primary replicative RNA (9) consisting of (9a) (9b) (9c) (9d) (9e). Similarly, if the (P−) sequence of the transcription promoter (1d) of the template nucleic acid (1) shown in FIG. 14 and at least the first three nucleotides of (1e) directly downstream of this are presented in DNA, the RT reaction also produces a functional transcription promoter that allows the direct synthesis of the primary replicative RNA (9), which is synthesized complementary to the functional sequences (2e) (2d)2c) (2b) (2a) of the cDNA (2). The cDNA sequences (2) presented as the RT primer may be different in size, it is only important that the template-primer combination contains all functional sequences of a replicative RNA in the correct sequence and that a sufficiently long piece of template RNA is between the template DNA and the hybridization sequence for the RT primer.

The variants described in the following (FIG. 15–17) only use the cDNA synthesized in the RT reaction (3) for the selection of a reporter probe; this is either amplified itself in step 2 (FIG. 15), or it is at first used to synthesize a primary replicative RNA (FIG. 16, 17), which is then amplified in step 2.

Figure 15:
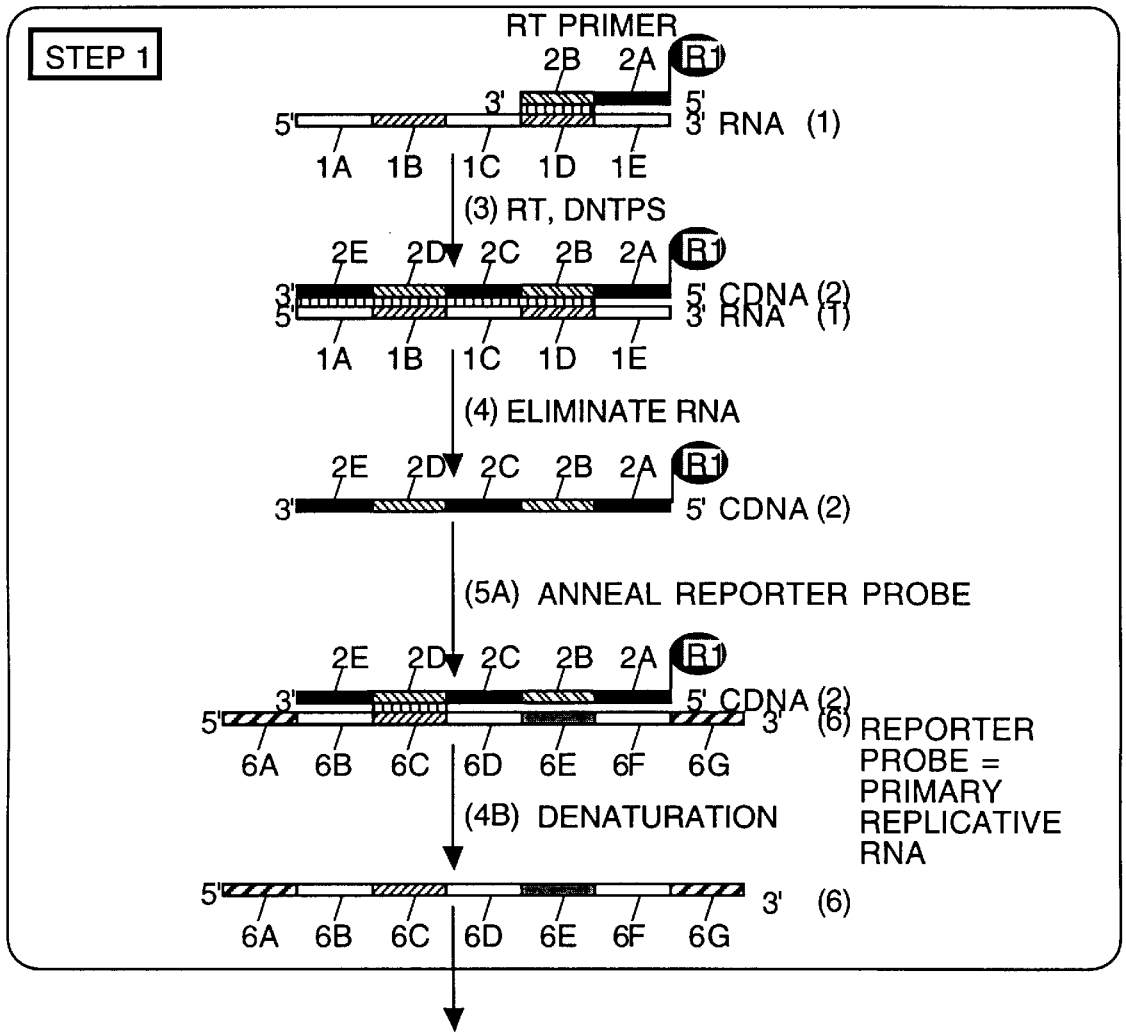
FIG. 15 shows the structure of the PERT assay in an illustrative variant, in which the nucleic acid to be amplified is a reporter probe consisting of a replicative RNA.

FIG. 15 shows a variant where the reporter probe used for the hybridization to the synthesized cDNA is a replicative RNA. After the unbound replicative RNA has been washed away, the specifically bound RNA is separated from the cDNA and then amplified.

Step 1: All necessary and facultative functional sequences of the template nucleic acid (1) and the RT primer (R1) (2a) (2b) as well as any options and obligations for the functional group (R1) are identical to those in FIG. 3. Besides this it is essential that only the hybridization sequence (2d) of the cDNA reacts with the hybridization sequence of the replicative RNA used as reporter probe. No other sequence of the template nucleic acid (1), or of the RT primer (R1) (2a) (2b), or of the cDNA (2) must be capable of any specific interaction with the replicative RNA used as a reporter probe.

The mixture of nucleic acids resulting from the RT reaction (3) is modified in reaction (4) is such a way as to ensure that none of its components, especially neither the template nucleic acid (1) nor the template-primer combination (1)//(R1) (2a) (2b), may participate as a specific competitor in the following hybridization reaction (5a) of the reporter probe (6) to the cDNA, as this might result in a reduced sensitivity of the assay or even false-negative results. This is why the template nucleic acid (1) is eliminated in reaction (4) by means of one of the methods mentioned above.

If degrading conditions have been used for the elimination of the template nucleic acid (1) it is now necessary to re-establish, in reaction (8), conditions that ensure the stability of the RNA in the reactions that follow. Then, in reaction (5a), a complete replicative RNA is hybridized to the cDNA (2) as a reporter probe, which consists of sequences (6a) (6b) (6c) (6d) (6e) (6f) (6g). Of these (6a) is a 5'-RNA-ori(−) sequence; (6b), (6d) and (6f) are spacer sequences, (6c) is a hybridization sequence for the hybridization of (2d) to the cDNA, (6e) is the replicase binding domain, and (6g) is a 3'-RNA-ori(+) sequence located at the 3'-end. (6a), (6c), (6e) and (6g) are necessary for the assay, the spacer sequences are facultative.

Not later than after the annealing of this reporter probe (6) to the cDNA has been completed, the cDNA is bound to a carrier by means of the functional group (R1), and unbound reporter probe is completely eliminated from the reaction mixture under non-denaturing conditions. For a rigorous washing a strong bonding between the carrier-bound cDNA (2) and the reporter probe (6) is essential. Therefore the hybridization region of these two nucleic acids, (2d) resp. (6c), must be of sufficient length and suitable consistency, and the annealing of the reporter probe (6) must be carried out in optimal conditions of reaction. Care must also be taken to ensure that the cDNA (2) remains bound to the carrier.

After the unbound reporter probe (6) has been washed away completely, the specifically bound replicative RNA (6) is separated fom the cDNA (2) by means of denaturation (4b), then amplified in step 2 in an adequate RNA replication system, and finally analyzed in step 3 by means of suitable methods.

Modifications

Figure 16:
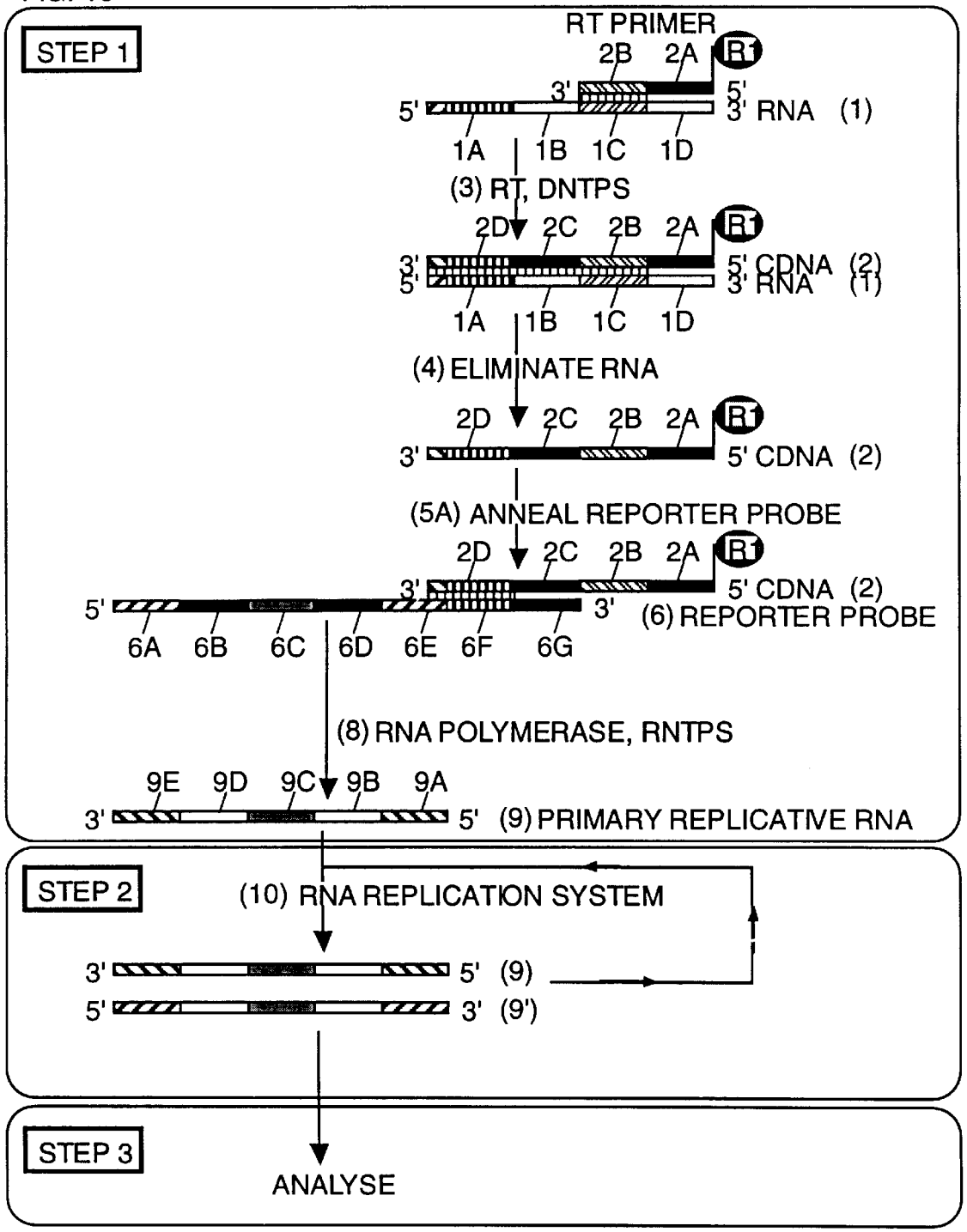
FIG. 16 shows the structure of the PERT assay in an illustrative variant, in which the nucleic acid to be amplified is a primary replicative RNA derived from a DNA reporter probe, which primary replicative RNA is amplified by means of a suitable RNA replication system.

The hybridization sequence (6c) of the reporter probe may also overlap with the replicase binding domain, with one of the RNA-ori-sequences or two adjacent necessary functional sequences, it may be identical to one of these sequences or contain one of these in its entirety, however preferably not a RNA-ori sequence. FIG. 16 illustrates a variant where the reporter probe used for the detection of the cDNA synthesized in step 1 is used for the synthesis of a replicative RNA:

Step 1: The template nucleic acid (1) contains a hybridization sequence (1a) at the 5'-end. This also contains the P(−) sequence of a transcription promoter and at least the first three nucleotides of a 3'-RNA-ori(+) sequence. Adjacent to this is the spacer sequence (1b). The hybridization sequence for the RT primer (1c) and the flanking sequence (1d) follow. (1a) and (1c) are necessary for this variant, while (1b) and (1d) are dispensable. The RT primer (R1) (2a) (2b) is identical to that in FIG. 3, the difference being that the functional group (R1) is now facultative. Otherwise it is essential that the hybridization sequence (2d) of the cDNA is the only one that reacts with the hybridization sequence, and only with this, of the reporter probe (6). No other sequence of the template nucleic acid (1), of the RT primer (R1) (2a) (2b) or of the cDNA (2) must be capable of interacting directly with the replicative RNA used as reporter probe. As the reporter probe (6) by itself is not a substrate for the RNA polymerase, the elimination of the template RNA is unnecessary in this variant. The reporter probe (6) is therefore at first hybridized to the cDNA (2) in reaction (5a). This is a ssDNA and contains the following functional sequences: (6a) is a 5'-RNA-ori(−) sequence; (6b) and (6d) are spacer sequences; (6c) is a replicase binding domain; (6e) is a 3'-RNA-ori(+) sequence of which at least 3 nucleotides are part of the hybridization sequence at the 3'-end; (6f) is the P(−) sequence of a transcription promoter and at the same time part of the hybridization sequence; and (6g) is a flanking sequence. (6a), (6c), (6e) and (6f) are necessary for the assay; (6g), (6b) and (6d) are facultative. In reaction (5a) the hybridization of the reporter probe (6) to the cDNA (2) produces an active transcription promoter (2d)//(part of 6e) (6f); this is then used in reaction (8), by means of a RNA polymerase and by using rNTPs, for the synthesis of the primary replicative RNA (9).

In step 2 the primary replicative RNA is amplified in the respective RNA replication system and then analyzed in step 3 with suitable methods.

Modifications

It is possible to modify the variants described above by placing the hybridization sequence of the reporter probe downstream of the P(−) sequence of the transcription promoter. In this case, the hybridization sequence (1a) of the template nucleic acid will contain neither any RNA-ori(+) sequence parts nor a P(−) sequence of a transcription promoter. An active transcription promoter is in this case produced by means of the annealing of an additional ssDNA oligonucleotide (6f') which contains the complementary sequences to the P(−) sequence of the transcription promoter (6f) and at least the first 3 nucleotides of the RNA-ori(+) sequence. A possible additional modification is for the template nucleic acid (1) to contain a flanking sequence at its 5'-end. In all these cases, however, the cDNA (2) must be bound to a carrier and any excess reporter probe must be washed away, at the latest after the reporter probe (6) has been annealed to the cDNA (2); thereafter conditions that ensure the stability of the RNA must be established.

Figure 17:
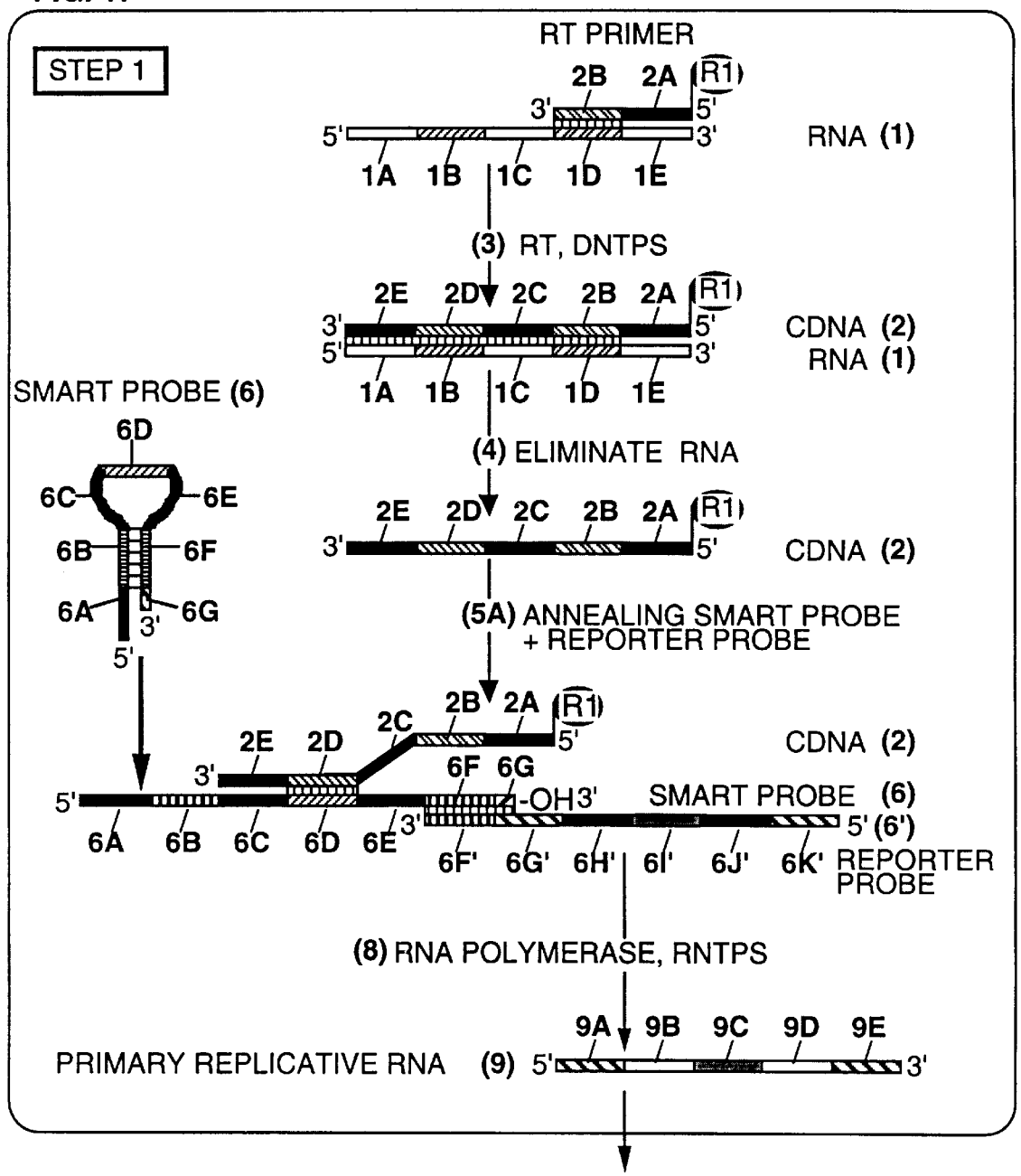
FIG. 17 shows the structure of the PERT assay in a variant, in which the nucleic acid to be amplified is a primary replicative RNA derived from the sequence of a reporter probe, which reporter probe is connected to the cDNA by means of a "smart probe".

FIG. 17 shows a variant of the PERT assay in which the detection of a cDNA produced by RT activity is achieved by means of the synthesis of a replicative RNA, which is induced by a "smart probe", as described in PS-WO 90/03445.

Step 1: The necessary and the facultative functional sequences of the template nucleic acid (1) and the RT primer (R1) (2a) (2b) as well as the options and standards for the functional group (R1) are identical to those in FIG. 3. In addition, it is essential that the hybridization sequence (2d) of the cDNA reacts only with the sequence of the "smart probe" chosen for the specific hybridization, but not with other sequences of the "smart probe" or with the ssDNA reporter probe that encodes the replicative RNA. No other sequence of the template nucleic acid (1), of the RT primer (R1) (2a) (2b) or of the cDNA (2) must be capable of any specific interaction with one of the two nucleic acids used for the synthesis of replicative RNA.

For the same reasons and in the same manner as described in FIG. 15 the template nucleic acid (1) is eliminated (4). The following reactions up to and including the synthesis of the primary replicative RNA follow the procedure described in PS-WO 90/03445: by means of detecting sequence (2d), which is only contained in the cDNA (2). First, a "smart probe" (6) is hybridized to sequence (2d) of the cDNA (2) and to a reporter probe (6') in reaction (5a). The "smart probe", a ssDNA, consists of the following parts: it contains a flanking sequence (6a) at its 5'-end, this is followed by the P(+) sequence of a transcription promoter (6b). This is succeeded by a spacer sequence (6c), sequence (6d) which is complementary to (2d) of the cDNA, and a second spacer sequence (6e). The P(−) sequence (6f) of the same transcription promoter follows, and another sequence that consists of at least three nucleotides (6g) follows at the 3'-end. The two spacer sequences (6b) and (6e) are not complementary to each other and separate the hybridization sequence (6d), which is complementary to the hybridization sequence (2d) of the cDNA, from the promoter sequences (6b) and (6f). The reporter probe (6'), a ssDNA, contains the information for a replicative RNA in (6g') (6h') (6i') (6j') (6k'); of these (6k') is the 5'-RNA-ori(−) sequence, (6j') a facultative spacer sequence, (6i') the replicase binding domain, (6h') another facultative spacer sequence and (6g') the 3'-RNA-ori(+) sequence, (6f') represents the P(+) sequence of a transcription promoter. In the absence of the target sequence (2d) of the cDNA the "smart probe" forms, by means of intramolecular hybridization of the two complementary transcription promoter sequences (6b) and (6f), a stem-loop-structure as a secondary structure, as shown on the left in FIG. 17. If however (6d) of the "smart probe" hybridizes to (2d) of the cDNA (2), (6f) and (6g) of the "smart probe" become available for the hybridization to sequences (6f') and parts of (6g') of the single-stranded reporter probe (6'). This hybridization produces a functional transcription promoter (6f) (6g)//(6f')(first 3 nucleotides of 6g'), and after the respective RNA polymerase and the necessary rNTPs have been added, the primary replicative RNA (9) is synthesized (8).

If, according to the invention, in reaction (4) degrading conditions have been established for the elimination of the template nucleic acid (1), it is essential to then re-establish, at the latest just before adding the RNA polymerase for the synthesis of the primary replicative RNA, conditions that ensure the stability of the RNA in the later reactions (cp. FIG. 8).

The primary replicative RNA (9) synthesized in reaction (8) by means of the RNA polymerase is amplified in step 2 in the respective RNA replication system and then analyzed in step 3 with suitable measures.

In all variants using a reporter probe, any functional sequences of the template nucleic acid (1), of the RT primer (R1) (2a) (2b) and of the reporter probe (6) that have been identified as facultative may be omitted, whether individually or in any of the various possible combinations.

PROCEDURE OF THE PERT ASSAY WHEN USING AN AMPLIFICATION PROCEDURE BASED ON REPLICATIVE DNA

In these PERT variants the detection of RT activity in the sample is achieved by amplifying DNAs that have been derived from the cDNA and are at least partially double-stranded, or by amplifying parts of the cDNA-template duplex, by means of an in vitro DNA replication system, and by then detecting these. An example for such a replication system is that of the bacteriophage f29, which contains the proteins p2 (a DNA replicase) and p3 (the so-called terminal protein), dNTPs and a suitable buffer system. The DNA that is to be replicated contains a DNA-ori at both ends, which is a defined sequence measuring at least 12 base pairs that is at least partially double-stranded. In the presence of dATP the terminal protein p2 covalently binds to the DNA-ori, thus causing the DNA replicase to initiate the replication in a protein-primed reaction, while the unreplicated strand is displaced.

Other DNA replication systems based on analogous principles may also be used for the amplification. Possible examples, which are by no means complete, are the bacteriophages M29, Nf or Cp1 as well as the eucaryotic adenoviruses.

Figure 18:
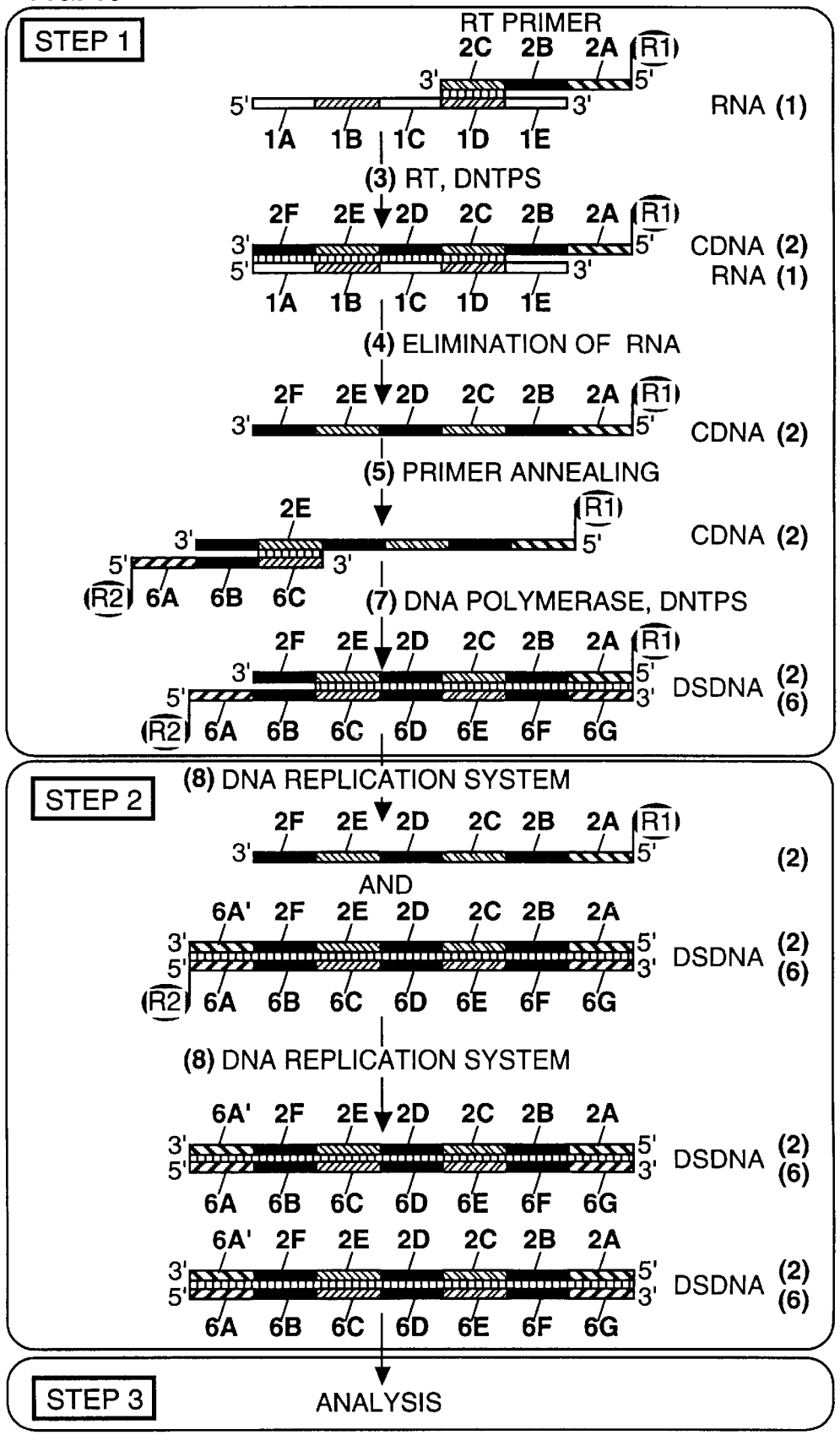
FIGS. 18,19 show the structure of the PERT assay in 2 illustrative variants, in which the nucleic acid to be amplified is a primary replicative DNA at least in part derived from a sequence of the cDNA, which primary replicative DNA is amplified by means of a suitable DNA replication system.
Figure 19:
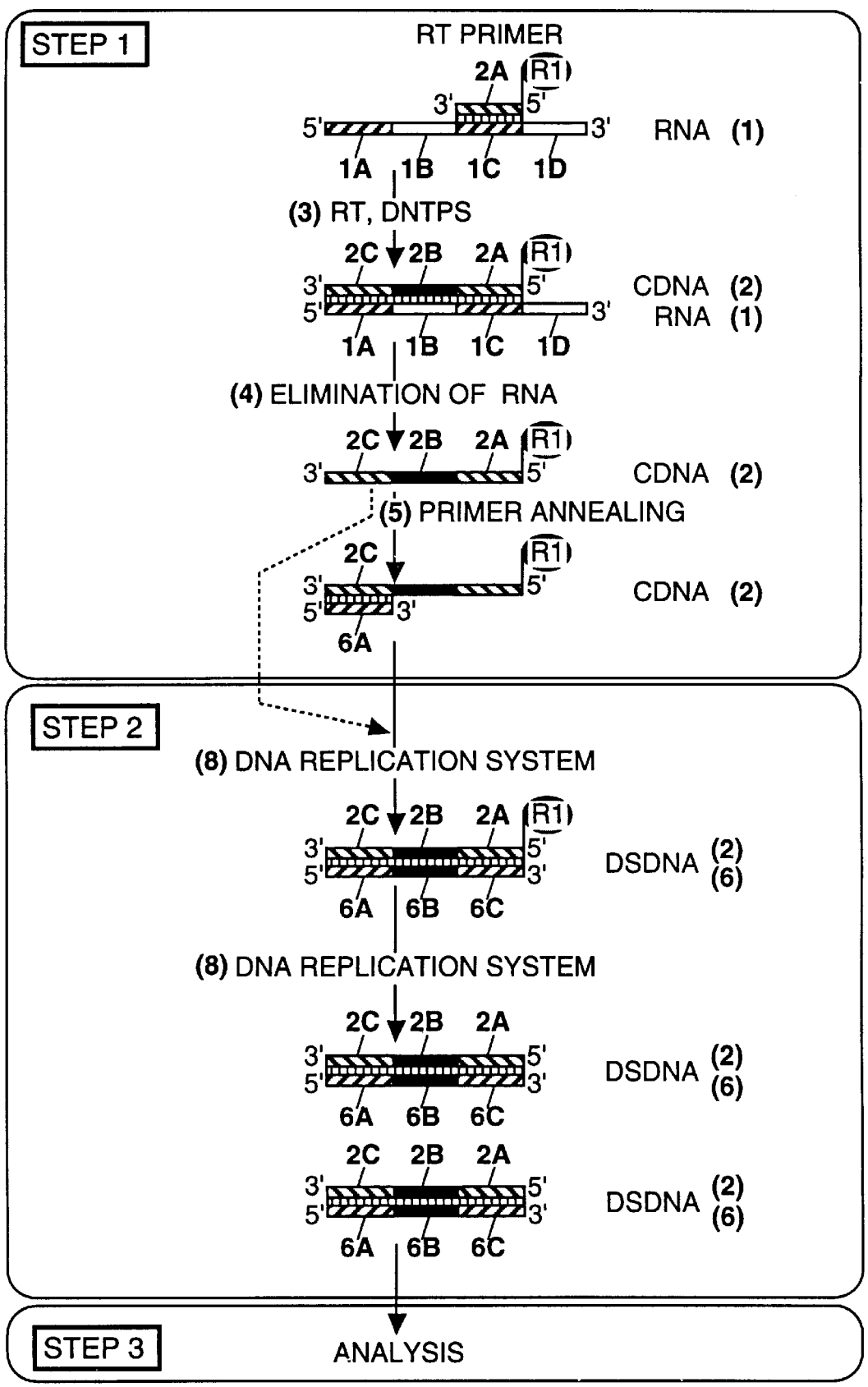
Figure 20:
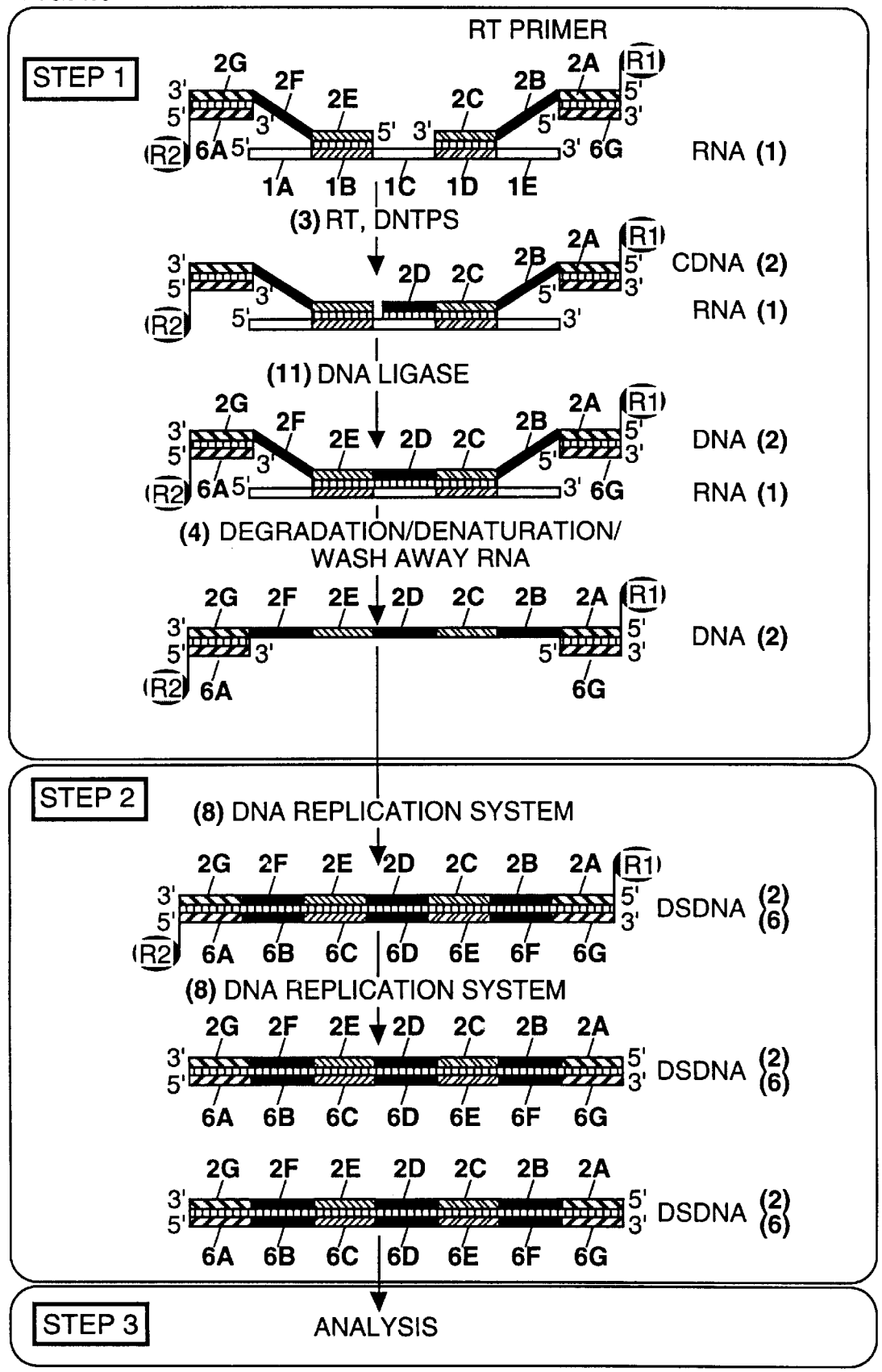
FIG. 20 shows the structure of the PERT assay in an illustrative variant, in which the nucleic acid to be amplified is a primary replicative DNA derived from the sequence of the cDNA and in which, instead of single-stranded oligonucleotides, adaptors are used as RT primers or resp. for the introduction of ori-sequences.
Figure 21:
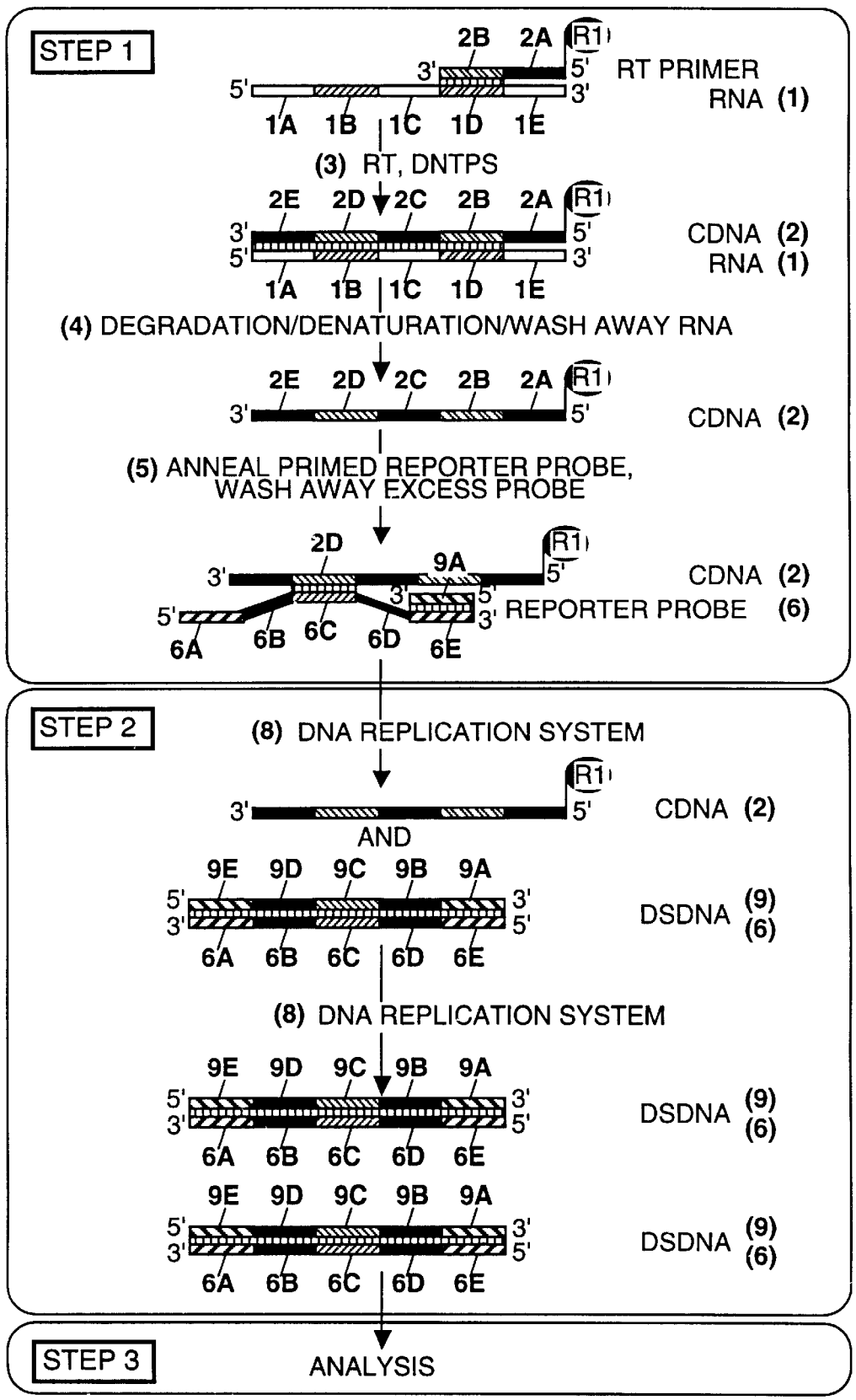
FIG. 21 shows the structure of the PERT assay in an illustrative variant, in which the nucleic acid to be amplified is a primary replicative DNA, which is also a reporter probe amplified by means of a suitable DNA replication system.
Figure 22:
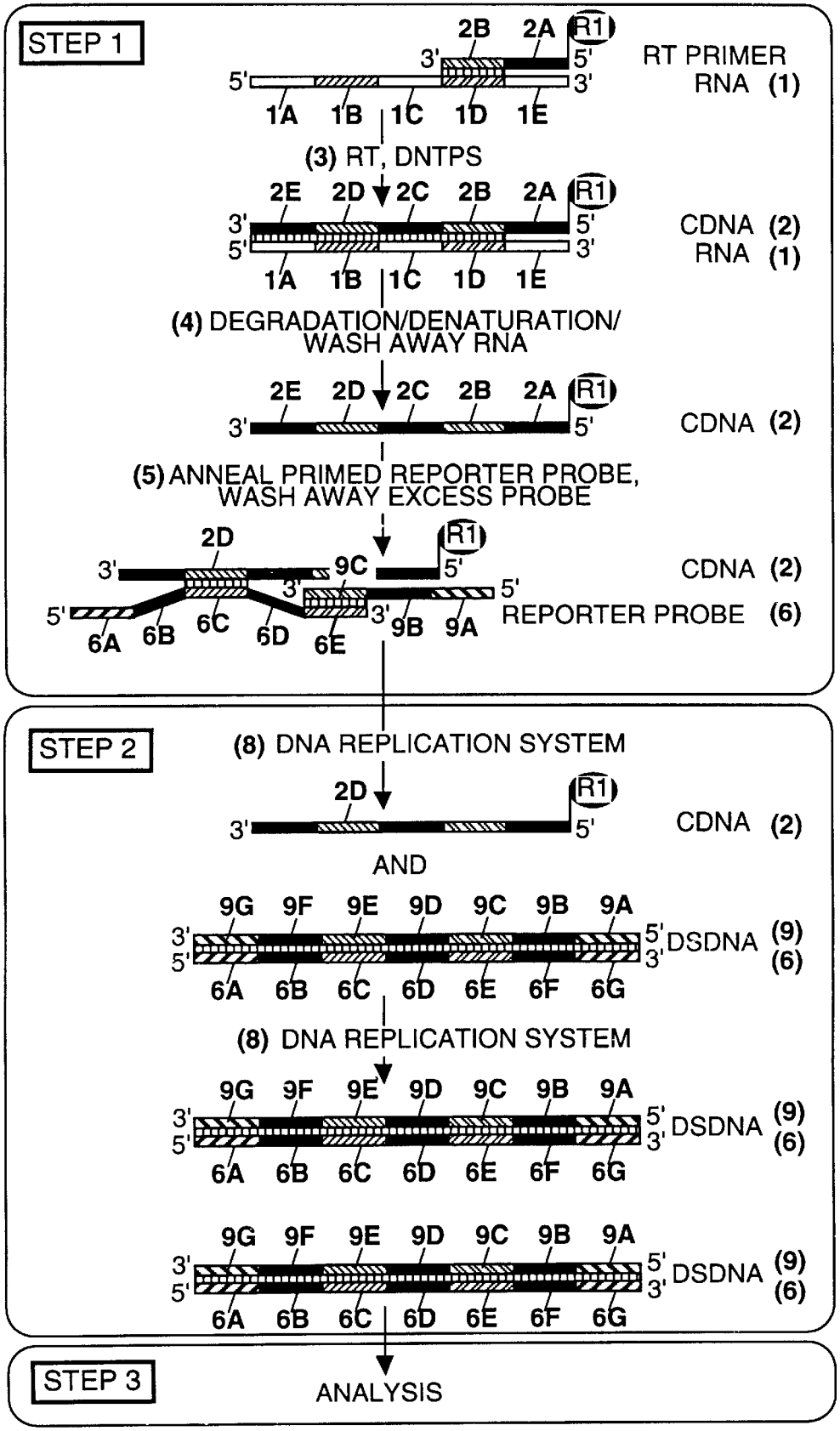
FIG. 22 shows the structure of the PERT assay in an illustrative variant, in which the nucleic acid to be amplified is a primary replicative DNA derived from a reporter probe, which primary replicative DNA is amplified by means of a suitable DNA replication system.

Based on a primed template nucleic acid a cDNA is synthesized by means of the RT activity in the sample in these PERT variants. If nothing else is mentioned a pure RNA is preferred as template nucleic acid. Starting from the cDNA a DNA, which is at least partially double-stranded is built, which has at least one DNA-ori at one end and at least one DNA-ori sequence for a defined DNA replication system at the other end. After the primary replicative DNA has been added to the corresponding replication system, it is amplified by means of repeated replication in step 2. In step 3 the dsDNA is analyzed. FIGS. 18–20 show variants functioning according to this principle. As in the other amplification procedures it is again possible to use the cDNA synthesized in the RT reaction (3) exclusively for inducing the amplification of a reporter DNA. FIG. 21 and 22 show this possibility.

FIG. 18 shows a first possible reaction process where the necessary functional sequences for the later initiation of the DNA replication are introduced into the dsDNA exclusively by means of the primers.

Step 1: The template nucleic acid (1) consists of the following functional sequences: a flanking sequence (1a) at the 5'-end, a hybridization sequence (1b), a spacer sequence (1c), a second hybridization sequence (1d) for the annealing of the RT primer, and a flanking sequence (1e) at the 3'-end. (1a) and (1e) are facultative, the other sequences are necessary.

The RT primer (R1) (2a) (2b) (2c) is a ssDNA, preferably an oligonucleotide. It contains a DNA-ori(−) sequence (2a), followed by a spacer sequence (2b) and a hybridization sequence (2c) at the 3'-end that hybridizes to (1d) of the template nucleic acid (1). (2a) and (2c) are necessary, (2b) and (2d) are facultative. In reaction 3, the RT activity in the pretreated sample synthesizes a cDNA (2) consisting of (R1) (2a) (2b) (2c) (2d) (2e) (2f). At least the functional sequences up to (2e) must be synthesized in the RT reaction for a functionable PERT assay.

The mixture of nucleic acids produced in reaction (3), which consists of unreacted template-primer combinations (1)//(R1) (2a) (2b) (2c), free primer molecules (R1) (2a) (2b) (2c), unprimed template nucleic acid molecules (1), and cDNA-template duplex molecules (1)//(2), is modified in reaction (4) so as to make sure that none of these components will interfere in an undesired manner with the optimal course of the later reactions. Above all it is essential to prevent the template nucleic acid (1), which is present in large quantities, and/or the template-primer combinations (1)//(R1) (2a) (2b) (2c) from competing with the hybridization (5) of the second oligonucleotide primer (R2) (6a) (6b) (6c) to the cDNA (2). This results in a lower sensitivity of the assay or even in false negative results.

It is therefore necessary to eliminate, in reaction (4), the existing template nucleic acid, the RNA (1), as a relevant participant in the annealing reaction (5). If maximal sensitivity need not be achieved it is possible to forego the elimination of the template nucleic acid from the reaction mixture.

The annealing of a second ssDNA primer, preferably an oligonucleotide, follows in reaction (5). This primer contains two necessary sequences, a DNA-ori(−) sequence (6a) at the 5'-end, and a hybridization sequence (6c) for the hybridization to (2e) of the cDNA (2) at the 3'-end. Facultative sequences are the spacer sequence (6b) and the functional group (R2). Due to the effect of a DNA-dependent DNA polymerase and by using dNTPs a partially double-stranded DNA, consisting of strands (2) and (6), is synthesized in reaction (7).

Step 2: The partially double-stranded DNA (2)//(6), which carries a DNA-ori sequence at both ends, is the primary replicative DNA; it is added to the corresponding amplification system. Replication due to the DNA replicase (8) of the replication system produces, based on the active double-stranded DNA-ori (2a)//(6g), the entirely double-stranded DNA product (R2)(6)//(2); as a result of the strand displacing activity of the DNA replicase the cDNA (2) which carries (R1) is thereby set free. The double-stranded DNA product (R2) (6)//(2) with the two active DNA-ori, (2a)//(6g) and (6a)//(6a'), is then amplified by means of multiple repeated replication (8).

Step 3: The product of the amplification reaction is a dsDNA (6)//(2), which is analyzed with suitable methods.

Modifications

Any functional sequences and functional groups of the template nucleic acid (1) and the oligonucleotide primers (R1) (2a) (2b) (2c) and (R2) (6a) (6b) (6c) that have been identified as facultative may be omitted individually or in any of the possible combinations.

In deviation from the principle of a different base sequence for each functional sequence it is possible for the flanking sequences (1a) and (1e) as well as the spacer sequence (1c) of the template nucleic acid (1), and the spacer sequences (2b) and (6b) of the primers to be identical, whether single or in combination, the condition being that this does not interfere with the test development in any way. Furthermore the hybridization sequences (2c) and (6c) of the oligonucleotide primers (and therefore also the hybridization sequence (1b) and (1d) of the template nucleic acid) may present an identical DNA sequence; however this must be different from the flanking and the spacer sequences.

FIG. 19 shows a reaction development where the DNA-ori sequences necessary for the later DNA replication are already completely coded for in the template nucleic acid.

Step 1: The template nucleic acid (1) consists of the following functional sequences: a hybridization sequence (1a) at the 5'-end, a spacer sequence (1b), a hybridization sequence (1c) for the annealing of the RT primer, and a flanking sequence (1d) at the 3'-end. The two hybridization sequences (1a) and (1c) encode in addition the two DNA-ori sequences for the DNA replication as follows: (1a) contains a DNA-ori(−) sequence at its 5'-end, the hybridization sequence (1d) contains a DNA-ori(+) sequence at the 3'-end. The flanking sequence (1d) is facultative, all other sequences are necessary.

The RT primer (R1) (2a) is a DNA oligonucleotide. This contains a necessary hybridization sequence (2a), which simultaneously is a DNA-ori(−) sequence and mediates the hybridization of (1d) to the template nucleic acid (1). (R1) is facultative.

In reaction (3), the RT activity present in the pretreated sample synthesizes a cDNA (2) consisting of (R1) (2a) (2b) (2c). The PERT assay can only function if at least all functional sequences up to (2c) are synthesized in reaction (3).

For the same reasons as in FIG. 18 it is necessary to eliminate, in reaction (4), the template nucleic acid, the RNA (1), as a relevant participant in the annealing reaction (5), as has been described above. If maximal sensitivity is not needed it may be possible to dispense with the elimination of the template nucleic acid from the reaction mixture. The annealing of a second DNA oligonucleotide primer follows in reaction (5). This primer contains the necessary hybridization sequence (6a) for the hybridization to (2c) of the cDNA (2); (6a) is also a DNA-ori(−) sequence. (R2) is facultative. The annealing of the oligonucleotide (6a) produces a primary replicative DNA with an active DNA-ori (2c)//(6a). This DNA represents the nucleic acid to be amplified.

Step 2: The partially double-stranded DNA (R1) (2)//(6a), which carries a DNA-ori sequence at both ends, is added to the corresponding amplification system. The effect of the DNA replicase (8) of the replication system at first produces the consistently double-stranded DNA (R1) (2)//(6). This double-stranded DNA (2)//(6) carrying (R1) is subsequently amplified by means of multiple repeated replication (8).

Step 3: The result is a dsDNA (6)//(2), which is then analyzed with suitable methods.

Modifications

Sequence (1d) of the templatenucleic acid (1), which has been identified as facultative, may be omitted.

Contrary to the principle of a different base sequence for each functional sequence it is possible for the flanking sequence (1d) and the spacer sequence (1c) of the template nucleic acid (1) to be identical, as long as this does not interfere in any way with the test development.

The two primers (R1) (2a) and (6a), which in this variant contain the minimal DNA-ori(−) sequence needed, can be modified so that they are shorter than this at the 3'-end, or they may also stretch beyond the 3'-end of this minimal DNA-ori(−) sequence.

The cDNA (2) is also a replicative DNA in this version, as a consequence of the hybridization of the two DNA-ori sequences (2c) and (2a) to each other in the form of a "stem loop" structure, the result being a functional DNA-ori (2a)//(2c). Therefore the addition of the oligonucleotide (6a) can also be omitted, although this reduces the efficiency of the initial DNA replication.

FIG. 20 shows a variant which, in place of single-stranded oligonucleotides, uses adaptors as primers and for the introduction of the DNA-ori sequences.

Step 1: The template nucleic acid (1) consists of the following functional sequences: a flanking sequence (1a) at the 5'-end, a hybridization sequence (1b), a spacer sequence (1c), a second hybridization sequence (1d) for the annealing of the RT primer (R1) (2a) (2b) (2c), and a flanking sequence (1e) at the 3'-end. (1a) and (1e) are facultative, all other functional sequences are necessary.

The RT primer (R1) (2a) (2b) (2c)//(6g) is an adaptor consisting of several parts, it consists of a DNA oligonucleotide (R1) (2a) (2b) (2c) that forms a partially double-stranded DNA with a second oligonucleotide (6g), which is hybridized to sequence (2a). This adaptor contains the hybridization sequence (2c) at its 3'-end, which is hybridized to sequence (1d) of the template nucleic acid (1). Adjacent to this is a spacer sequence (2b), followed by a DNA-ori(−) sequence (2a). The oligonucleotide (6g) contains the DNA-ori(+) sequence complementary to (2a). The functional sequences (2a) and (2c) are necessary, the others as well as (Ri) are facultative.

The second adaptor (2e) (2f) (2g)//(R2) (6a), which is hybridized to the hybridization sequence (1b) of the template nucleic acid (1), consists of the DNA oligonucleotides (2e) (2f) (2g) and (R2) (6a); the oligonucleotide (2e) (2f) (2g) is phosphorylated at its 5'-end. (2e) contains the hybridization sequence used for the hybridization to (1b); (2f) is a spacer sequence and (2g) is a DNA-ori(+) sequence, which is also a hybridization sequence. The DNA oligonucleotide (6a), which contains the DNA-ori(−) sequence complementary to (2g), is hybridized to (2g). The spacer sequence (2f) is facultative, all other sequences are necessary for the test. The oligonucleotide (6a) may also carry a functional group (R2) as a facultative element.

In reaction 3, the RT activitiy present in the pretreated sample synthesizes a cDNA (2) consisting of (R1) (2a) (2b) (2c) (2d)//(6g); in combination with the template nucleic acid (1) this presents in the form of a partial cDNA-template duplex (2)//(1) and is only separated by one nick from the 5'-end of the second adaptor (2e) (2f) (2g)//(R2) (6a), which is hybridized to the hybridization sequence (1b) of the template nucleic acid (1). In reaction (11) the two DNA strands (2a) (2b) (2c) (2d) of the cDNA and (2e) (2f) (2g) of the second adaptor, which are separated from each other by one nick, are connected to one consistent DNA molecule (2a) (2b) (2c) (2d) (2e) (2f) (2g) by means of a DNA ligase, which is also active on a DNA-RNA heteroduplex substrate, e.g. T4 DNA ligase.

In reaction 4, before the amplification reaction that follows, the template nucleic acid, the RNA (1), is elimi-nated. If maximal sensitivity is not necessary, the elimination of the RNA from the reaction mixture may be omitted.

The RNA needs to be elimated, since in step 2 the strand displacement activity of the DNA-dependent DNA polymerase present in the replication system generates single-stranded DNA molecules (2a) (2b) (2c) (2d) (2e) (2f) (2g), which, due to the intramolecular hybridization of the two complementary DNA-ori sequences (2a) and (2g), form a functional DNA-ori; this is used by the replication system for transforming the single-stranded molecule (2) into a dsDNA (2)//(6). Since large quantities of the template nucleic acid (1) are present in the reaction mixture, it can hybridize with the partially complementary ssDNA molecule (2) and affect the formation of a intramolecular functional DNA-ori, which is necessary for the efficient amplification.

Step 2: The DNA (6g)//(R1) (2a) (2b) (2c) (2d) (2e) (2f) (2g)//(R2) (6a), which contains a double-stranded DNA-ori sequence at both ends but is otherwise single-stranded, represents the primary replicative DNA and is added to the respective amplification system. Due to the effect of the DNA replicase (8) of the replication system the totally double-stranded DNA (6)//(2), which carries (R1) and (R2), is generated. This contains the two active DNA-ori (6a)//(2g) and (2a//(6g) at its ends, it is subsequently amplified by means of multiple repeated replication (8).

Step 3: The product of the amplification reaction is a dsDNA (6)//(2), which is analyzed with the help of suitable detection methods.

Modifications

All functional sequences and functional groups of the template nucleic acid (1) and of the adaptors (R1) (2a) (2b) (2c)//(6a) and (2e) (2f) (2g)//(R2) (6a) that have been identified as facultative may be omitted, whether individually or in any of the various possible combinations.

In deviation from the principle of a different base sequence in each functional sequence it is possible for both the flanking sequences (1a) and (1e) and the spacer sequence (1c) of the template nucleic acid, as well as the spacer sequences (2b) and (2f) of the adaptors, to be identical, whether individually or in combination, provided that they do not in any way interfere with the development of the test.

The length of the two shorter oligonucleotides (6a) and (6g) of the two adaptors, which is defined as that of the DNA-ori sequence in the illustrated variant, may also be shorter or longer than the minimal DNA-ori sequence at its 3'-end.

It is not compelling to distinguish between variants with single-stranded oligonucleotide primers and variants with adaptors. It is certainly possible to design logical combinations of the the variants shown in FIGS. 18 to 20. Similarly, the PERT assay does not absolutely depend upon the exclusive association of one single function per one functional sequence. A hybridization sequence may overlap with another functional sequence, contain such a sequence or be identical to it, as has been described for the hybridization sequences and for the DNA-ori(−) and the DNA-ori(+) sequences in FIG. 19.

As mentioned above, in certain constellations it is preferable to use a template nucleic acid (1) that contains a template DNA in addition to the template RNA, since this significantly simplifies the synthesis of a primary replicative DNA. E.g., if the DNA-ori(−) sequence (1a) for the template nucleic acid (1) shown in FIG. 19 is presented in DNA instead of RNA, the result of the RT reaction (3) is a primary replicative DNA with an active DNA-ori (2c)//(1a). This represents the nucleic acid to be amplified and can be amplified directly within the corresponding replication system.

The variants described in FIGS. 21 and 22 again prefer a pure RNA as template nucleic acid. They only use the cDNA synthesized by means of the RT activity for the specific hybridization of a partially complementary reporter probe, which is either amplified itself in step 2 (FIG. 21), or functions as a target DNA, which is subsequently analyzed (FIG. 22).

FIG. 21 describes a reaction in which a primary replicative DNA is used as reporter probe, in step 2 this DNA itself forms the substrate for the amplification reaction.

Step 1: Both the necessary and the facultative functional sequences of the template nucleic acid (1) and the RT primer (R1) (2a) (2b) and the possibilities and the requirements for (R1) are identical to those in FIG. 3. Apart from this it is required that the hybridization sequence (2d) of the cDNA reacts only and exclusively with that sequence of the reporter probe DNA that has been specifically designated for the hybridization.

The mixture of nucleic acids produced in the RT reaction (3) is modified in reaction (4) in a way that ensures that no nucleic acid can be present as a specific competitor in the hybridization reaction (5) of the reporter probe (6) with the cDNA (2), since this might decrease the sensitivity of the assay or even lead to false negative results. In reaction (4) the template nucleic acid (1) is thus eliminated by using one of the methods mentioned. At first, a primary replicative DNA is hybridized as the reporter probe (6)//(9a) in reaction (5a). This reporter probe (6)//(9a) contains the following functional sequences: (6a) is a DNA-ori(−) sequence; (6b) refers to the spacer sequence that separates (6a) from the hybridization sequence (6c), which is used for the specific hybridization to (2d) of the cDNA; (6d) is another spacer sequence; (6e), which is located at the 3'-end, is a DNA-ori (+) sequence. (9a) is a DNA oligonucleotide hybridized to (6e), it consists of a hybridization sequence that is also a DNA-ori(−) sequence. The two spacer sequences (6b) and (6d) are facultative, all other sequences are necessary for the functioning of the PERT assay.

After the annealing of the reporter probe (6)//(9a) to the cDNA (2) all unbound reporter probe is completely removed from the reaction mixture under non-denaturing conditions, as described in FIG. 3.

Step 2: The combination of the cDNA (2) with the hybridized reporter probe (R1) (2)//(6)//(9a) presents the substrate for the replication in step 2, in this case the reporter probe (6)//(9a) is the nucleic acid to be amplified. Due to the effect of the DNA replicase (8) of the replication system the totally double-stranded DNA (6)//(9) is generated, and due to the strand displacing activity of the DNA replicase the cDNA (R1) (2) is released. Subsequently the dsDNA (6)//(9) is amplified by means of multiple repeated replication.

Step 3: The main product yielded by the amplification is the dsDNA (6)//(9), which is analyzed with suitable methods.

Modifications

All facultative functional sequences and functional groups of the template nucleic acid (1), of the RT primer (R1) (2a) (2b), and of the reporter probe (6)//(9a) may be omitted, whether individually or in any of the various possible combinations.

The template nucleic acid (1) may contain several hybridization sequences (1b) for reporter probes and/or several hybridization sequences (1d) for RT primers.

The primer for the RT reaction may be either a DNA or a RNA or a combination containing parts of both.

The oligonucleotide (9a) that is hybridized to the reporter probe may vary in length. It must at least contain the first 6 nucleotides of the DNA-ori sequence, however, it may also be longer at its 3'-end and contain additional bases which are complementary to (6d). The length of the oligonucleotide (9a) must be chosen in a way that ensures a sufficiently stable binding to the DNA (6) even while the unbound reporter probe (6)//(9a) is being washed away.

It is also possible to hybridize only the DNA (6) as reporter probe to the cDNA, and to produce a primary replicative DNA only after washing away the unbound DNA (6), by annealing the oligonucleotide (9a) to the DNA (6) in a further annealing reaction.

In deviation from the principle of one single function per one functional sequence it is possible to incorporate, either partially or entirely, the DNA-ori sequence (6a) into the hybridization sequence that is used for the hybridization of the reporter probe (6)//(9a) to the cDNA (2). In this case the corresponding spacer sequence (6b) is dropped. However, the presence of at least one spacer sequence on the reporter probe will then become necessary.

In deviation from the principle of a different base sequence in each functional sequence it is possible for the flanking sequences and the spacer sequences of the template nucleic acid (1), of the primer (R1) (2a) (2b) and of the reporter probe (6)//(9a), to be identical, whether individually or in combination, provided that this does not in any way interfere with the development of the test.

FIG. 22 shows a variant that uses a DNA reporter probe for the hybridization to the cDNA, this reporter probe is used for the synthesis of a primary replicative DNA.

Step 1: Both the necessary and the facultative functional sequences of the template nucleic acid (1) and the RT primer (R1) (2a) (2b) and the possibilities and requirements for (R1) are identical to those in FIG. 3.

For the same reasons as described in FIG. 18 at first, in reaction (4), the template nucleic acid, the RNA (1), is eliminated using one of the methods mentioned. In reaction 5 a partially double-stranded DNA (6a) (6b) (6c) (6d) (6e)//(9c) (9b) (9a) is then hybridized as reporter probe to the cDNA (2). The reporter probe contains the following functional sequences: (6a) is a DNA-ori(−) sequence; (6b) is a spacer sequence; (6c) is the hybridization sequence for the specific hybridization to the cDNA; (6d) is another spacer sequence; and (6e) is the hybridization sequence for the hybridization of the DNA (6a) (6b) (6c) (6d) (6e) to the DNA (9c) (9b) (9a). (9c) is the hybridization sequence for the hybridization to (6e); (9b) is a spacer sequence and (9a) a DNA-ori(−) sequence. The spacer sequences (6b), (6d) and (9b) are facultative. All other functional sequences are necessary for the functioning of the PERT assay.

Not later than after the annealing of this reporter probe to the cDNA (2) the latter is bound to a carrier by means of the functional group (R1), and any unbound reporter probe is completely eliminated from the reaction mixture under non-denaturing conditions.

Step 2: The combination of cDNA with the hybridized reporter probe (R1) (2)//(6a) (6b) (6c) (6d) (6e)//(9c) (9b) (9a) represents the substrate for the DNA replicase in step 2. The effect of the DNA replicase (8) of the replication system at first yields a totally double-stranded replicative DNA (6)//(9), and due to the stramd displacing activity of the DNA replicase the cDNA (R1) (2) is released. Subsequently the dsDNA (6)//(9) is amplified by means of multiple repeated replication (8).

Step 3: The dsDNA product of the amplification is analyzed by suitable methods.

Modifications

All facultative elements of the template nucleic acid (1), of the RT primer (R1)(2a)(2b) and of the reporter probe (6a) (6b) (6c) (6d) (6e)//(9c) (9b) (9a) may be omitted, either individually or in any of the various possible combinations. The primer used for the RT reaction may be either a DNA or a RNA.

In deviation of the principle of one single function per one functional sequence it is possible to have the hybridization sequence (6c) for the hybridization of the reporter probe (6a) (6b) (6c) (6d) (6e)//(9c) (9b) (9a) to the cDNA (2) overlap, partially or entirely, with the DNA-ori(−) sequence (6a), or to make these identical. In this case the corresponding spacer sequence between the hybridization sequence (6c) and the DNA-ori(−) sequence is dropped.

In deviation of the principle of a different sequence in each functional sequence it is possible for the flanking and the spacer sequences of the template nucleic acid (1), of the primer (R1) (2a) (2b) and of the reporter probe (6a) (6b) (6c) (6d) (6e)//(9c) (9b) (9a) to be identical, individually or in any of the possible combinations, provided that this does not interfere in any way with the development of the test.

The primary replicative DNA can already be produced in step 1 by means of a DNA polymerase, rather than in step 2 by means of the DNA replicase.

STRUCTURE OF THE PERT WHEN USING THE "AMPLIFICATION METHOD FOR POLYNUCELOTIDE ASSAYS" (U.S. Pat. No. 4, 994,368) IN STEP 2

Figure 23:
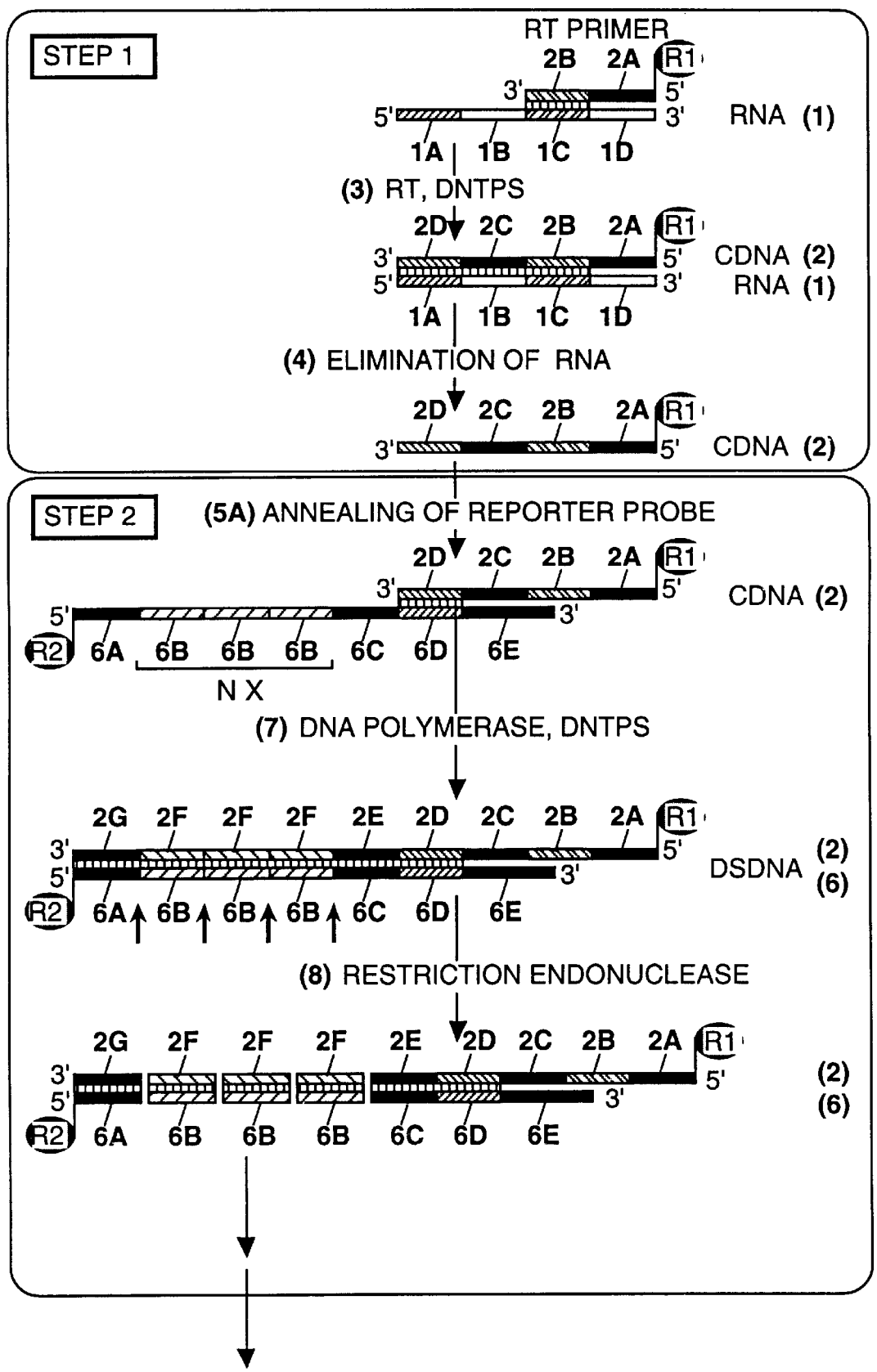
FIG. 23 shows the structure of the PERT assay, in which the nucleic acid to be amplified is a sequence of a reporter probe that is amplified by means of a cyclic procedure that comprises the synthesis of a dsDNA and its digestion by means of a restriction enzyme.

FIG. 23 shows the reaction sequence of the PERT assay when using the procedure described in U.S. Pat. No. 4,994, 348 in step 2.

Step 1: A template nucleic acid is presented that preferably is a pure RNA and contains the functional sequences (1a) (1b) (1dc) (1d). (1a) is an obligatory hybridization sequence which must not consist of DNA. Sequence (2d), which is derived from this, is used for binding the reporter probe in reaction (5a). (1c) is also a necessary hybridization sequence and serves for binding the RT primer (R1) (2a) (2b). (1b) is a spacer sequence and (1d) is a flanking sequence. These two are facultative.

The RT primer (R1) (2a) (2b) is a single-stranded nucleic acid, preferably a DNA- or an RNA-oligonucleotide. It consists of the facultative functional group (R1), the facultative flanking sequence (2a), and the hybridization sequence (2b), which is necessary for the hybridization to (1c) of the template nucleic acid.

If RT activity is present in the pretreated sample, a cDNA (2) is synthesized in reaction (3) by integrating the necessary dNTPs. For a functionable PERT assay all functional sequences in the cDNA up to (2d) must be present.

With the exception of the hybridization sequence (2d) of the cDNA, which is complementary to (1a), it is required, for all functional sequences of the template nucleic acid (1) and of the RT primer (R1) (2a) (2b) as well as any sequences derived from these, not to enter any specific interaction with the reporter probe. The hybridization sequence (2d) is the only one that hybridizes to it.

The mixture of nucleic acids resulting from reaction (3), which consists of unreacted template-primer combinations (1)//(R1) (2a) (2b), of free primer molecules (R1) (2a) (2b), unprimed template nucleic acid molecules (1) and cDNA-template duplex molecules (1)//(2), is modified in reaction (4) in such a way that it is guaranteed that none of these components, especially neither the template nucleic acid (1) nor the template-primer combinations (1)//(R1) (2a) (2b), can act as a specific competitor for the reportrer probe (6) in the following reactions and thus lead to false-negative results.

Therefore the existing template nucleic acid, the RNA (1), is eliminated as a relevant participant in the annealing reaction (5a), as described above. If maximum sensitivity is not essential, the elimination of the template nucleic acid from the reaction mixture may be dispensed with.

Step 2: The DNA reporter probe (6) used in step 2 and the various reaction steps for the amplification correspond to the procedure described in U.S. Pat. No. 4,994,368. To begin with, in reaction (5a) a single-stranded DNA reporter probe (6) is hybridized to the hybridization sequence (2d) of the cDNA (2). This DNA reporter probe (6) consists of the functional sequences (6a) (6b) (6c) (6d) (6e); of these (6b) occurs several times, with identical sequence orientation. (6d) is the obligatory hybridization sequence which hybridizes specifically to the hybridization sequence (2d) of the cDNA (2) synthesized in the RT reaction (3). All other functional sequences of the reporter probe (6) must not hybridize with the cDNA (2), nor may any of their sequences be identical to each other. The repetitive sequence (6b). is also necessary. In its double-stranded form (6b)//(2f), it represents the nucleic acid to be amplified as well as the amplification product. It contains a recognition sequence for a certain restriction endonuclease (marked by arrows) at each end that separates the repetitive sequence from a neighboring functional sequence. (6c) is a facultative spacer sequence, and (6a) and (6e) are facultative flanking sequences. The functional group (R2) is facultative.

After the hybridization (5a) of the reporter probe (6), in reaction (7), the 3'-end of the cDNA (2) synthesized in reaction (3), which functions as primer for this reaction, is used, with the help of a DNA-dependent DNA polymerase (e.g. Klenow fragment of E. coli DNA polymerase I) and by including dNTPs, to synthesize the DNA (2e) (2f) (2g) complementary to the functional sequences (6c) (6b) (6a). The dsDNA thus generated is then cleaved by the restriction endonuclease specific for the recognition sequence, the result in each case being several molecules of the double-stranded fragment (6b)//(2f). Subsequently a large amount of the double-stranded fragment (6b)//(2f) is produced by multiple repetition of the reaction cycle, which consists of hybridization (5a), DNA synthesis (7) and digestion by the restriction endonuclease (8).

Step 3: The double-stranded product (6b)//(2f) is analyzed with the help of appropriate methods.

Modifications

All functional sequences and functional groups of the template nucleic acid (1), of the RT primer (R1) (2a) (2b) and of the reporter probe (6) that have been identified as facultative may be omitted, whether individually or in any of the various possible combinations. However, using a reporter probe with flanking sequences allows using linear as well as circular molecules as reporter DNA.

In deviation from the principle of one single function per one functional sequence, the hybridization sequence (2d) derived from (1a) of the template nucleic acid (1) may not only be used for the hybridization of the reporter probe but may also contain the sequence that is complementary to (6b)

and thus be included in the specific amplification product. The spacer sequence (6c) of the reporter probe, and also the sequence (2e) derived from this, are then dropped. While these two functions may be entirely identical, they may also overlap in part, or the shorter of the two sequences may be integrated entirely in the longer one.

In deviation from the norm the flanking sequences as well as the spacer sequences of the template nucleic acid (1) and of the reporter probe (6) may be identical in pairs or in any of the possible combinations.

For this PERT variant it is essential that the hybridization sequence (2d) of the cDNA used for the hybridization and the priming is located at the 3'-end of the latter. In FIG. 23 this is made possible, since the hybridization sequence (1a) of the template nucleic acid (1) that is complementary to (2d) is located at the 5'-end. However, it is also possible to extend the template nucleic acid (1) by one sequence at its 5'-end and to place the hybridization sequence within the cDNA. In this case the template nucleic acid (1) must present the recognition sequence of a restriction endonuclease at the end of the functional sequence (2d) that is used for the hybridization. By means of the hybridization of a complementary DNA oligonucleotide and the subsequent digestion with the respective restriction endonuclease the hybridization sequence forms the 3'-end of the cDNA (2). The sequence of the cDNA forming the 3'-end may also be selected to assume, after the elimination of the template nucleic acid (1), a stem loop structure, whose stem is the recognition sequence of a restriction endonuclease. By means of digestion with the corresponding enzyme a 3'-end is produced that, after hybridization, may be used for the priming of reaction (7).

ANALYSIS PROCEDURES FOR THE DETECTION OF THE REACTION PRODUCT (STEP 3)

After step 2 of the PERT assay has been completed, the PCR, the LCR and the amplification procedures based on replicative DNA all present a dsDNA for further analysis. For the amplification procedures based on a transcription assay and for those based on replicative RNA the product to be analyzed is mainly a single-stranded RNA (ssRNA). The choice of procedure depends on various factors, e.g. on the selected type of assay, the equipment, the available manpower, etc. It is therefore neither possible nor necessary to list all possible types of procedures for each variant of the PERT assay. Instead, it is up to the specialist to select the optimal procedure under the specific circumstances given.

The possibilities quoted in the following are included for the purposes of illustration of the wide choice of techniques available for the detection of an amplification product of step 2; they are by no means comprehensive:

a) Detection of the DNA synthesis, resp. the RNA synthesis in the amplification reaction, b) Detection of the ssRNA, resp. dsDNA amplification product by means of chromatographic or electrophoretic analysis, c) Detection of the ssRNA, resp. the dsDNA amplification product by means of hybridization with specific probes, d) Detection with the help of a combination of elements from a) to c).

The following methodological elements may be used to these purposes:

Electrophoresis
  gel electrophoresis (native, denaturing): agarose, polyacrylamid, other gel materials
  capillary electrophoresis
Chromotography
  HPLC
Hybridization
  liquid hybridization
  hybridization to a solid phase: membranes, beads, plates
Reagents for the Visualization of DNA and/or RNA in General
  fluorescent dyes: ethidium bromide, acridin orange, Hoechst dyes, etc.
Reagents for the Labeling of Probes
  nucleotides for the labeling of probes: radioactive: $^{125}$I, $^{131}$I, $^{32}$P, $^{35}$S, $^{3}$H, $^{14}$C in dNTP and rNTP nonradioactive: biotin-dUTP, biotin-UTP, DIG-dUTP, DIG-UTP
  reagents that are not nucleotides, for the labeling of probes: photoreactive biotin, photoreactive DIG, aminoreactive biotin, aminoreactive DIG, sulfhydrylreactive biotin, sulfhydrylreactive DIG, fluorescent dyes (rhodamin, FITC, etc.)
Reagents for the Labeling of DNA/RNA During Synthesis (in Step 2)
  nucleotides for the labeling during synthesis (step 2): radioactive: $^{125}$I, $^{131}$I, $^{32}$P, $^{35}$S, $^{3}$H, $^{14}$C in dNTP and rNTP nonradioactive: biotin-dUTP, biotin-UTP, DIG-dUTP, DIG-UTP.

APPLICATION EXAMPLE #1

Figure 24:
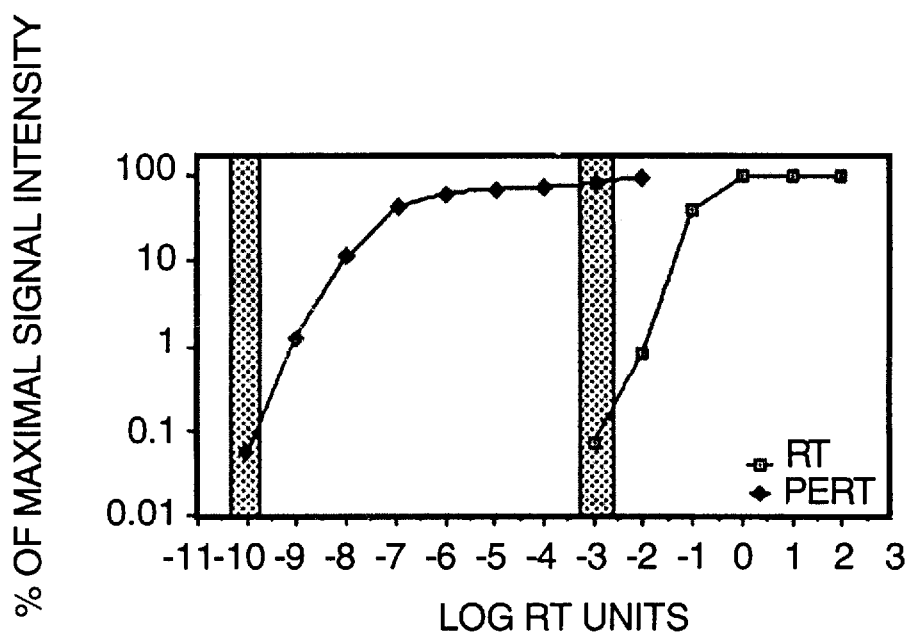
FIG. 24 presents a first example for the application of the PERT assay: a comparison of the analytical sensitivity of a reverse transcriptase assay (RT) and a PERT assay which is performed as illustrated in FIG. 2 and using MuLV reverse transcriptase.

FIG. 24 illustrates the increased sensitivity of the PERT assay in comparison to the conventional RT test.

PERT assay according to the variant of FIG. 2:

Step 1: RT reaction: Genomic RNA of the bacteriophage MS2 (Boehringer Mannheim) was used as template nucleic acid for the RT reaction in the PERT assay. A synthetic oligonucleotide of the base sequence 5'-d (CATAGGTCAAACCTCCTAGGAATG)-3' (SEQ ID NO: 1) was used as primer A. For the production of the template-primer combination, for each reaction 1 µg template nucleic acid (0.85 pmol) with 220 µg primer (27 pmol) was mixed in 4 µl of H$_2$O and then incubated for 5 min at 95° C., for 30 min at 37° C., and for 5 min at 4° C. The resulting template-primer combination was pipetted to a solution with reaction buffer, dNTPs, dithiothreitol, RNase inhibitor, and bovine serum albumin. The RT used was a recombinant enzyme of the Moloney murine leucemia virus (New England Biolabs). First, a tenfold dilution series, of 10$^2$ to 10$^{-10}$ units (U), was produced in a solution of 0.5M KCl, 17 mM Tris-Cl pH 7.5, 3.3 mM DTT, 0.3% triton X-100, and 33% glycerine. Of this solution, quantities of 2.5 µl containing the respective activity were then pipetted into a reaction mixture resulting in a total volume of 25 µl. Reaction conditions were as follows: 50 mM Tris-Cl pH 8.3; 50 mM KCl; 8 mM MgCl$_2$; 10 mM dithiothreitol; 1 U/µl RNase inhibitor (RNasin™); 0.12 µg/µl bovine serum albumin; 0.032% triton X-100; and 1 mM each of dATP, dCTP, dGTP, and dTTP. The reaction was incubated for 3 hours at 37° C.

The RT reaction was followed by the inactivation of the RNase inhibitor by means of incubation at 95° C. for 7 min. For the degradation of the template nucleic acid, each reaction sample was subsequently treated with 2.0 ng RNAse A (United States Biochemical) for 30 min at 37° C.

Step 2: Amplification by means of PCR: The MS-2 cDNA to be amplified, which was synthesized in step 1, was amplified by means of PCR with the primers A (see above) and B, of the base sequence 5'-d (TCCTGCTCAACTTCCTGTCGAG)-3'(SEQ ID NO: 2). For this reaction, 10 μl (40%) of the RT reaction product treated with RNase A was used in a total reaction volume of 100 μl and coated with 100 μl mineral oil. The reaction conditions were as follows: 50 mM KCl; 14 mM Tris-Cl pH 8.3; 2.1 mM MgCl$_2$; 0.01% gelatine; 350 nM primer A; 250 nM primer B; 300 μM each of dATP; dCTP, dGTP, dTTP; and 2.5 U Taq polymerase. The amplification was carried out in 25 cycles each with one denaturing segment at 94° C. for 30 sec, one hybridization segment at 55° C. for 1 min and 40 sec, and one synthesis segment at 72° C. for 1 min and 50 sec on a programmable thermal block (Techne PHC-2).

Step 3: Analysis: The detection of the reaction product was realized by means of Southern blot hybridization. To this purpose, 10% of the DNA of each amplification reaction were separated on a 1.5% agarose gel and transferred to a nylon membrane. An oligonucleotide C of the base sequence 5'-d(TTAATGTCTTTAGCGAGACGC)-3'(SEQ ID NO: 3) labeled at the 5'-end with a phosphate group containing a $^{32}$P was used for hybridization. The quantification of the radioactive signals was effected by measuring the Cerenkov radiation.

Conventional RT Test

The buffer conditions of the conventional RT test corresponded to those of the PERT assay. The indicated amount of enzyme was in each case contained in 10 μl, the reaction volume was 100 μl. 5 μg poly(rA)·oligo(dT) (Pharmacia) was used as template-primer combination, and $^3$H-labeled thymidin triphosphate served as the deoxribonucleotide monomer. This was incubated at 37° C. for 22 h. The reaction product was precipitated on a nylon filter by trichloroacetic acid and the incorporated radioactivity was analyzed with a scintillation counter.

FIG. 24 shows the intensity of the signal for both procedures, in dependence of the RT activity used, expressed as the percentage of the maximal signal intensity. It is evident that the PERT assay still shows the maximal intensity even far below $10^{-3}$ the detection limit (shaded area) of the conventional RT test, and that the detection limit of the PERT assay at $10^{-10}$ U is, by a factor of $10^7$, below that of the conventional RT test.

APPLICATION EXAMPLE #2

Figure 25:
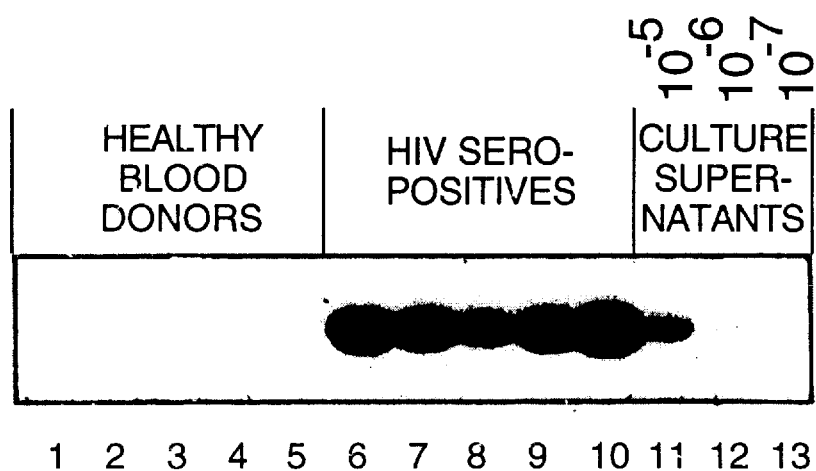
FIG. 25 presents another example of how the procedure described in FIG. 2 may be used: the direct detection of RT activity in the blood plasma of 5 HIV-infected patients resp. the absence of such activity in the blood plasma of 5 healthy blood donors.

FIG. 25 shows the presence of particle-associate RT activity in the blood sera of HIV-infected individuals and in the culture supernatant of HIV-infected cells.

One ml of plasma obtained from EDTA-anticoagulated blood was centrifuged for 30 min at 14'000×g and then passed through a 0.2 μm filter. The volume was adjusted to 2.25 ml by adding isotonic phosphate-buffered saline (PBS, GIBCO), and particulate material (virus particles) was sedimented for 2 h in an ultracentrifuge at 82'000×g. The pellet was resuspended in 40 μl buffer consisting of 50 mM KCl, 25 mM Tris-Cl pH 7.5, 5 mM dithiothreitol, 0.25 mM EDTA, 0.025% triton X-100, and 50% glycerol. Next, viruses presumed to be present were lysed by adding 20 μl of a solution of 1.5M KCl, and 0.9% triton X-100. 2.5 μl (4%) of this lysate were then added to a RT reaction.

Reaction conditions and the template-primer combination used for the RT reaction were the same as in example 1. The reaction at 37° C. was for 5 h. Following this, the RNase inhibitor was inactivated by means of high temperature treatment at 95° C. for 7 min. The hydrolysis of the RNA template nucleic acid was effected by means of incubation with 0.8 ng RNase A at 37° C. for 30 min, in the PCR reaction mixture, immediately preceding the amplification reaction. The conditions of the PCR reaction mixture, the number of cycles and the thermal profile were identical to those in example 1. The analysis of the amplified DNA was carried out by means of Southern blot hybridization with oligonucleotide C, as described above in example 1. The result was evaluated by autoradiography on an X-ray film.

FIG. 25 shows that no RT activity is detectable in the plasma of five healthy blood donors (tracks 1 to 5), while it is clearly detectable in the plasma of all HIV-infected patients (tracks 6 to 10). Similarly, in a culture supernatant of HIV-infected cells (tracks 11 to 13) an RT-activity is detectable up to a dilution of 1:1 million.

APPLICATION OF PERT ASSAYS

The PERT assay is an ultrasensitive assay for the detection of RT activity. This activity is a characteristic marker for retroelements. Apart from retroviruses these include retrovirus-like elements, with the subunits retrotransposons, pararetroviruses (caulimoviruses and hepadnaviruses) and LINE (long interspersed nuclear elements), on the other hand also non-retrovirus-like elements such as mitochondrial plasmids or msDNA (multicopy single stranded DNA) [for a recent survey of retroelements see Ricchetti M. Bull Inst Pasteur 1991; 89:147-58]. Retroelements thus include a wide range of partially infectious agents, which are important in human medicine, in veterinary medicine or in plant production by causing serious, sometimes fatal diseases and by resulting in reduced productivity in the case of animals resp. plants.

The invention therefore also describes procedures for the ultrasensitive detection of all retroviruses as well as all other retroelements containing or expressing active RT. It is thus evident that PERT assays are used for humans, animals or plants for the detection of such retroelements themselves or for the diagnosis of diseases associated with them.

Human retroelements include the known human pathogenic oncoretroviruses human T-cell leukemia virus type 1 and type 2 (HTLV-1 resp. -2), as well as the human immunodeficiency viruses type 1 and type 2 associated with AIDS and pre-AIDS (HIV 1 resp. HIV 2). An association with retroviruses has been postulated for various other diseases, e.g. for multiple sclerosis, Kawasaki syndrome, Chronic Fatigue syndrome, Sjögren syndrome, Graves' disease, certain proliferative blood diseases such as polycythemia or thrombocythemia, certain cutane T-cell lymphomas or mamma carcinoma. The group of human pathogenic pararetroviruses includes the hepatitis B virus, which is associated with acute or chronic hepatitis and liver cancer.

Animal retroelements include numerous retroviruses, including all those listed in the standard work RNA Tumor Viruses, 2nd edition, R. Weiss, N. Teich, H. Varmus, J. Coffin, edts., Cold Spring Harbor Laboratory, 1984 and 1985. They include, e.g., avian leucosis and sarcoma viruses (ALV resp. ASV), murine retroviruses (MLV/MSV/ MMTV), feline leucemia viruses (FeLV), the equine infectious anemia virus (EIAV), Visna virus, caprine arthritis/ encephalitis virus (CAEV), and the bovine leukemia virus (BLV). The designations express that many of these viruses cause malignant proliferative diseases, frequently of the blood or lymphatic system. Others cause chronic inflammations and degenerative diseases of the nervous system, joints, or other organs. Furthermore there are various types of simian immunodeficiency viruses (SIV), feline immunodeficiency viruses (FIV) and bovine immunodeficiency viruses (BIV) detected in recent years. Pararetroviruses include the animal hepadnaviruses with the woodchuck hepatitis virus (WHV), the ground squirrel hepatitis virus and the duck hepatitis B virus (DHBV).

Apart from the pararetroviruses already mentioned, which include plant infesting caulimoviruses such as the cauliflower mosaic virus, the group of retrovirus-like elements also contains the retrotransposons with the preferably transposable elements of drosophila spp., copia, gypsy, 17.6, 297, 412, or Saccharomyces cerevisiae as well as LINE. In addition to these retrovirus-like elements there is the group of non-retroviruslike elements, which consists of the mitochondrial plasmids and the msDNA.

Furthermore retroelements include all agents that are generated by natural recombination from existing retroelements, or by genetical manipulation. Obviously the PERT assay lends itself to the detection and the characterization of other retroelements and therefore is of particular importance for research.

The PERT assay can also be used for detecting RT activity associated with procaryotic cells or fragments thereof, with cellular and subcellular elements, viruses or particles of any kind, that is for RT activity of any possible origin.

Diagnostic use of the PERT assay can be in the form of screening or typing assays, of these the latter also have the function of confirmation tests. Of special significance is the screening of blood or organ donors. In this context it is especially important that one single screening assay can detect all retroelements, which is significantly easier and cheaper when compared to testing with a series of type- or sequence-specific tests.

The quantitative application of the PERT assay is also important. This measures the extent of an infection, the "virus load". In this context it is advantageous that the PERT assay only detects elements with functionally active RT. RT-inactive elements, which are irrelevant for the transmission or the propagation of an infection, are not detected.

Another important application is the screening of biological products, that is products consisting at least partially of biological material or produced therefrom, which are used in human or veterinary medicine or plant production for therapy, prophylaxis or other purposes. To give but a few illustrative examples that are by no means exclusive, these include sera, plasma preparations or plasma fractions, coagulation factors, vaccines, cell extracts, hormone preparations, cytokines as well as products generated by recombinant gene technology. The PERT assay can ensure that no infectious retroelements are transmitted by these products.

Wherever possible, biological products are nowadays inactivated by taking chemical, enzymatic and/or physical measures. The PERT assay allows a very sensitive control with regard to the desired success of the inactivation measures.

Medications that inhibit the RT are of outstanding importance in the treatment of infections with retroelements and the diseases they cause. Similar to antibiotics, however, drug-resistant virus variants develop. In the case of HIV it has been shown that virtually all patients have AZT-resistant virus variants after a two-year therapy with the RT inhibitor azidothymidin (AZT). The PERT assay allows to, directly ex vivo, that is by examining the sample taken from an infected patient, determine the effect of a RT inhibitor upon the population of active retroelements dominating at a given moment.

To sum up, the PERT assay lends itself to various applications in the areas of research, diagnosis, clinic and product control.

KITS FOR THE EASY APPLICATION OF PERT ASSAYS

An important aspect of this invention concerns kits for the detection of RT activity in a sample by means of the PERT assay. The term "kit" is here used to refer to packed, ready-to-use tools and reagents for the application of the PERT assay. The content of a kit is largely determined by the intended purpose and the particular variant or version of the PERT assay used. On the one hand, the term "kit" refers to "screening kits", which are used for deciding whether RT activity is present in a sample. In case of a positive test result, these do not provide any information concerning the origin of the RT activity. On the other hand, the term "kit" also refers to "typing kits", which serve to investigate the origin or cause of RT activity detected with the help of a "screening kit", respectively which clarify which retroelement, or which group of related retroelements, leads to this activity. Among others, the combination of the reagents of various typing kits is determined by the species the sample has been taken from, as well as by the spectrum and the frequency of retroelements known to occur in this species or in a particular sample population.

KITS FOR THE DETECTION OF RT ACTIVITY (SCREENING KITS)

Such a kit may contain the following: for step 1 of the PERT assay:

(1) suitable filters for the elimination of any undesired particular material from the sample;

(2) suitable reagents or tools for the enrichment of the RT activity in a fraction or phase of the sample chosen for further investigation;

(3) a suitable reagent for the mild extraction of RT activity from a fraction or phase chosen for further investigation;

(4) a RT master mixture consisting of one or several solutions which contains—except for the RT activity—all reagents needed for the RT reaction in suitable concentration in a suitable buffer solution; above all, this master mixture contains an adequate template-primer combination selected to correspond to the amplification procedure used in step 2, the necessary dNTPs, a suitable divalent cation ($Mn^{++}$ and/or $Mg^{++}$), and other substances supporting the reaction with regard to optimal specificity and sensitivity;

(5) a positive RT control consisting of a solution which contains an enzymatically active RT;

(6) a negative RT control consisting of a solution which does not contain any enzymatically active RT;

(7) one or several suitable reagents for the enzymatic and/or chemical degradation of the RNA, if this is necessary or desirable with regard to the conditions of the nucleic acid amplification procedure used in step 2; furthermore a suitable washing solution for washing this [RNA] away, in case the binding of the cDNA to a carrier allows a washing process, or a neutralization solution which then, with regard to pH, saline concentrations, and degrading reagents re-establishes reaction conditions needed for executing the necessary subsequent reactions of the respective variant or version of the PERT assay;

(8) one or several solutions containing those reagents, such as enzymes, primers resp. other oligonucleotides, reporter probes, dNTPs, resp. rNTPs, needed for the chosen variant or version of the PERT assay, whether for the transformation of the cDNA to a nucleic acid that presents the educt of step 2, or for the specific hybridization to the cDNA of a reporter probe that is either used as an educt in step 2 or based on which a nucleic acid is generated, which is then used as the educt in step 2; and, in this case, a suitable washing solution for washing away the non-hybridized surplus reporter probe;

for step 2 of the PERT assay:

(9) one or several solutions containing the primers resp. other oligonucleotides, enzymes, dNTPs, rNTPs needed in addition, depending on the PERT variant or version;

for step 3 of the PERT assay:

(10) reagents and reaction vessels for the analysis of the amplification product resulting from step 2 that have been adapted to the respective PERT assay variant or version.

KITS FOR THE TYPING OF RT ACTIVITY

These kits serve the purpose of linking the RT activity detected in the PERT assay to a specific retroelement or a group of related retroelements. This is achieved by means of reagents capable of specific reaction with at least one characteristic determinant of a given RT-containing retroelement, or of a group of such retroelements.

The typing kit can contain:

(1) Typing reagent: contains at least one sutiable reagent with sufficient affinity and specificity for at least one determinant that is characteristic of a given retroelement or a group of related retroelements.

The characteristic determinants reacting with the typing reagent are part of a particle or fragment associated with RT, or they are located on the enzyme itself. In case of the latter, the typing reagent may also be levelled directly against the "active site" of the enzyme or against its vicinity, thus inhibiting the enzyme activity. In any case, the characteristic determinants resp. the typing reagent must be chosen so that the interaction of the typing reagent with the determinants also means interaction—directly or indirectly—with the RT.

The typing reagent may consist of mono- or polyclonal antibodies with specificity for at least one of the characteristic determinants, or it may consist of other proteins, pharmacological substances or other molecules of any kind that will specifically bind to at least one of the respective determinants.

Preferably after preparing, but before adding the sample in reaction (3) of step 1, reagents that are directly levelled against the RT are to be added to the sample, the resulting mixture is to be incubated for a suitable time.

Reagents levelled against other determinants are to be added during the sample pretreatment at the most suitable moment.

The typing reagent may be added in soluble form, especially if it shows any activity directly inhibiting (neutralizing) the enzyme. A non-neutralizing typing reagent may be presented bound to a carrier, or it may, if presented in soluble form, be linked to reactive groups capable of enriching or reducing the RT activity in the fraction used for the PERT assay by using any fractionating method known among the experts.

(2) Negative control reagent: At least one suitable reagent that is as similar to the typing reagent as possible but does not bind to the determinant recognized by the typing reagent or to another determinant directly or indirectly associated with the respective RT. Depending on the type of typing reagent used, the negative control reagent also consists of monoclonal or polyclonal antibodies, other proteins, pharmacological substances or other suitable molecules and is equal to the typing reagent with regard to its fractionation properties.

(3) Positive RT control: This contains an enzymatically active preparation of RT with a certain concentration suitable for the retroelement defined by the typing reagent.

(4) Negative RT control: This contains a suitable RT that does not correspond to the typing agent and does not react with it.

(5) Fractionation reagent: If fractionation is necessary, this contains all further components needed. By interacting with the typing reagent, the fractionation reagent allows to enrich or reduce the RT bound to the typing reagent in the fraction used for the PERT assay. For example, the fractionation reagent may be a carrier the typing reagent is bound to or to which it is bound by reactive groups, it may also be an immunological reagent precipitating the typing reagent. Similarly, the negative control reagent will also interact with the fractionation reagent, however, this does not influence the RT since it does not bind to the negative control reagent.

A typing kit may contain the reagents (1) to (4) of a number of different retroelements in various combinations. Preferably the reagents are assorted in suitable combinations, so that detection of the most important retroelements in a given group is possible by means of one single kit. For example, a typing kit for the detection of human retroelements may contain the following typing reagents: those with specificity for the HIV group, within this group those with specificity for either HIV-1 or HIV-2; furthermore those with specificity for the HTLV group, again with those with specificity for either HTLV-1 or HTLV-2; furthermore one with a specificity for the hepatitis B virus.

It is fundamental to the invention that the PERT (Product-Enhanced Reverse Transcriptase) assay is an ultrasensitive 3-step procedure for the detection of reverse transcriptase (RT) activity.

In a first step the sample is pretreated by presenting a template-primer combination in a reaction mixture and by using the RT activity present in the pretreated sample for providing a nucleic acid to be amplified with a particular nucleic acid amplification procedure in such a way that this nucleic acid is only then provided if RT activity is present in the sample.

In the second step the nucleic acid to be amplified is amplified, the result being an amplification product. This is analysed and identified in the third step.

Compared to conventional RT assays the PERT assay achieves a several million-fold increase in sensitivity. The invention allows the ultrasensitive detection of RT activity, that is to say of all retroviruses as well as all other retroelements containing or expressing active RT. It is important for the diagnosis of infections and diseases caused by these in humans, animals and plants. PERT assays are used in research and diagnostics as screening tests, typing tests or as confirmatory tests. The invention includes kits developed to this purpose.

What is claimed is:

1. A method for detection of reverse transcriptase (RT) in a sample comprising:
   (a) pretreating the sample to make the total amount of reverse transcriptase contained therein available for a RT reaction; and eliminating from said sample factors which interfere with the RT reaction;
   (b) incubating the pretreated sample with a template-primer combination in a reaction mixture, said template-primer combination comprising a template nucleic acid and at least a RT primer;
   said RT primer being a nucleic acid which contains at least one functional sequence at least one of which is a hybridization sequence which extends to the 3'-end and by which the RT primer is hybridized to the template nucleic acid;
   said template nucleic acid being a heteropolymeric nucleic acid which contains at least one segment consisting of a heteropolymeric RNA which is located upstream of a hybridization sequence to which said RT primer is hybridized and which is capable of functioning as a template in a RT reaction, said template nucleic acid further containing at least one additional functional sequence located upstream of said hybridization sequence for the RT primer;
   (c) synthesizing a cDNA by reverse transcription catalyzed by said reverse transcriptase from the sample;
   (d) amplifying by an in vitro nucleic acid amplification reaction at least part of the sequence of a cDNA produced in step (c) or of a nucleic acid which has been derived from said cDNA;
   (e) analyzing and identifying the amplification product of step (d); and
   (f) correlating the presence of amplification product to the presence of reverse transcriptase activity in the pretreated sample.

2. A method according to claim 1, wherein said template-primer combination incubated in step (b) contains all functional sequences which will be required to amplify at least part of the sequence of a cDNA synthesized in step (c); and in step (d) that part of the cDNA sequence which contains these functional sequences is amplified.

3. A method according to claim 2, wherein said template-primer combination of step (b) contains a pair of non-overlapping hybridization sequences which will be used in the amplification reaction of step (d), at least one of these being located upstream of that hybridization sequence of the template nucleic acid to which the RT primer is hybridized; a cDNA synthesized in step (c) contains said pair of hybridization sequences; and in step (d) part of the sequence of said cDNA is selectively amplified by a polymerase chain reaction using two amplification primers which anneal to said pair of hybridization sequences.

4. A method according to claim 3, wherein the template nucleic acid is the genomic RNA of the bacteriophage MS2, the RT primer is a synthetic deoxyoligonucleotide of the base sequence 5'-d(CATAGGTCAAACCTCCTAGGAAT G)-3' (SEQ ID NO:1); and part of the MS2 cDNA synthesized in step (c) is selectively amplified in step (d) by polymerase chain reaction with synthetic deoxyoligonucleotide primers of the base sequence 5'-d (CATAGGTCAAACCTCCTAGGAATG)-3' (SEQ ID NO.: 1) and 5'-d(TCCTGCTCAACTTCCTGTCGAG)-3' (SEQ ID NO.: 2).

5. A method according to claim 2, wherein said template-primer combination of step (b) contains a pair of hybridization sequences immediately adjacent to each other which will be used in the amplification reaction of step (d), at least one of these being located entirely upstream of that hybridization sequence of the template nucleic acid to which the RT primer is hybridized; a cDNA synthesized in step (c) contains said pair of hybridization sequences; and in step (d) part of the sequence of said cDNA is selectively amplified by ligase chain reaction using said pair of hybridization sequences.

6. A method according to claim 2 wherein said template-primer combination of step (b) contains a pair of hybridization sequences which will be used in the amplification reaction of step (d), the hybridization sequences of said pair being separated from each other by a spacer sequence and at least one of them being located entirely upstream of that hybridization sequence of the template nucleic acid to which the RT primer is hybridized; a cDNA synthesized in step (c) contains said pair of hybridization sequences; and in step (d) part of the sequence of said cDNA is selectively amplified by a combination of a polymerase chain reaction and a ligase chain reaction using said pair of hybridization sequences.

7. A method according to claim 2, wherein said template-primer combination of step (b) contains a pair of non-overlapping hybridization sequences which will be used in the amplification reaction of step (d), at least one of these being located entirely upstream of that hybridization sequence of the template nucleic acid to which the RT primer is hybridized;
   said cDNA synthesized in step (c) contains said pair of hybridization sequences;
   in step (d) that part of said cDNA synthesized in step (c) which contains said pair of hybridization sequences is selectively amplified by
   (i) employing a multienzymatic transcription-based procedure which uses said pair of hybridization sequences and reaction conditions that maintain the stability of the RNA; and
   (ii) excluding the template RNA from amplification by prior treatment with at least one method selected from the group consisting of enzymatic degradation, chemical degradation, physical degradation, and dissociating the template RNA from a solid-phase-bound cDNA and washing it away.

8. A method according to claim 2, wherein said template-primer combination of step (b) contains a pair of non-overlapping hybridization sequences and a transcription promoter sequence which will be used in the amplification reaction of step (d), at least one hybridization sequence of said pair being located entirely upstream of that hybridization sequence of the template nucleic acid to which the RT primer is hybridized;
   said cDNA synthesized in step (c) contains the P(−) sequence of said transcription promoter located upstream of said pair of hybridization sequences;
   in step (d) that part of said cDNA synthesized in step (c) which contains said pair of hybridization sequences and said P(−) sequence is selectively amplified by
   (i) employing a multienzymatic transcription-based procedure using said pair of hybridization sequences and said P(−) sequence under reaction conditions that maintain the stability of the RNA, and by
   (ii) excluding the template RNA from amplification by prior treatment with at least one method selected from the group consisting of enzymatic degradation, chemical degradation, physical degradation, and dissociating the template RNA from a solid-phase-bound cDNA and washing it away.

9. A method according to claim 2, wherein the template-primer combination of step (b) contains all sequence elements of a replicative DNA; said template nucleic acid comprises, in 5' to 3' order, a DNA-ori(−) sequence which extends to the 5'-end and consists of a nucleic acid selected from the group comprising RNA and DNA, a spacer sequence, and a primer hybridization sequence which contains at least part of a DNA-ori(+) sequence extending to the 3'-end of said primer hybridization sequence;

said RT primer is a single-stranded DNA oligonucleotide which is in its entire length hybridized to at least the 3' terminal part of said DNA-ori(+) sequence of said template nucleic acid;

said cDNA synthesized in step (c) is a primary replicative DNA which contains a DNA-ori(−) sequence which extends to the 5'-end, a spacer sequence, and a DNA-ori(+) sequence which extends to the 3'-end, the hybridization of said 3' terminal DNA-ori(+) sequence to a 5' terminal DNA-ori(−) sequence constituting an active DNA-ori;

in step (d) said cDNA is amplified by i) eliminating the template RNA at least partially by at least one method selected from the group comprising enzymatic degradation, chemical degradation, physical degradation, and dissociating the template RNA from a solid-phase-bound cDNA and washing it away, and (ii) performing in a reaction mixture which contains dNTPs, a DNA replication procedure which involves binding of a protein primer to said active DNA-ori and replicating said replicative DNA by means of a DNA replicase that binds to said protein-primed replicative DNA.

10. A method according to claim 1, wherein said template nucleic acid of step (b) is RNA and contains at least one further hybridization sequence located upstream of that to which said RT primer is hybridized; said RT primer carries a functional group; a cDNA synthesized in step (c) contains said functional group and said at least one further hybridization sequence; a nucleic acid amplified in step (d) is derived from said cDNA by eliminating the template RNA at least partially with at least one method selected from the group consisting of enzymatic degradation, chemical degradation, physical degradation, and dissociating the template RNA and washing it away from a cDNA which has been bound to a solid phase by means of said functional group; hybridizing a reporter probe which contains all functional sequences used in an amplification reaction to at least one of said at least one further hybridization sequence of a cDNA; hybridized reporter probe is bound to a solid phase by means of said functional group of the cDNA; unbound reporter probe is removed; and at least part of said hybridized reporter probe which is the nucleic acid derived from said cDNA is amplified.

11. A method according to claim 10, wherein said reporter probe is a DNA which contains a hybridization sequence by which it is hybridized to said cDNA and a pair of hybridization sequences which will be used in the amplification reaction of step (d); and that part of said reporter probe which contains said pair of hybridization sequences is amplified in step (d) by a method selected from the group consisting of a polymerase chain reaction (PCR), a ligase chain reaction (LCR), a combination of PCR and LCR, and a multienzymatic transcription-based procedure.

12. A method according to claim 10, wherein said reporter probe is a RNA which contains a hybridization sequence by which it is hybridized to a cDNA and a pair of hybridization sequences which will be used in the amplification reaction of step (d) and a part of this reporter probe which contains said pair of hybridization sequences is amplified in step (d) by a multienzymatic transcription-based procedure.

13. A method according to claim 10, wherein said reporter probe is a primary replicative RNA which comprises a hybridization sequence by which it is hybridized to a cDNA, a RNA-ori (−) sequence extending to its 5'-end, a RNA-ori (+) sequence extending to its 3'-end and a replicase-binding domain in between; and said reporter probe is amplified in step (d) by means of a RNA replication system which comprises rNTPs in a reaction mixture and a RNA replicase that binds to the replicase binding domain of said reporter probe and replicates said reporter probe.

14. A method according to claim 10, wherein said reporter probe is at least one nucleic acid selected from the group comprising (i) a primary replicative DNA which comprises a DNA-ori(−) sequence extending to its 5'-end, a hybridization sequence by which it is hybridized to a cDNA, and a DNA-ori(+) sequence extending to its 3'-end, (ii) a partially double-stranded primary replicative DNA which comprises a DNA-ori(−) sequence extending to its 5'-end, a hybridization sequence by which it is hybridized to a cDNA, and a DNA-ori(+) sequence extending to its 3'-end, said 3'-terminal sequence of said reporter probe being primed with a single-stranded DNA oligonucleotide which comprises at least the first 6 nucleotides of a DNA-ori(−) sequence, and (iii) a partially double-stranded primary replicative DNA which consists of one strand comprising a DNA-ori(−) sequence extending to the 5'-end, a hybridization sequence located further downstream which is complementary to said at least one further hybridization sequence of said cDNA, and a second hybridization sequence extending to the 3'-end to which is hybridized a second strand of DNA which contains a corresponding hybridization sequence extending to the 3'-end and a DNA-ori(−) sequence extending to the 5'-end; and said primary replicative DNA is amplified in a reaction mixture which contains dNTPs by means of a DNA replication system which involves binding of a protein primer to the DNA-ori of said primary replicative DNA and replicating said replicative DNA by means of a DNA replicase that binds to said protein-primed replicative DNA.

15. A method according to claim 1, wherein a nucleic acid amplified in step (d) is one which has been derived from said cDNA produced in step (c) by at least one further reaction selected from the group consisting of:

(i) hybridizing to said cDNA a single-stranded DNA which comprises at least a hybridization sequence which extends to the 3'-end, (ii) synthesizing by enzymatic catalysis an at least partially double-stranded DNA, (iii) synthesizing a RNA by enzymatic catalysis, (iv) eliminating the template nucleic acid at least partially, and (v) ligating the 3'-end of the cDNA with the 5'-end of another nucleic acid which is hybridized to the template nucleic acid.

16. A method according to claim 15, wherein said template nucleic acid of step (b) is RNA and contains a pair of non-overlapping hybridization sequences which will be used in the amplification reaction of step (d), at least one of these being located upstream of that hybridization sequence to which said RT primer is hybridized; said template nucleic acid further contains a P(−) sequence of a transcription promoter which is located upstream of said pair of hybridization sequences and a further hybridization sequence whose 5' boundary is located upstream of or at the 5' boundary of said P(−) sequence; said cDNA produced in step (c) contains the hybridization sequence of said RT primer, said pair of hybridization sequences, further downstream a complete P(+) sequence and said further hybridization sequence; in step (d) a nucleic acid is derived from said cDNA by (i) eliminating the template RNA at least partially by treatment with at least one method selected from the group comprising enzymatic degradation, chemical degradation, physical degradation, and dissociating the template RNA from a solid-phase-bound cDNA and washing it away;

(ii) hybridizing a DNA oligonucleotide primer to said further hybridization sequence of the cDNA;

(iii) synthesizing by means of catalysis by a DNA-dependent DNA polymerase and dNTPs an at least partially double-stranded DNA which contains a functional transcription promoter; and (iv) synthesizing by means of catalysis by the corresponding DNA-dependent RNA polymerase and rNTPs from said transcription promoter a RNA which contains said pair of non-overlapping hybridization sequences; said synthesized RNA, which is the nucleic acid derived from the cDNA, is amplified by means of a multienzymatic transcription-based procedure; and the reaction conditions are such that the stability of the RNA is maintained.

17. A method according to claim 15, wherein said template nucleic acid of step (b) consists of RNA and contains a further hybridization sequence located upstream of and non-overlapping with that hybridization sequence to which said RT primer is hybridized; said RT primer is a single-stranded DNA oligonucleotide, whose 5' terminal sequence consists of a DNA-ori(−) sequence corresponding to a DNA replication system; said cDNA synthesized in step (c) contains said DNA-ori(−) sequence which extends to the cDNA's 5'-end, said hybridization sequence of the RT primer and further downstream said further hybridization sequence; in step (d) a nucleic acid is derived from said cDNA by (i) hybridizing to said further hybridization sequence of the cDNA a single-stranded DNA primer whose 5' terminal sequence consists of said DNA-ori(−) sequence; and (ii) synthesizing by means of catalysis by a DNA-dependent DNA polymerase and dNTPs an at least partially double-stranded DNA which has a DNA-ori at least at one end and is a primary replicative DNA;

and said primary replicative DNA, which is the nucleic acid derived from said cDNA, is amplified in a reaction mixture which contains dNTPs by means of a DNA replication system which involves binding of a protein primer to the DNA-ori of said primary replicative DNA and replicating said replicative DNA by means of a DNA replicase that binds to said protein-primed replicative DNA.

18. A method according to claim 15, wherein said template nucleic acid of step (b) consists of RNA and contains a further hybridization sequence located upstream of and separated by a spacer sequence from that hybridization sequence to which said RT primer is hybridized; said RT primer is a partially double-stranded DNA adaptor of which the strand hybridized to said template nucleic acid comprises at its 5' terminal sequence the DNA-ori(−) sequence of a replicative DNA, to which a second DNA oligonucleotide is hybridized whose 3' terminal sequence consists of a DNA-ori(+) sequence; to said further hybridization sequence of the template nucleic acid a second partially double-stranded DNA adaptor is hybridized by a hybridization sequence which extends to the 5'-end of the adaptor's longer DNA strand; said second adaptor's longer strand is phosphorylated at its 5'-end and comprises a DNA-ori(+) sequence which extends to its 3'-end and to which a DNA oligonucleotide whose 5' terminal sequence consists of a complete DNA-ori(−) sequence is hybridized; said cDNA synthesized in step (c) fills the gap between these two adapters such that said cDNA is separated from said second adaptor by just one nick; in step (d) a nucleic acid is derived from said cDNA by closing said nick by means of enzymatic ligation of the 3'-end of the cDNA with the 5'-end of said second adaptor, whence a primary replicative DNA is formed; and said primary replicative DNA, which is the nucleic acid derived from the cDNA, is amplified in a reaction mixture which contains dNTPs by means of a DNA replication system which involves binding of a protein primer to the DNA-ori of said primary replicative DNA and replicating said replicative DNA by means of a DNA replicase that binds to said protein-primed replicative DNA.

19. A method according to claim 1, wherein said template nucleic acid of step (b) is RNA and contains at least one further hybridization sequence located upstream of that to which said RT primer is hybridized; said cDNA synthesized in step (c) contains said at least one further hybridization sequence; a nucleic acid amplified in step (d) is derived from said cDNA by hybridizing a reporter probe to at least one of said at least one further hybridization sequence of said cDNA and by subjecting the reaction mixture to at least one further reaction selected from the group consisting of:

(i) synthesizing a RNA by enzymatic catalysis, (ii) eliminating the template RNA at least partially, (iii) synthesizing an at least partially double-stranded DNA by enzymatic catalysis, and (iv) cleaving a double-stranded DNA by enzymatic catalysis.

20. A method according to claim 19, wherein said template nucleic acid contains one further hybridization sequence that extends to its 5'-end; said further hybridization sequence consists in its 3' terminal sequence of a P(−) sequence of a transcription promoter which is upstream directly followed by at least the first three nucleotides of a 3'-RNA-ori(+) sequence; said cDNA synthesized in step (c) contains said further hybridization sequence which extends to the 3'-end; a nucleic acid amplified in step (d) is derived from said cDNA by (i) hybridizing a reporter probe to said further hybridization sequence of the cDNA, said reporter probe being a single-stranded DNA which contains, extending to its 5'-end, the 5'-RNA-ori(−) sequence of a replicative RNA, further downstream a replicase binding domain, still further downstream a 3'-RNA-ori(+) sequence which is directly followed by the P(−) sequence of said transcription promoter; the hybridization sequence of said reporter probe consisting of said at least three last nucleotides of said 3'-RNA-ori(+) sequence and the entire P(−) sequence of said transcription promoter; the hybridization of said reporter probe to said further hybridization sequence of said cDNA constituting a functional transcription promoter, and (ii) synthesizing from said transcription promoter a primary replicative RNA by means of catalysis by the corresponding DNA-dependent RNA polymerase and rNTPs;

and said primary replicative RNA, which is the nucleic acid derived from the cDNA, is amplified by means of an RNA replication system which comprises rNTPs in a reaction mixture and an RNA replicase that binds to the replicase binding domain of said primary replicative RNA and replicates said primary replicative RNA.

21. A method according to claim 19, wherein a nucleic acid amplified in step (d) is derived from said cDNA by (i) eliminating the template RNA at least partially with at least one method selected from the group comprising enzymatic degradation, chemical degradation, physical degradation, and dissociating the template RNA from a cDNA by denaturation and washing it away;

(ii) hybridizing a smart probe to said at least one further hybridization sequence of said cDNA, said smart probe being a single-stranded DNA which contains, in 5' to 3' order, the P(+) sequence of a transcription promoter, a spacer sequence, a hybridization sequence complementary to said at least one further hybridization sequence of said cDNA, a further spacer sequence not complementary to the first, and the P(−) sequence of said transcription promoter directly followed by at least the first three nucleotides of a 5'-RNA-ori(−) sequence, whereby said P(−) sequence and said 5'-RNA-ori(−) nucleotides form a further hybridization sequence which extends to the 3'-end of said smart probe and is designated for the hybridization of a DNA reporter probe;

(iii) hybridizing to said further hybridization sequence of said smart probe a single-stranded DNA reporter probe which contains, in 5' to 3' order, a 5'-RNA-ori(−) sequence, a replicase binding domain, and a 3'-RNA-ori(+) sequence directly followed by the P(+) sequence of said transcription promoter, whence a functional transcription promoter is generated; and (iv) synthesizing from said transcription promoter a primary replicative RNA by means of catalysis by the corresponding DNA-dependent RNA polymerase and rNTPs; and said primary replicative RNA, which is the nucleic acid derived from the cDNA, is amplified by means of an RNA replication system which comprises rNTPs in a reaction mixture and an RNA replicase that binds to the replicase binding domain of said primary replicative RNA and replicates said primary replicative RNA.

22. A method according to claim 19, wherein said template nucleic acid of step (b) contains one further hybridization sequence which extends to its 5'-end; said cDNA synthesized in step (c) contains the corresponding further hybridization sequence extending to its 3'-end; a nucleic acid amplified in step (d) is derived from said cDNA by (i) hybridizing a single-stranded DNA reporter probe to said further hybridization sequence of the cDNA, said reporter probe comprising upstream of a hybridization sequence by which it is hybridized to said further hybridization sequence of the cDNA multiple repetitive copies of a sequence which contains a recognition site for a restriction endonuclease;

(ii) synthesizing a double-stranded DNA by means of catalysis by a DNA-dependent DNA polymerase and dNTPs;

(iii) cleaving said double-stranded DNA by means of said restriction endonuclease, thereby generating several molecules of said double-stranded fragment; said fragment, which is the nucleic acid derived from said cDNA, is amplified in repeated cycles of denaturation, hybridization to said reporter probe, DNA synthesis, and restriction endonuclease cleavage.

23. A method according to claim 1, wherein at least one nucleic acid of the group consisting of the RT primer, a nucleic acid other than the RT primer which is hybridized to the template nucleic acid, a cDNA, a nucleic acid that is hybridized to the cDNA, a nucleic acid that is hybridized to a reporter probe, and a nucleic acid amplified in a amplification reaction carries a functional group which has at least one property selected from the group comprising being a solid phase, mediating the binding to a solid phase, being a ligand, and possessing at least one antigenic determinant.

24. A method according to claim 1 wherein, after having synthesized said cDNA in step (c), the template RNA is eliminated at least partially by treatment with at least one method selected from the group consisting of enzymatic degradation, chemical degradation, physical degradation, and dissociating the template RNA from a solid-phase-bound cDNA and washing it away.

25. A screening kit for the detection of a reverse transcriptase in accordance with the method of claim 1 comprising at least:

(i) reagents and auxiliary devices for the pretreatment of a sample including a isotonic sample dilution buffer, 0.2 $\mu$m filters, a reverse transcriptase extraction buffer containing salts, protein stabilizers and a mild detergent;

(ii) a RT master mixture comprising at least a buffer system, salts, a heteropolymeric template RNA, a heteropolymeric RT primer, dATP, dCTP, dGTP, and dTTP, a divalent cation selected from the group comprising $Mg^{2+}$ and $Mn^{2+}$, at least one protein stabilizer, a RNase inhibitor, (iii) a RNase for the digestion of the template RNA;

(iv) at least one further oligonucleotide matched to the reverse-transcribed template RNA and reagents for a in vitro nucleic acid amplification reaction comprising at least the enzymes, nucleotide triphosphates, salts, divalent cations, and buffers;

(v) at least one positive RT control comprising a solution which contains an enzymatically active reverse transcriptase; and at least one negative RT control consisting of a solution which does not contain any enzymatically active reverse transcriptase.

26. A screening kit for the detection of a reverse transcriptase in accordance with the kit of claim 25, wherein in (iv) said reagents for an in vitro nucleic acid amplification reaction are those used in a polymerase chain reaction and comprise at least a Taq polymerase, dATP, dCTP, dGTP, dTTP, salts, a divalent cation, and buffers.

* * * * *